United States Patent [19]

Rubin et al.

[11] Patent Number: 5,834,279
[45] Date of Patent: Nov. 10, 1998

[54] METHODS OF IDENTIFYING COMPOUNDS THAT INHIBIT DNA SYNTHESIS IN MYCOBACTERIUM TUBERCULOSIS AND COMPOSITIONS, REAGENTS AND KITS FOR PERFORMING THE SAME

[75] Inventors: Harvey Rubin; Fude Yang, both of Philadelphia; David Avarbock, Lansdale; Sean Curran, Mountaintop, all of Pa.

[73] Assignee: Trustees of the University of Pennsylvania, Philadelphia, Pa.

[21] Appl. No.: 813,940

[22] Filed: Mar. 3, 1997

Related U.S. Application Data

[63] Continuation-in-part of Ser. No. 612,271, Mar. 7, 1996, abandoned.

[51] Int. Cl.[6] .............................. C12N 15/31; C12N 1/21; C12N 9/02; C12N 9/03
[52] U.S. Cl. ...................... 435/189; 435/320.1; 435/183; 435/195; 435/252.3; 435/254.11; 435/325; 435/410; 536/23.1; 536/23.2
[58] Field of Search ................................ 435/320.1, 183, 435/189, 195, 252.3, 254.11, 325, 410; 536/23.1, 23.2

[56] References Cited

U.S. PATENT DOCUMENTS

| | | | |
|---|---|---|---|
| 4,736,866 | 4/1988 | Leder et al. | 800/1 |
| 4,873,191 | 10/1989 | Wagner et al. | 435/172.3 |

OTHER PUBLICATIONS

Yang F, et al. Characterization of two genes encoding the *Mycobacterium tuberculosis* ribonucleotide reductase small subunit. J Bacteriol. 1997 Oct. 1; 179(20): 6408–6415.

Yang F, et al. Cloning, expression, purification and characterization of DNA topoisomerase I of *Mycobacterium tuberculosis*. Gene. 1996 Oct. 31; 178(1–2): 63–69.

Mahairas GG, et al. Molecular analysis of genetic differences between Mycobacteriumbovis BCG and virulent M. bovis. J Bacteriol. 1996 Mar. 1; 178(5): 1274–1282.

Philipp WJ, et al. An integrated map of the genome of the *tubercle bacillus, Mycobacterium tuberculosis* H37Rv, and comparison with Mycobacteriumleprae. Proc Natl Acad Sci U S A. 1996 Apr. 2; 93(7): 3132–3137.

Tse–Dinh YC, et al Complete nucleotide sequence of the topA gene encoding *Escherichia coli* DNA topoisomerase I. J Mol Biol. 1986 Oct. 5; 191(3): 321–331.

Bachmayer, H., "Initiation of Protein Synthesis in Intact Cells and in Isolated Chloroplasts of *Acetabularia mediterranea*", *Biochim. Biophys. Acta*, 1970, 209, 584–586.

Balasubramanian, V. et al., "Allelic Exchange in *Mycobacterium tuberculosis* with Long Linear Recombination Substrates", *J. Bacteriol*, 1996, 178 (1), 273–279.

Bradford, M., "A Rapid and Sensitive Method for the Quantitation of Microgram Quantities of Protein Utilizing the Principle of Protein–Dye Binding", *Analytical Biochem.*, 1976, 72, 248–254.

Carroll, R., "The Inactivation of *Escherichia coli* RNA Polymerase by $Mg^{2+}$ and Nucleoside Triphosphates and the Reactivation by Salt", *Biochim. Biophys. Acta*, 1970, 209, 581–583.

Henriksen, M. et al., "The Stable Tyrosyl Radical in Mouse Ribonucleotide Reductase is Not Essential for Enzymatic Activity", *J. Am. Chem. Soc.*, 1994, 116, 9773–9774.

Jordan, A. et al., "Cloning and Sequencing of the Genes from *Salmonella typhimurium* Encoding a New Bacterial Ribonucleotide Reductase", *J. Bacteriology*, 1994, 176(11), 3420–3427.

Jordon, A. et al., "A Second Class I Ribonucloetide Reductase in Enterobacteriaceae: Characterization of the *Salmonella typhimurium* Enzyme", *PNAS USA*, 1994, 91, 12892–12896.

Liuzzi, M. et al., "A Potent Peptidomimetic Inhibitor of HSV Ribonucleotide Reductase With Antiviral Activity in vivo", *Nature*, 1994, 372, 695–698.

Mann, G. et al., "Purification and Characterization of Recombinant Mouse and Herpes Simplex Virus Ribonucleotide Reductase R2 Subunit", *Biochemistry*, 1991, 30, 1939–1947.

Moser, C. et al., "Biological Electron Transfer", *J. Bioenergetics and Biomembranes*, 1995, 27 (3), 263–274.

Nordlund, P. et al., "Three–Dimensional Structure of the Free Radical Protein of Ribonucleotide Reductase", *Nature*, 1990, 345, 593–598.

Reichard, P., "From RNA and DNA, Why so many Ribonucleotide Reductases?", *Science*, 1993, 260, 1773–1777.

Rova, U. et al., "Evidence by Site–Directed Mutagenesis Supports Long–Range Electron Transfer in Mouse Ribonucleotide Reductase", *Biochemistry*, 1995, 34, 4267–4275.

Rubin, H. et al., "Cloning, Expression, Purification, and Biological Activity of Recombinant Native and Variant Human α1–Antichymotrypsins", *J. Biol. Chem.*, 1990, 265 (2), 1199–1207.

Sahlin, M. et al., "Transient Free Radicals in Iron/Oxygen Reconstitution of Mutant Protein R2 Y122F", *J. Biol. Chem.*, 1995, 270 (21), 12361–12372.

Salem, J. et al., "High Level Expression of the Large Subunit of Mouse Ribonucleotide Reductase in a Baculovirus System", *FEBS Letters*, 1993, 323 (1,2), 93–95.

Schaper, K.–J. et al., "Development of Inhibitors of Mycobacterial Ribonucleotide Reductase", *Lepr. Rev.*, 1986, 57 Suppl. 3, 254–264.

(List continued on next page.)

*Primary Examiner*—Robert A. Wax
*Assistant Examiner*—Bradley S. Mayhew
*Attorney, Agent, or Firm*—Woodcock Washburn Kurtz Mackiewicz & Norris, LLP

[57] ABSTRACT

Nucleic acid molecules that encode R2 subunit protein and topoisomerase I protein, fragments thereof, recombinant expression vectors and host cells are disclosed. Oligonucleotide molecules with nucleotide sequences complimentary to a nucleotide sequence encode R2 subunit protein and topoisomerase I protein are disclosed.

18 Claims, No Drawings

OTHER PUBLICATIONS

Seydel., J.K. et al., "Experimental Drugs and Combination Therapy", *Immunobiol.,* 1994, 191, 569–577.

Steeper, J.R. and Steuart, "A Rapid Assay for CDP Reductase Activity in Mammalian Cell Extracts", *Analytical Biochem.,* 1970, 34, 123–130.

Stubbe, J., "Ribonucleotide Reductases" in Advances in Enzymology and Related Areas of Molecular Biology, Meister, ed., vol. 63, John Wiley & Sons, New York, 1990, pp. 349–419.

Wheeler, P.R., "Biosynthesis and Scavenging of Purines by Pathogenic Mycobacteria Including *Mycobacterium leprae*", *J. of Gen. Microbiol.,* 1987, 133, 2999–3011.

Wheeler, P.R., "Enzymes for Purine Synthesis and Scavenging in Pathogenic Mycobacteria and Their Distribution in *Mycobacterium leprae*", *J. Gen. Microbiol.,* 1987, 133, 3013–3018.

Wheeler, P.R., "Biosynthesis and Scavenging of Pyrimidines by Pathogenic Mycobacteria", *J. General Microbiology,* 1990, 136, 189–201.

Winder, F.G. and McNulty, "Increased DNA Polymerase Activity Accompanying Decreased DNA Content in Iron–Deficient *Mycobacterium smegmatis*", *Biochim. Biophys. Acta,* 1970, 209, 578–580.

Winder, F.G. and Barber, "Effects of Hydroxyurea, Nalidixic Acid and Zinc Limitation on DNA Polymerase and ATP–Dependent Deoxyribonuclease Activities of *Mycobacterium smegmatis*", *J. Gen. Microbiol.,* 1973, 76, 189–196.

Yang, F. et al., "Isolation of Ribonucleotide Reductase from *Mycobacterium tuberculosis* and Cloning, Expression, and Purification of the Large Subunit", *J. Bacteriol.,* Nov. 1994, 176 (21), 6738–6743.

Yang, F.–D. et al., "The Carboxyl Terminus Heptapeptide of the R2 Subunit of Mammalian Ribonucleotide Reductase Inhibits Enzyme Activity and Can be Used to Purify the R1 Subunit", *FEBS Letters,* 1990, 272 (1,2), 61–64.

METHODS OF IDENTIFYING COMPOUNDS THAT INHIBIT DNA SYNTHESIS IN MYCOBACTERIUM TUBERCULOSIS AND COMPOSITIONS, REAGENTS AND KITS FOR PERFORMING THE SAME

CROSS REFERENCE TO RELATED PATENT APPLICATIONS

This application is a continuation in part of U.S. Ser. No. 08/612,271 filed Mar. 7, 1996, now abandoned, which is incorporated herein by reference.

FIELD OF THE INVENTION

The invention relates to methods of identifying specific inhibitors of *Mycobacterium tuberculosis* DNA synthesis enzymes including complementation assays and in vitro activity assays. The invention relates to the identification and cloning of genes encoding the small subunit (R2) of the *M. tuberculosis* ribonucleotide reductase (RR) gene and the gene encoding topoisomerase I gene, to the isolated proteins encoded by the genes and to methods of using the genes and the proteins.

BACKGROUND OF THE INVENTION

Tuberculosis (TB) in all of its manifestations is the leading cause of death from a single infectious agent. Studies from two urban centers indicate that 30–40% of new cases are the result of recent infection rather than reactivation of old disease, and cases acquired by recent transmission accounted from almost ⅔ of drug resistant TB.

Highly resistant strains of *M. tuberculosis* have been isolated from patients in the Philadelphia area at a rate that requires physicians to treat every new case of presumed TB with at least four drugs, i.e., to consider every new case as if it were caused by one of these resistant strains. Clearly, new approaches to the development of antituberculous therapy are necessary. However, the difficulties of working with *Mycobacterium tuberculosis* has kept the field from developing apace with the advances in molecular biology and biotechnology. In particular, the analysis of the regulation of DNA replication, traditionally a rich area for the discovery of new antimicrobial agents and one that would provide major new insights into the growth of Mycobacteria, has been slow to develop.

The biochemistry of DNA replication of Mycobacteria is not fully understood. The mean generation time for *M. tuberculosis* is 24 hours compared to 3 hours of *M. smegmatis* and 1.3 hours for *E. coli*. Genomic DNA is replicated in approximately 10 hours in *M. tuberculosis* whereas the comparable times for *M. smegmatis* and *E. coli* are 1.8 and 1 hours respectively. The de novo and scavenging pathways for purines and pyrimidines in *Mycobacteria avium, microti* and *leprae* have been described. However, the molecular characterization of the enzymes in these pathways has not yet been accomplished.

There is a need for compounds which selectively inhibit *M. tuberculosis* enzymes involved in DNA synthesis. There is a need for reagents, compositions, kits and methods of identifying such compounds.

SUMMARY OF THE INVENTION

The present invention provides complementation assays which are useful to identify agents that inhibit the activity of *M. tuberculosis* DNA synthesis enzymes. According to the invention, host cells are provided which do not have a functioning endogenous DNA synthesis enzyme but which are provided with a functioning homologous *M. tuberculosis* DNA synthesis enzyme. Test compounds are evaluated for their ability to inhibit the *M. tuberculosis* DNA synthesis enzyme in the complemented host cell.

The effect of test compounds on the host cells that contain a non-functioning endogenous DNA synthesis enzyme and the homologous *M. tuberculosis* DNA synthesis enzyme is compared to the effect of test compounds on host cells that contain a functioning endogenous DNA synthesis enzyme or a homologous non-*M. tuberculosis* DNA synthesis enzyme.

As used herein, the term "first host cells" is meant to refer to the host cells that contain a non-functioning endogenous DNA synthesis enzyme and the homologous *M. tuberculosis* DNA synthesis enzyme.

As used herein, the term "second host cells" is meant to refer to host cells that contain a functioning endogenous DNA synthesis enzyme or a homologous non-*M. tuberculosis* DNA synthesis enzyme.

The first host cells and the second host cells are the same species. In some preferred embodiments, the first host cells and the second host cells are *E. coli*, Bacillus sp., Salmonella sp. and *S. cerevisiae*. In some preferred embodiments, the first host cells and the second host cells are *E. coli*.

The first host cells contain a non-functioning endogenous DNA synthesis enzyme. The first host cells may be temperature sensitive mutants in which the endogenous DNA synthesis enzyme functions within a temperature range but is non-functioning outside of the range, usually non-functioning at an elevated temperature. The first host cells may be designed so that the express the functional endogenous DNA synthesis enzyme under specific conditions which can be changed to prevent expression of the functioning endogenous enzyme. For example, the gene that encodes the endogenous enzyme may be placed under the control of a regulatable promoter. In preferred embodiments, the host cell is a mutant *E. coli* in which the endogenous DNA synthesis enzyme functions within a temperature range but is non-functioning at an elevated temperature.

*M. tuberculosis* DNA synthesis enzymes are those which participate in the reactions which occur in the synthesis of DNA. Examples of such *M. tuberculosis* DNA synthesis enzyme include: ribonucleotide reductase (RR), topoisomerase enzymes including topoisomerase I, dihydrofolate reductase, thymidylate synthase, DNA polymerase and RNA polymerase as well as any of the other several enzymes involved in the pathways which lead to DNA synthesis. In some preferred embodiments, the present invention provides complementation assays which are useful to identify agents that inhibit the activity of *M. tuberculosis* DNA synthesis enzyme ribonucleotide reductase or topoisomerase I.

The second host cells contain either a functioning endogenous DNA synthesis enzyme or a homologous non-*M. tuberculosis* DNA synthesis enzyme.

Separate cultures of the first host cells and the second host cells are contacted with test compounds to determine whether they effect the *M. tuberculosis* DNA synthesis enzyme. In some embodiments of the invention, the preferred concentration of test compound is between 1 nM and 1 mM. A preferred concentration is 10 nM to 0.5 mM. A preferred concentration is 0.1 μM to 250 μM. A preferred concentration is 1 μM to 100 μM. A preferred concentration is 10 μM to 100 μM. In some preferred embodiments, it is desirable to use a series of dilutions of test compounds.

After contacting the cultures of host cells with the test compound, the level of DNA synthesis in the culture of first host cells and the level of DNA synthesis in culture of second host cells is measured. The level of DNA synthesis in a culture of host cells can be measured by a number of well known and routine methods. For example, the cells may be cultured with radiolabelled nucleotides. If DNA synthesis is occurring, the radiolabelled nucleotides will be used incorporated into the synthesized DNA. The unincorporated radiolabelled nucleotides can be removed with the culture medium and the level of incorporated radiolabelled nucleotides in DNA can be measured routinely such as by using a scintillation counter. Another example of measuring DNA synthesis is to measure the amount of host cells in the culture. DNA synthesis is essential to cell replication. The number of cells present in a culture is indicative of the level of cell replication. If DNA synthesis is inhibited, cell replication is inhibited and therefore the number of cells present will be reduced as compared to the number of cells present if DNA synthesis is not inhibited. Preferred methods include those which assess DNA synthesis as a function of cell growth. Complemented and control cultures of E. coli are cultured in 96 well plates. After incubation time in the presence of test compound, cell growth is determined using a spectrophotometer. The cell density of complemented and control cultures of E. coli are compared. As an additional control, complemented and control cultures of E. coli are grown in the absence of test compound and cell growth is measured. In some embodiments, "diffusion disk" assays are performed using disks that contain test compounds. The disks are placed on lawns of complemented and control cultures of E. coli and any differences in cell growth of cells surrounding the disks is observed.

The methods of the invention are useful to identify selective inhibitors of M. tuberculosis DNA synthesis enzymes. Inhibitors are useful as anti-M. tuberculosis agents. Kits are provided for screening compounds for identifying selective inhibitors of M. tuberculosis DNA synthesis enzymes.

The present invention relates to substantially pure M. tuberculosis R2 proteins R2-1 and R2-2.

The present invention relates to substantially pure M. tuberculosis R2 protein R2-2 having the amino acid sequence of SEQ ID NO:2 and to substantially pure M. tuberculosis R2 protein R2-1 having the amino acid sequence of SEQ ID NO:6.

The present invention relates to nucleic acid molecules that encode M. tuberculosis R2 proteins R2-1 and R2-2.

The present invention relates to nucleic acid molecules encoding M. tuberculosis R2 protein R2-2 that consists of SEQ ID NO:1 and to nucleic acid molecules encoding M. tuberculosis R2 protein R2-1 that consists of SEQ ID NO:5.

The present invention relates to recombinant expression vectors that comprise a nucleic acid sequence that encodes an M. tuberculosis R2 protein.

The present invention relates to host cells that comprise recombinant expression vectors that encode an M. tuberculosis R2 protein.

The present invention relates to methods of making recombinant M. tuberculosis R2 protein comprising the steps of culturing host cells in medium that comprise recombinant expression vectors that encode an M. tuberculosis R2 protein and purifying the R2 protein from the cultured cells and medium.

The present invention relates to fragments of nucleic acid molecules with sequences encoding an M. tuberculosis R2 protein that have at least 10 nucleotides.

The present invention relates to oligonucleotide molecules that comprise a nucleotide sequence complimentary to a nucleotide sequence of at least 10 nucleotides of SEQ ID NO:1 or SEQ ID NO:5.

The present invention relates to isolated antibodies which bind to an epitope on SEQ ID NO:2 or SEQ ID NO:6.

The present invention provides in vitro assays to identify inhibitors of M. tuberculosis ribonucleotide reductase. The method comprises the steps of combining isolated R1 protein, an isolated R2 protein, a substrate and a test compound. The R1 and R2 proteins complex to form a functional ribonucleotide reductase enzyme. According to the invention, the R1 and R2 proteins are produced by recombinant means and are free from all other M. tuberculosis proteins. As used herein, the term "recombinantly produced R1 protein and recombinantly produced R2 protein" is meant to refer to R1 and R2 proteins that are produced by recombinant means and that are free from all other M. tuberculosis proteins. The substrate is a ribonucleotide, specifically a ribonucleotide diphosphate. It is processed by ribonucleotide reductase into deoxyribonucleotide, specifically a ribonucleotide diphosphate. In preferred embodiments, ribonucleotides are selected from the group consisting of ADP, CDP, GDP, TDP and UDP, which are processed into dADP, dCDP, dGDP, dTDP and dUDP. The level of processing of the ribonucleotide by the ribonucleotide reductase complex into a deoxyribonucleotide is measured either by measuring the amount of ribonucleotide remaining or by measuring the amount of deoxyribonucleotide produced. The amount of ribonucleotide remaining or the amount of deoxyribonucleotide produced is compared to the amount of ribonucleotide remaining or the amount of deoxyribonucleotide produced when the ribonucleotide is processed into a deoxyribonucleotide by the R1 and R2 proteins in the absence of the test compound. If the level of processing of the ribonucleotide is reduced in the presence of said test compound, the test compound can be an inhibitor of ribonucleotide reductase activity. Inhibitors are useful as anti-M. tuberculosis agents. In preferred embodiments, the ribonucleotide is labelled, preferably radiolabelled and the processing of the ribonucleotide is determined by measuring the amount of deoxyribonucleotide produced. The unprocessed ribonucleotide can be separated from the deoxyribonucleotide using a phenylboronate agarose gel column.

Kits are provided for screening compounds for identifying inhibitors of M. tuberculosis ribonucleotide reductase. The kits comprise a container with R1 and R2 and directions for performing the assay. Optionally, R1 and R2 may be provided in separate containers. Optionally, a container with the ribonucleotide may be provided. Optionally, means to measure the presence and/or amount ribonucleotide may be provided. Optionally, means to measure the presence and/or amount deoxyribonucleotide may be provided. Optionally, positive and/or negative controls may be provided. Examples of positive controls include known inhibitors such as neutralizing anti-R1 antibodies or neutralizing anti-R2 antibodies. Known quantities of ribonucleotide or deoxyribonucleotide may be provided as controls for measuring such reagents and comparing to results from test assays.

The present invention relates to substantially pure M. tuberculosis topoisomerase I protein.

The present invention relates to substantially pure M. tuberculosis topoisomerase I protein having the amino acid sequence of SEQ ID NO:4.

The present invention relates to nucleic acid molecules that encode M. tuberculosis topoisomerase I protein.

The present invention relates to nucleic acid molecules encoding M. tuberculosis topoisomerase I protein that consists of SEQ ID NO:3.

The present invention relates to recombinant expression vectors that comprise a nucleic acid sequence that encodes *M. tuberculosis* topoisomerase I protein.

The present invention relates to host cells that comprise recombinant expression vectors that encode *M. tuberculosis* topoisomerase I protein.

The present invention relates to methods of making recombinant *M. tuberculosis* topoisomerase I protein comprising the steps of culturing host cells in medium that comprise recombinant expression vectors that encode *M. tuberculosis* topoisomerase I protein and purifying the topoisomerase I protein from the cultured cells and medium.

The present invention relates to fragments of nucleic acid molecules with sequences encoding *M. tuberculosis* topoisomerase I protein that have at least 10 nucleotides.

The present invention relates to oligonucleotide molecules that comprise a nucleotide sequence complimentary to a nucleotide sequence of at least 10 nucleotides of SEQ ID NO:3.

The present invention relates to isolated antibodies which bind to an epitope on SEQ ID NO:4.

DETAILED DESCRIPTION OF PREFERRED EMBODIMENTS OF THE INVENTION

As used herein, the terms "*M. tuberculosis* R2 protein" and "R2 protein" are used interchangably and meant to refer to the *M. tuberculosis* R2 protein R2-1 and the *M. tuberculosis* R2 protein R2-2. The cDNA encoding the R2-1 protein is disclosed in SEQ ID NO:5 and SEQ ID NO:6 contains the corresponding amino acid sequence. The cDNA encoding the R2-2 protein is disclosed in SEQ ID NO:1 and SEQ ID NO:2 contains the corresponding amino acid sequence.

A rate limiting step in DNA replication is the conversion of ribonucleotides to deoxyribonucleotides which is catalyzed by the allosterically regulated, two subunit enzyme, ribonucleotide reductase (RR). In accordance with some aspects of the present invention, this enzyme system has been cloned from *M. tuberculosis* (*M. tuberculosis*) and expressed and purified the *M. tuberculosis* recombinant enzyme in *E. coli*. In some aspects of the invention, a complementation system is provided in which the genes encoding *M. tuberculosis* ribonucleotide reductase are transferred into an *E. coli* host that is temperature sensitive (ts) for its own ribonucleotide reductase (nrd A and nrd B mutants) (Yale Depository, New Haven Conn.). In some aspects of the invention purification of large quantities of recombinant *M. tuberculosis* ribonucleotide reductase which can are active in vitro and can be used to identify inhibitors of *M. tuberculosis* activity.

Another enzyme involved in *M. tuberculosis* DNA synthesis is topoisomerase I. DNA topoisomerases are ubiquitous enzymes that control the topology of DNA and play an essential role in biological processes, such as replication, transcription and recombination. The topoisomerases have been classified into subfamilies based on shared catalytic mechanisms. Type 1 topoisomerases, that make single stranded break, include the prokaryotic and eukaryotic Topo I, prokaryotic and yeast Topo III. Type 2 topoisomerases, making double stranded breaks, include DNA gyrase (Topo II) and Topo IV. Type 1–5' DNA topoisomerases, mainly distributed in prokaryotic species, relax negatively supercoiled DNA by making transient single-stranded DNA breaks, passing another single-strand DNA through the nick site and thereby resealing the breaks, changing the linking number in steps of one. The catalytic mechanism of this type of topoisomerase is ATP independent and involves a covalent linkage between a tyrosine residue in the active site of the N-terminal domain of the enzyme and the 5' phosphoryl group of the cleaved DNA strand. The reaction requires magnesium, is inhibited by polyamines and is insensitive to camptothecin. Type 1–3' DNA topoisomerases, found predominantly in eukaryotic cells, is also ATP-independent and relaxes both positively and negatively supercoiled DNA. Members of this subfamily bind preferentially to double stranded DNA and cleave one of the DNA strands forming a protein-DNA covalent intermediate between a tyrosyl residue and 3'-phosphate at the break site. The active site tyrosine is located in the highly conserved carboxyl-terminal domain. The enzymatic activity can be inhibited by camptothecin and stimulated by polyamine. Prokaryotic Topo III, while similar to prokaryotic Topo I in amino acid sequence has a $k_{cat}$ almost an order of magnitude higher for decatenation than for relaxation of negative supercoils at 30° C.

In accordance with some aspects of the present invention, the *M. tuberculosis* topoisomerase I is inserted into expression vectors which are incorporated into *E. coli*. The *M. tuberculosis* topoisomerase I protein is expressed and purified as a recombinant enzyme from *E. coli*. Similarly, the *M. tuberculosis* topoisomerase I coding sequence can be used to complement *E. coli* mutants that are temperature sensitive for topoisomerase I activity. *E. coli* host cells that are temperature sensitive (ts) for endogenous ribonucleotide reductase (nrd A and nrd B mutants) can be readily obtained such as from the Yale Depository.

To screen compounds according to some of the methods of the present invention, the first host cells are *E. coli* that contain a temperature sensitive mutation for topoisomerase I or ribonucleotide reductase and are complemented with functional *M. tuberculosis* topoisomerase I or *M. tuberculosis* ribonucleotide reductase (both R1 and an R2 protein), respectively. The second host cells either contain a functional endogenous topoisomerase I or ribonucleotide reductase, respectively, or they are complemented with a non-*M. tuberculosis* topoisomerase I or non-*M. tuberculosis* ribonucleotide reductase, respectively. The groups are contacted with test compounds and either uptake by the host cells of radiolabelled nucleotides added to the culture medium, or the survivability of each of the two groups of host cells is observed. If a test compound leads to the reduction in nucleotide uptake host cells complemented with *M. tuberculosis* topoisomerase I or ribonucleotide reductase, or the death of the host cells complemented with *M. tuberculosis* topoisomerase I or ribonucleotide reductase, but not to the reduction of nucleotide uptake or cell death of those with endogenous or non-*M. tuberculosis* topoisomerase I or ribonucleotide reductase, the compound is a selective inhibitor of *M. tuberculosis* topoisomerase I or ribonucleotide reductase, respectively.

Kits are provided which comprise containers with host cells or reagents necessary to produce host cells and/or screen test compounds. In additions, kits comprise instructions for performing such methods. Host cells include complemented host cells or those mutants which can be complemented. Reagents include expression vectors including *M. tuberculosis* topoisomerase I or ribonucleotide reductase genes.

The present invention provides cloned genes that encodes *M. tuberculosis* DNA synthesis enzymes topoisomerase I protein and the small subunit (R2) of ribonucleotide reductase (RR). The discovery of these *M. tuberculosis* genes and the proteins that they encode provides the means to design and discover specific inhibitors of *M. tuberculosis* topoisomerase I protein or ribonucleotide reductase.

As used herein the terms "specific inhibitor of *M. tuberculosis* topoisomerase I" and "selective inhibitor of *M. tuberculosis* topoisomerase I" are used interchangeably and are meant to refer to compounds that inhibit DNA synthesis in *M. tuberculosis* by inhibiting of activity of *M. tuberculosis* topoisomerase I. The compounds do not inhibit non-*M. tuberculosis* species topoisomerase I activity. Inhibition of *M. tuberculosis* topoisomerase I activity essentially leads to cell death due to the cells inability to replicate in the absence of the ability to synthesize DNA. Compounds that selectively inhibit *M. tuberculosis* topoisomerase I activity are those which inhibit *M. tuberculosis* topoisomerase I activity but not the activity of non-*M. tuberculosis* topoisomerase I enzyme.

As used herein the terms "specific inhibitor of *M. tuberculosis* ribonucleotide reductase" and "selective inhibitor of *M. tuberculosis* ribonucleotide reductase" are used interchangeably and are meant to refer to compounds that inhibit DNA synthesis in *M. tuberculosis* through the inhibition of activity of *M. tuberculosis* ribonucleotide reductase enzyme. The compounds do not inhibit non-*M. tuberculosis* species ribonucleotide reductase activity. Inhibition of ribonucleotide reductase activity essentially leads to cell death due to the cells inability to replicate in the absence of the ability to synthesize DNA. Compounds that selectively inhibit *M. tuberculosis* ribonucleotide reductase activity are those which inhibit *M. tuberculosis* ribonucleotide reductase activity but not the activity of non-*M. tuberculosis* ribonucleotide reductase enzyme.

According to the present invention, the gene that encodes *M. tuberculosis* topoisomerase I protein or the genes that encode the subunits of ribonucleotide reductase enzyme, i.e. the large subunit (R1) and the small subunit (R2), may be used to produce recombinant microorganisms that are useful to screen compounds for specific inhibitors. Two R2 proteins, R2-1 and R2-2, have been identified.

A host organism deficient in endogenous topoisomerase I protein may be "complemented" with *M. tuberculosis* topoisomerase I, i.e. furnished with a functional copy of the *M. tuberculosis* topoisomerase I gene or cDNA. Expression of the nucleotide sequence that encodes *M. tuberculosis* topoisomerase I protein results in production of functional protein which functions in place of the missing or non-functional endogenous topoisomerase I.

Similarly, a host organism deficient in endogenous ribonucleotide reductase enzymes may be "complemented" with *M. tuberculosis* ribonucleotide reductase, i.e. furnished with a functional copies of the *M. tuberculosis* R1 and R2 genes or cDNAs. Expression of the nucleotide sequences that encode *M. tuberculosis* ribonucleotide reductase subunits results in production of functional ribonucleotide reductase enzyme which functions in place of the missing or non-functional endogenous ribonucleotide reductase.

Comparative studies can be performed to evaluate the effect that test compounds have on the hosts that are complemented with *M. tuberculosis* topoisomerase I or ribonucleotide reductase enzyme compared to the effect the same test compounds have on the hosts with functional endogenous topoisomerase I or ribonucleotide reductase, respectively. Comparisons between *M. tuberculosis* topoisomerase I- or ribonucleotide reductase-complemented hosts and hosts that are complemented with non-*M. tuberculosis* topoisomerase I or ribonucleotide reductase, respectively, can also be performed.

The methods of the invention are useful to identify selective inhibitors of *M. tuberculosis* topoisomerase I or ribonucleotide reductase. Inhibitors are useful as anti-*M. tuberculosis* agents. Kits are provided for screening compounds for identifying selective inhibitors of *M. tuberculosis* DNA synthesis enzymes including topoisomerase I and ribonucleotide reductase.

In addition to complementation assays, the present invention provides in vitro assays to identify inhibitors of *M. tuberculosis* ribonucleotide reductase. According to one aspect of the invention, a method of screening compounds is provided to identify inhibitors of *M. tuberculosis* ribonucleotide reductase. The method comprises the steps of combining isolated R1 protein, an isolated R2 protein, a substrate and a test compound under conditions in which the substrate would be processed by the R1 and R2 into a product in absence of said test compound. The R1 and R2 proteins complex to form a functional ribonucleotide reductase enzyme. The substrate is a ribonucleotide diphosphate that is processed by ribonucleotide reductase into a deoxyribonucleotide diphosphate. In preferred embodiments, ribonucleotides are selected from the group consisting of ADP, CDP, GDP, TDP and UDP, which are processed into dADP, dCDP, dGDP, dTDP and dUDP. The level of processing of the ribonucleotide by the ribonucleotide reductase complex into a deoxyribonucleotide is measured either by measuring the amount of ribonucleotide remaining or by measuring the amount of deoxyribonucleotide produced. The amount of ribonucleotide remaining or the amount of deoxyribonucleotide produced is compared to the amount of ribonucleotide remaining or the amount of deoxyribonucleotide produced when the ribonucleotide is processed into a deoxyribonucleotide by the R1 and R2 proteins in the absence of the test compound. If the level of processing of the ribonucleotide is reduced in the presence of said test compound, the test compound can be an inhibitor of ribonucleotide reductase activity. Inhibitors are useful as anti-*M. tuberculosis* agents. In preferred embodiments, the ribonucleotide is labelled, preferably radiolabelled and the processing of the ribonucleotide is determined by measuring the amount of deoxyribonucleotide produced. The unprocessed ribonucleotide can be separated from the deoxyribonucleotide using a phenylboronate agarose gel column. If the level of processing of the ribonucleotide is reduced in the presence of the test compound, the test compound can be an inhibitor of ribonucleotide reductase activity. Inhibitors are useful as anti-*M. tuberculosis* agents.

Kits are provided for screening compounds for identifying inhibitors of *M. tuberculosis* ribonucleotide reductase. The kits comprise a container with R1 and R2 and directions for performing the assay. Optionally, R1 and R2 may be provided in separate containers. Optionally, a container with the ribonucleotide may be provided. Optionally, means to measure the presence and/or amount ribonucleotide may be provided. Optionally, means to measure the presence of ribonucleotide may be provided. Optionally, means to measure the presence and/or amount of deoxyribonucleotide may be provided. Optionally, positive and/or negative controls may be provided. Examples of positive controls include known inhibitors such as neutralizing anti-R1 antibodies or neutralizing anti-R2 antibodies. Known quantities of ribonucleotide or deoxyribonucleotide may be provided as controls for measuring such reagents and comparing to results from test assays.

The nucleotide sequence that encodes an *M. tuberculosis* R2 protein allows for the production of complemented host cells which are deficient in functioning endogenous ribonucleotide reductase but which can synthesize DNA due to the presence of functional *M. tuberculosis* ribonucleotide reductase protein. In the host cell, the deficiency of functioning ribonucleotide reductase can be due to a deficiency in the functioning of R1 protein, R2 protein or both. In order for the ribonucleotide reductase deficient host cell to be complemented, both R1 protein and an R2 protein from *M. tuberculosis* must be provided. Accordingly, coding sequence for the *M. tuberculosis* R1 protein and R2 protein must be introduced into the host cells.

SEQ ID NO:24 encodes the R1 protein. In preparing gene constructs for complementation of deficient hosts, SEQ ID NO:24 and either SEQ ID NO:1 or SEQ ID NO:5 are introduced into a host cell and expressed. The coding sequences for R1 and R2 may be inserted into a single expression vector or separate expression vectors. The coding sequences must be operably linked to regulatory elements required for gene expression in the host. As controls, deficient host cells may be complemented with nucleotide sequences that encode a functional endogenous ribonucleotide reductase subunits or functional non-*M. tuberculosis* ribonucleotide reductase subunits, or the host cells may be maintained in conditions in which the endogenous ribonucleotide reductase is functional.

The nucleotide sequence that encodes *M. tuberculosis* R2-2 protein and that is disclosed herein as SEQ ID NO:1 allows for the production of pure *M. tuberculosis* R2-2 protein and the design of probes which specifically hybridize to nucleic acid molecules that encode *M. tuberculosis* R2-2 protein and antisense compounds to inhibit transcription of the gene that encodes *M. tuberculosis* R2-2 protein. The R2 protein may be combined with *M. tuberculosis* R1 protein to form an active ribonucleotide reductase enzyme complex.

The nucleotide sequence that encodes *M. tuberculosis* R2-1 protein and that is disclosed herein as SEQ ID NO:5 allows for the production of pure *M. tuberculosis* R2-1 protein and the design of probes which specifically hybridize to nucleic acid molecules that encode *M. tuberculosis* R2-1 protein and antisense compounds to inhibit transcription of the gene that encodes *M. tuberculosis* R2-1 protein. The R2 protein may be combined with *M. tuberculosis* R1 protein to form an active ribonucleotide reductase enzyme complex.

The nucleotide sequence that encodes *M. tuberculosis* topoisomerase I protein and that is disclosed herein as SEQ ID NO:3 allows for the production of complemented host cells which are deficient in functioning endogenous topoisomerase I but which can synthesize DNA due to the presence of functional *M. tuberculosis* topoisomerase I protein. In preparing gene constructs for complementation of deficient hosts, SEQ ID NO:3 is introduced into a host cell and expressed. SEQ ID NO:3 may be inserted into an expression vector in which the coding sequence is operably linked to regulatory elements required for gene expression in the host. As controls, deficient host cells may be complemented with a functional endogenous topoisomerase I, a functional non-*M. tuberculosis* topoisomerase I, or maintained in conditions in which the endogenous topoisomerase I is functional. The nucleotide sequence that encodes *M. tuberculosis* topoisomerase I protein and that is disclosed herein as SEQ ID NO:3 allows for the production of pure *M. tuberculosis* topoisomerase I protein and the design of probes which specifically hybridize to nucleic acid molecules that encode *M. tuberculosis* topoisomerase I protein and antisense compounds to inhibit transcription of the gene that encodes *M. tuberculosis* topoisomerase I protein.

The present invention provides a substantially purified *M. tuberculosis* R2 protein. The present invention provides substantially purified *M. tuberculosis* R2-2 protein which has the amino acid sequence consisting of SEQ ID NO:2. The present invention provides substantially purified *M. tuberculosis* R2-1 protein which has the amino acid sequence consisting of SEQ ID NO:6. An *M. tuberculosis* R2 protein can be isolated from natural sources or produced by recombinant DNA methods.

The present invention provides substantially purified *M. tuberculosis* topoisomerase I protein. The present invention provides substantially purified *M. tuberculosis* topoisomerase I protein which has the amino acid sequence consisting of SEQ ID NO:4. *M. tuberculosis* topoisomerase I protein can be isolated from natural sources or produced by recombinant DNA methods.

Antibodies that specifically bind to an *M. tuberculosis* R2 protein or topoisomerase I protein are provided. Such antibodies are specific inhibitors of *M. tuberculosis* ribonucleotide reductase and topoisomerase I protein, respectively. Such antibodies may be used in methods of isolating a pure *M. tuberculosis* R2 protein and topoisomerase I protein, respectively. Likewise, such antibodies may be used in methods of inhibiting *M. tuberculosis* ribonucleotide reductase enzyme activity and topoisomerase I protein activity, respectively.

The antibodies may be used to purify the protein from natural sources using well known techniques and readily available starting materials. Anti-*M. tuberculosis* R2 antibodies may be used to purify the *M. tuberculosis* R2 protein that they are specific for from natural sources or from material present when producing the protein by recombinant DNA methodology. The present invention relates to antibodies that bind to an epitope which is specific for *M. tuberculosis* R2 protein. Anti-*M. tuberculosis* topoisomerase I antibodies may be used to purify *M. tuberculosis* topoisomerase I protein from natural sources or from material present when producing the protein by recombinant DNA methodology. The present invention relates to antibodies that bind to an epitope which is specific for *M. tuberculosis* topoisomerase I protein.

As used herein, the term "antibody" is meant to refer to complete, intact antibodies, and Fab fragments and F(ab)$_2$ fragments thereof. Complete, intact antibodies include monoclonal antibodies such as murine monoclonal antibodies, chimeric antibodies and humanized antibodies.

The production of antibodies and the protein structures of complete, intact antibodies, Fab fragments and F(ab)$_2$ fragments and the organization of the genetic sequences that encode such molecules are well known and are described, for example, in Harlow, E. and D. Lane (1988) *ANTIBODIES: A Laboratory Manual*, Cold Spring Harbor Laboratory, Cold Spring Harbor, N.Y., which is incorporated herein by reference. Briefly, for example, the *M. tuberculosis* protein, or an immunogenic fragment thereof is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to *M. tuberculosis* protein that was injected into the mouse, the hybridoma which produces them is cultured to produce a continuous supply of antibodies.

Using standard techniques and readily available starting materials, a nucleic acid molecule that encodes an *M. tuberculosis* R2 protein may be isolated from a cDNA library, using probes which are designed using the nucleotide sequence information disclosed in SEQ ID NO:1 or SEQ ID NO:5. Likewise, a nucleic acid molecule that encodes *M. tuberculosis* topoisomerase I protein may be isolated from a cDNA library, using probes which are designed using the nucleotide sequence information disclosed in SEQ ID NO:3.

One aspect of the present invention relates to an isolated nucleic acid molecule that comprises a nucleotide sequence that encodes an *M. tuberculosis* R2 protein. In some embodiments, the nucleic acid molecules consist of a nucleotide sequence that encodes an *M. tuberculosis* R2 protein. In some embodiments, the nucleic acid molecules comprise the nucleotide sequence that consists of the coding sequence in SEQ ID NO:1. In some embodiments, the nucleic acid molecules consist of the nucleotide sequence set forth in SEQ ID NO:1. In some embodiments, the nucleic acid molecules comprise the nucleotide sequence that consists of the coding sequence in SEQ ID NO:5. In some embodiments, the nucleic acid molecules consist of the nucleotide sequence set forth in SEQ ID NO:5. The isolated nucleic acid molecules of the invention are useful to prepare constructs and recombinant expression systems for preparing isolated *M. tuberculosis* R2 protein.

One aspect of the present invention relates to an isolated nucleic acid molecule that comprises a nucleotide sequence that encodes *M. tuberculosis* topoisomerase I protein. In some embodiments, the nucleic acid molecules consist of a nucleotide sequence that encodes *M. tuberculosis* topoisomerase I protein. In some embodiments, the nucleic acid molecules comprise the nucleotide sequence that consists of the coding sequence in SEQ ID NO:3. In some embodiments, the nucleic acid molecules consist of the nucleotide sequence set forth in SEQ ID NO:3. The isolated nucleic acid molecules of the invention are useful to prepare constructs and recombinant expression systems for preparing isolated *M. tuberculosis* topoisomerase I protein.

A genomic or cDNA library may be generated by well known techniques. Clones of an *M. tuberculosis* R2 protein are identified using probes that comprise at least a portion of the nucleotide sequence disclosed in SEQ ID NO:1 or SEQ ID NO:5, respectively. Clones of the *M. tuberculosis* topoisomerase I protein are identified using probes that comprise at least a portion of the nucleotide sequence disclosed in SEQ ID NO:3. The probes have at least 16 nucleotides, preferably 24 nucleotides. The probes are used to screen the genomic or cDNA libraries using standard hybridization techniques.

The present invention relates to isolated nucleic acid molecules that comprises at least 10 nucleotides of a nucleotide sequence identical or complementary to a fragment of SEQ ID NO:1, SEQ ID NO:3 or SEQ ID NO:5.

In some embodiments, the isolated nucleic acid molecules consist of a nucleotide sequence identical or complementary to a fragment of SEQ ID NO:1 which is at least 10 nucleotides. In some embodiments, the isolated nucleic acid molecules comprise or consist of a nucleotide sequence identical or complementary to a fragment of SEQ ID NO:1 which is 15–150 nucleotides. In some embodiments, the isolated nucleic acid molecules comprise or consist of a nucleotide sequence identical or complementary to a fragment of SEQ ID NO:1 which is 15–30 nucleotides.

In some embodiments, the isolated nucleic acid molecules consist of a nucleotide sequence identical or complementary to a fragment of SEQ ID NO:5 which is at least 10 nucleotides. In some embodiments, the isolated nucleic acid molecules comprise or consist of a nucleotide sequence identical or complementary to a fragment of SEQ ID NO:5 which is 15–150 nucleotides. In some embodiments, the isolated nucleic acid molecules comprise or consist of a nucleotide sequence identical or complementary to a fragment of SEQ ID NO:5 which is 15–30 nucleotides.

In some embodiments, the isolated nucleic acid molecules consist of a nucleotide sequence identical or complementary to a fragment of SEQ ID NO:3 which is at least 10 nucleotides. In some embodiments, the isolated nucleic acid molecules comprise or consist of a nucleotide sequence identical or complementary to a fragment of SEQ ID NO:3 which is 15–150 nucleotides. In some embodiments, the isolated nucleic acid molecules comprise or consist of a nucleotide sequence identical or complementary to a fragment of SEQ ID NO:3 which is 15–30 nucleotides.

Isolated nucleic acid molecules that comprise or consist of a nucleotide sequence identical or complementary to a fragment of SEQ ID NO:1 which is at least 10 nucleotides are useful as probes for identifying genes and cDNA sequences that encodes *M. tuberculosis* R2 protein R2-2, PCR primers for amplifying genes and cDNA that encodes *M. tuberculosis* R2 protein R2-2, and antisense molecules for inhibiting transcription and translation of genes and cDNA, respectively, which encode *M. tuberculosis* R2 protein R2-2.

The nucleotide sequence in SEQ ID NO:1 may be used to design probes, primers and complimentary molecules which specifically hybridize to the unique nucleotide sequences of *M. tuberculosis* R2 protein. Probes, primers and complimentary molecules which specifically hybridize to nucleotide sequence that encodes *M. tuberculosis* R2 protein may be designed routinely by those having ordinary skill in the art.

Isolated nucleic acid molecules that comprise or consist of a nucleotide sequence identical or complementary to a fragment of SEQ ID NO:5 which is at least 10 nucleotides are useful as probes for identifying genes and cDNA sequences that encodes *M. tuberculosis* R2 protein R2-1, PCR primers for amplifying genes and cDNA that encodes *M. tuberculosis* R2 protein R2-1, and antisense molecules for inhibiting transcription and translation of genes and cDNA, respectively, which encode *M. tuberculosis* R2 protein R2-1.

The nucleotide sequence in SEQ ID NO:5 may be used to design probes, primers and complimentary molecules which specifically hybridize to the unique nucleotide sequences of *M. tuberculosis* R2 protein R2-1. Probes, primers and complimentary molecules which specifically hybridize to nucleotide sequence that encodes *M. tuberculosis* R2 protein R2-1 may be designed routinely by those having ordinary skill in the art.

Isolated nucleic acid molecules that comprise or consist of a nucleotide sequence identical or complementary to a fragment of SEQ ID NO:3 which is at least 10 nucleotides are useful as probes for identifying genes and cDNA sequences that encodes *M. tuberculosis* topoisomerase I protein, PCR primers for amplifying genes and cDNA that encodes *M. tuberculosis* topoisomerase I protein, and antisense molecules for inhibiting transcription and translation of genes and cDNA, respectively, which encode *M. tuberculosis* topoisomerase I protein.

The nucleotide sequence in SEQ ID NO:3 may be used to design probes, primers and complimentary molecules which specifically hybridize to the unique nucleotide sequences of *M. tuberculosis* topoisomerase I protein. Probes, primers and complimentary molecules which specifically hybridize to nucleotide sequence that encodes *M. tuberculosis* topoisomerase I protein may be designed routinely by those having ordinary skill in the art.

The present invention also includes labelled oligonucleotides which are useful as probes for performing oligonucleotide hybridization methods to identify clones that encode an *M. tuberculosis* R2 protein or topoisomerase I protein. Accordingly, the present invention includes probes that can be labelled and hybridized to unique nucleotide sequences of nucleic acid molecules that encode *M. tuberculosis* R2 protein or topoisomerase I protein. The labelled probes of the present invention are labelled with radiolabelled nucleotides or are otherwise detectable by readily available non-radioactive detection systems. In some preferred embodiments, probes comprise oligonucleotides consisting of between 10 and 100 nucleotides. In some preferred, probes comprise oligonucleotides consisting of between 10 and 50 nucleotides. In some preferred, probes comprise oligonucleotides consisting of between 12 and 20 nucleotides. The probes preferably contain nucleotide sequence completely identical or complementary to a fragment of a unique nucleotide sequences of nucleic acid molecules that encode an *M. tuberculosis* R2 protein or topoisomerase I protein.

PCR technology is practiced routinely by those having ordinary skill in the art and its uses in diagnostics are well known and accepted. Methods for practicing PCR technology are disclosed in "PCR Protocols: A Guide to Methods and Applications", Innis, M. A., et al. Eds. Academic Press, Inc. San Diego, Calif. (1990), which is incorporated herein by reference. Applications of PCR technology are disclosed in "Polymerase Chain Reaction" Erlich, H. A., et al., Eds. Cold Spring Harbor Press, Cold Spring Harbor, N.Y. (1989), which is incorporated herein by reference. Some simple rules aid in the design of efficient primers. Typical primers are 18–28 nucleotides in length having 50% to 60% g+c composition. The entire primer is preferably complementary to the sequence it must hybridize to. Preferably, primers generate PCR products 100 basepairs to 2000 base pairs. However, it is possible to generate products of 50 base pairs to up to 10 kb and more.

PCR technology allows for the rapid generation of multiple copies of nucleotide sequences by providing 5' and 3' primers that hybridize to sequences present in a nucleic acid molecule, and further providing free nucleotides and an enzyme which fills in the complementary bases to the nucleotide sequence between the primers with the free nucleotides to produce a complementary strand of DNA. The enzyme will fill in the complementary sequences adjacent to the primers. If both the 5' primer and 3' primer hybridize to nucleotide sequences on the complementary strands of the same fragment of nucleic acid, exponential amplification of a specific double-stranded product results. If only a single primer hybridizes to the nucleic acid molecule, linear amplification produces single-stranded products of variable length.

One having ordinary skill in the art can isolate the nucleic acid molecule that encodes *M. tuberculosis* ribonucleotide reductase protein or *M. tuberculosis* topoisomerase I protein and insert it into an expression vector using standard techniques and readily available starting materials.

The present invention relates to a recombinant expression vector that comprises a nucleotide sequence that encodes *M. tuberculosis* R2 protein R2-2 that comprises the amino acid sequence of SEQ ID NO:2.

The present invention relates to a recombinant expression vector that comprises a nucleotide sequence that encodes *M. tuberculosis* R2 protein R2-1 that comprises the amino acid sequence of SEQ ID NO:6.

The present invention relates to a recombinant expression vector that comprises a nucleotide sequence that encodes *M. tuberculosis* topoisomerase I protein that comprises the amino acid sequence of SEQ ID NO:4.

As used herein, the term "recombinant expression vector" is meant to refer to a plasmid, phage, viral particle or other vector which, when introduced into an appropriate host, contains the necessary genetic elements to direct expression of the coding sequence that encodes *M. tuberculosis* R2 or topoisomerase I protein. The coding sequence is operably linked to the necessary regulatory sequences. Expression vectors are well known and readily available. Examples of expression vectors include plasmids, phages, viral vectors and other nucleic acid molecules or nucleic acid molecule containing vehicles useful to transform host cells and facilitate expression of coding sequences.

In some embodiments, the recombinant expression vector comprises the nucleotide sequence set forth in SEQ ID NO:1. The recombinant expression vectors of the invention are useful for transforming hosts to prepare recombinant expression systems for preparing the *M. tuberculosis* R2-2 protein.

In some embodiments, the recombinant expression vector comprises the nucleotide sequence set forth in SEQ ID NO:5. The recombinant expression vectors of the invention are useful for transforming hosts to prepare recombinant expression systems for preparing the *M. tuberculosis* R2-1 protein.

In some embodiments, the recombinant expression vector comprises the nucleotide sequence set forth in SEQ ID NO:3. The recombinant expression vectors of the invention are useful for transforming hosts to prepare recombinant expression systems for preparing the *M. tuberculosis* topoisomerase I protein.

The present invention relates to a host cell that comprises the recombinant expression vector that includes a nucleotide sequence that encodes *M. tuberculosis* R2 protein R2-2 having SEQ ID NO:2. In some embodiments, the host cell comprises a recombinant expression vector that comprises SEQ ID NO:1.

The present invention relates to a host cell that comprises the recombinant expression vector that includes a nucleotide sequence that encodes *M. tuberculosis* R2 protein R2-1 having SEQ ID NO:6. In some embodiments, the host cell comprises a recombinant expression vector that comprises SEQ ID NO:5.

The present invention relates to a host cell that comprises the recombinant expression vector that includes a nucleotide sequence that encodes *M. tuberculosis* topoisomerase I protein having SEQ ID NO:4. In some embodiments, the host cell comprises a recombinant expression vector that comprises SEQ ID NO:3.

Host cells for use in well known recombinant expression systems for production of proteins are well known and readily available. Examples of host cells include bacteria cells such as *E. coli*, yeast cells such as *S. cerevisiae*, insect cells such as *S. frugiperda*, non-human mammalian tissue culture cells chinese hamster ovary (CHO) cells and human tissue culture cells such as HeLa cells.

The present invention relates to a transgenic, non-human mammal that comprises the recombinant expression vector that includes a nucleic acid sequence that encodes an *M. tuberculosis* R2 protein or the *M. tuberculosis* topoisomerase I protein. Transgenic, non-human mammals useful to produce recombinant proteins are well known as are the expression vectors necessary and the techniques for generating transgenic animals. Generally, the transgenic animal comprises a recombinant expression vector in which the nucleotide sequence that encodes the M. tuberculosis protein operably linked to a mammary cell specific promoter whereby the coding sequence is only expressed in mammary cells and the recombinant protein so expressed is recovered from the animal's milk. In some embodiments, the coding sequence that encodes M. tuberculosis R2 protein R2-2 is SEQ ID NO:1. In some embodiments, the coding sequence that encodes M. tuberculosis R2 protein R2-1 is SEQ ID NO:5. In some embodiments, the coding sequence that encodes M. tuberculosis topoisomerase 1 protein is SEQ ID NO:3.

In some embodiments, for example, one having ordinary skill in the art can, using well known techniques, insert such DNA molecules into a commercially available expression vector for use in well known expression systems. For example, the commercially available plasmid pSE420 (Invitrogen, San Diego, Calif.) may be used for production of the M. tuberculosis protein in E. coli. The commercially available plasmid pYES2 (Invitrogen, San Diego, Calif.) may, for example, be used for production in S. cerevisiae strains of yeast. The commercially available MAXBAC™ complete baculovirus expression system (Invitrogen, San Diego, Calif.) may, for example, be used for production in insect cells. The commercially available plasmid pcDNA I (Invitrogen, San Diego, Calif.) may, for example, be used for production in mammalian cells such as CHO cells. One having ordinary skill in the art can use these commercial expression vectors and systems or others to produce M. tuberculosis proteins using routine techniques and readily available starting materials. (See e.g., Sambrook et al., *Molecular Cloning a Laboratory Manual*, Second Ed. Cold Spring Harbor Press (1989), which is incorporated herein by reference.) Thus, the desired proteins can be prepared in both prokaryotic and eukaryotic systems, resulting in a spectrum of processed forms of the protein.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts. See e.g., Sambrook et al., *Molecular Cloning a Laboratory Manual*, Second Ed. Cold Spring Harbor Press (1989).

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein.

Commonly used eukaryotic systems include, but is not limited to, yeast, fungal cells, insect cells, mammalian cells, avian cells, and cells of higher plants. Suitable promoters are available which are compatible and operable for use in each of these host types as well as are termination sequences and enhancers, e.g. the baculovirus polyhedron promoter. As above, promoters can be either constitutive or inducible. For example, in mammalian systems, the mouse metallothionein promoter can be induced by the addition of heavy metal ions.

The particulars for the construction of expression systems suitable for desired hosts are known to those in the art. Briefly, for recombinant production of the protein, the DNA encoding the polypeptide is suitably ligated into the expression vector of choice. The DNA is operably linked to all regulatory elements which are necessary for expression of the DNA in the selected host. One having ordinary skill in the art can, using well known techniques, prepare expression vectors for recombinant production of the polypeptide.

The expression vector including the DNA that encodes an M. tuberculosis R2 or topoisomerase I protein is used to transform the compatible host which is then cultured and maintained under conditions wherein expression of the foreign DNA takes place. The protein of the present invention thus produced is recovered from the culture, either by lysing the cells or from the culture medium as appropriate and known to those in the art. One having ordinary skill in the art can, using well known techniques, isolate the M. tuberculosis R2 or topoisomerase I protein that is produced using such expression systems. The methods of purifying M. tuberculosis proteins from natural sources using antibodies which specifically bind to M. tuberculosis R2 or topoisomerase I protein as described above, may be equally applied to purifying M. tuberculosis protein produced by recombinant DNA methodology.

Examples of genetic constructs include the M. tuberculosis protein coding sequence operably linked to a promoter that is functional in the cell line into which the constructs are transfected. Examples of constitutive promoters include promoters from cytomegalovirus or SV40. Examples of inducible promoters include mouse mammary leukemia virus or metallothionein promoters. Those having ordinary skill in the art can readily produce genetic constructs useful for transfecting with cells with DNA that encodes M. tuberculosis R2 or topoisomerase I protein from readily available starting materials.

In some embodiments of the invention, transgenic non-human animals are generated. The transgenic animals according to the invention contain coding sequences that encodes either an M. tuberculosis R2 or topoisomerase I protein under the regulatory control of a mammary specific promoter. One having ordinary skill in the art using standard techniques, such as those taught in U.S. Pat. No. 4,873,191 issued Oct. 10, 1989 to Wagner and U.S. Pat. No. 4,736,866 issued Apr. 12, 1988 to Leder, both of which are incorporated herein by reference, can produce transgenic animals which produce the M. tuberculosis protein. Preferred animals are goats and rodents, particularly rats and mice.

In addition to producing these proteins by recombinant techniques, automated peptide synthesizers may also be employed to produce an M. tuberculosis R2 protein or M. tuberculosis topoisomerase I protein.

EXAMPLES

Example 1

Ribonucleotide reductase (RR) of the Class I form is a cell cycle regulated, two subunit, oxygen and iron dependent, radical mediated, allosteric enzyme that catalyzes the reduction of nucleoside diphosphates to deoxynucleoside diphosphates. This enzymatic activity is regulated at the protein level by 1) subunit interaction, 2) formation and maintenance of an $\mu$-oxo bridged iron (III)/tyrosyl radical redox center, and 3) positive and negative nucleotide allosteric effectors. There are additional regulatory features at the level of transcription, translation and post-translational modifications. Given its central role in the cell cycle, human ribonucleotide reductase is a well recognized target in the design of cancer chemotherapeutic agents. Furthermore, ribonucleotide reductase is gaining wide acceptance as a target for antivirals and antiparasitic chemotherapy.

Inhibition of ribonucleotide reductase in a variety of mycobacterial species has been reported to substantially alter the growth patterns of the organisms. Studies in the 1960s and 1970s showed that *M. smegmatis*, cultured in iron depleted media, displayed elongated morphology with decreased DNA synthesis and increased activity of DNA repair enzymes. When grown in the presence of 200 μg/ml of the radical scavenger hydroxyurea, growth of *M. smegmatic* was completely inhibited. At lower concentrations the organisms contained a decreased DNA/protein ratio with an increase in DNA polymerase and ATP-dependent DNAase activities as measured in crude extracts. Heterocyclic hydrazone inhibitors of ribonucleotide reductase have been reported to have minimum inhibitory concentrations against the virulent H37Rv strain of *M. tuberculosis* in the range of 40–80 μM.

Both subunits of ribonucleotide reductase have been cloned from a number of species including mammals, clam, yeast, bacteria, viruses and protozoa. Most of the biochemical characterization has been carried out on the *E. coli* or the mammalian species. However, recent work and work on *E. coli* and *Salmonella typhimurium* ribonucleotide reductase has important consequences for the relevance of the *M. tuberculosis* work.

*S. typhimurium* contains a ribonucleotide reductase system highly related to that encoded by the nrdA (large subunit) and nrdB (small subunit) genes found in *E. coli*, with 96.5% and 98.4% homology to the R1 and R2 subunits respectively. However, both *S. typhimurium* and *E. coli* contain a second set of chromosomal genes, nrdE and nrdF, that encode a ribonucleotide reductase that is not expressed under normal growth conditions. When purified and analyzed using a recombinant expression plasmid system, nrdE/nrdF has properties similar to those of the nrdA/nrdB systems, yet there are important differences in the allosteric effectors of the enzyme, in the character of the Fe/tyrosyl radical and in the R1-R2 subunit interaction surfaces. dATP is a positive allosteric activator up to 1 mM for the nrdE/nrdF system whereas dATP activates the nrdA/nrdB system only up to 1 uM and is negative effector at higher concentrations. ATP, dTTP, dGTP are activators of the nrdA/nrdB system but show only minimal activation of the nrdE/nrdF system. The EPR signal arising from the radical is more like the photosystem II signal that the ribonucleotide reductase signal. The C-terminal tail of the nrdF encoded small subunit is different from the C-terminal tail of the nrdB encoded small subunit. The interaction between subunits is dependent on the recognition of specific residues found at the C-terminal tail of R2 and residues in the R1 structure. Therefore, there is no complementation between a nrdE large subunit and a nrdB small subunit.

Given that *E. coli, Salmonella typhimurium*, and yeast contain genes encoding one or both ribonucleotide reductase subunits that are not expressed except under very unusual circumstances, and that mammalian cells possibly contain ribonucleotide reductase pseudogenes, active ribonucleotide reductase enzyme was purified from the Erdman strain of *M. tuberculosis* and the gene encoding the large subunit was cloned using information from the amino acid sequence. This strategy ensured that the genes so isolated would encode the actively transcribed and translated message.

*M. tuberculosis* R1 unexpectedly represents a nrdE-type R1. The gene encoding the small subunit has been cloned utilizing PCR primers homologous to the sequence of nrdF from Salmonella. In order to investigate the possibility that *M. tuberculosis* contains a non-coding nrdA/nrdB-type ribonucleotide reductase, extensive PCR experiments were carried out using a wide variety of primers. No sequences homologous to a nrdA/nrdB system could be found even at low stringency. Southern blots using *E. coli* nrdA and nrdB genes as probes did not reveal any positive bands. Furthermore, Western blots of *M. tuberculosis* extracts developed with anti-*E. coli* nrdA R1 and anti-*E. coli* nrdB R2 antibodies showed no cross reaction.

Two complete *M. tuberculosis* R2 genes, R2-1 and R2-2, were isolated by PCR amplification of conserved regions followed by screening of size selected *M. tuberculosis* libraries. Alignment of the *M. tuberculosis* R2 polypeptides encoded by the two genes with *S. typhimurium* human and *E. coli* R2 indicated that both of the *M. tuberculosis* R2 proteins contains the active site tyrosine and the iron binding residues corresponding to Asp84, Glu115, His118, Glu204, Glu238 and His241 in *E. coli* R2. The C termini, as expected, was different from that of human and *E. coli* R2.

Both *M. tuberculosis* R2-1 and R2-2 were cloned and expressed in *E. coli. M. tuberculosis* R2-1 was insoluble and biochemically inactive. *M. tuberculosis* R2-2 yielded soluble, biochemically active recombinant protein.

The recombinant *M. tuberculosis* R2, derived from R2-2, has now been purified to greater than 90% as estimated by SDS-PAGE with a yield of more than 20 mg/liter of culture. The purified recombinant R2 has a typical tyrosine radical absorbance at 408 nm which was abolished when the sample was treated with 15 mM of hydroxyurea for 10 min. The activity of the recombinant *M. tuberculosis* R2 was determined by the rate of dCDP production in the presence of recombinant *M. tuberculosis* R1. The specific activity of R2 was 200 nmol/mg protein/min when assayed in the presence of excess R1 and DTT as reductant, comparable with that of mouse R2. The reduction of CDP requires ATP as activator with an optimum concentration of 1 to 2 mM. Concentrations higher than 2 mM inhibited the activity. dATP stimulated CDP reduction even at concentrations as high as 1 mM, with inhibition found at higher concentrations. This pattern of dATP stimulation and inhibition is similar to that observed in *S. typhimurium* nrdEF ribonucleotide reductase yet quite different from the mammalian system where inhibition is seen at concentrations greater than 0.1 mM dATP.

MATERIALS AND METHODS

All restriction enzymes were purchased from NEBioLab. pET-11a and BL21(DE3) competent cells were from Novagen. DEAE-cellulose was from Sigma. Protein concentrations were determined using the method of Bradford M. M. 1996 *Anal. Biochem.* 72:248–251, which is incorporated herein by reference). Partially purified wild type *M. tuberculosis* ribonucleotide reductase holoenzyme and pure recombinant R1 were prepared as described in Yang, F.-D., et al. 1990 *FEBS* 272(1,2):61–64 which is incorporated herein by reference. Heptapeptides Acetyl-TDTDWDF-OH (SEQ ID NO:7) and Acetyl-EDDDWDF-OH (SEQ ID NO:8) identical to *M. tuberculosis* R2-1 and *M. tuberculosis* R2-2 C-terminal sequences, called R2P7-1 and R2P7-2, were purchased from SynPep (P.O.Box 2999, Dublin, Calif. 94568).

Isolation of partial R2 sequences

Two sets of PCR primers were used in PCR reactions to isolate the first fragments of *M. tuberculosis* R2 genes. The first set of primers (N and C1 primers) was: N-terminal primer 5'-TTCATGGAGGC(G/C)GT(G/C)CA-3' (SEQ ID NO:9) and C-terminal primer 5'-TAGAACAGGAA(G/C)GACTC-3' (SEQ ID NO:10). The second set of primers (N and C2 primers) was: N-primer, the same as the N-primer in first set, and C-primer 5'-TG(G/C)AC(G/C)GCCTCGTC (SEQ ID NO:11). The PCR reactions were carried out in separate tubes in 100 μl which contained 0.25 μg of *M. tuberculosis* genomic DNA, 100 pmol of primers, all four dNTPs (each 0.2 mM), 10 μl 10×PCR buffer (Perkin-Elmer) and 2.5 U Taq polymerase (Perkin-Elmer). The reactions were conducted in 30 cycles with the following program: 20 s at 94° C., 30 s at 48° C., and 30 s at 72° C. The two PCR products, 200 bp oligonucleotide from the first set of primers and 300 bp oligonucleotide from the second set of primers, were purified from an agarose gel using Qiaex silica gel particles (Qiagen), subcloned and sequenced.

Southern Analysis

*M. tuberculosis* DNA (1 mg for each reaction) was digested with EcoRI, Not I, Sac I and Xba I in a final volume of 10 ml at 37° C. overnight. The digested mixture was separated on a 0.7% agarose gel (20 cm) at 70 V for 6 hrs in 1×TBE buffer. The DNA was transferred onto a nylon membrane (MSI), dried at 80° C. for 2 hrs and pre-hybridized with 25 ml of hybridization mixture (50% formamide, 5×SSPE, 0.1% SDS, and 0.25% dry milk) at 42° C. for 1 hr in a hybridization bag. $^{32}$P labeled oligonucleotide probe, representing the 200 bp PCR product obtained with the first set of primers (probe 1) was added directly to the hybridization bag and hybridization was continued for 48 hrs at 42° C. After the film was developed, the membrane was stripped and reprobed with the $^{32}$P labeled 300 bp PCR product obtained with the second set of primers as discussed above (probe 2).

Construction of a size selected *M. tuberculosis* R2-1 or R2-2 library in Lambda ZAP II

*M. tuberculosis* DNA (10 mg) was digested with Sac I (for R2-1) or EcoR I (for R2-2) in the corresponding buffer in a final volume of 100 ml at 37° C. overnight. The digested DNA was then separated by agarose gel electrophoresis using the same conditions as described for the Southern analysis. The 4 kb SacI fragment, and the 6 kb EcoR I fragment were purified with Qiaex, ligated to the correspondingly prepared Lambda ZAP II (Stratagene). XL1-Blue were infected with the recombinant phage preparations and screened with either probe 1 or probe 2. Positive plaques were picked and the recombinant phagemids were excised and used to transform XL1-Blue. The phagemids were purified and the sequences of the inserts were determined.

Expression of *M. tuberculosis* R2-1 and *M. tuberculosis* R2-2

Full length *M. tuberculosis* R2-1 was isolated from genomic *M. tuberculosis* DNA by PCR using primers with Xba I cloning sites (underline) (N-primer, <u>TCTAGA</u>ATGACCGGCAAGCTCGTTG SEQ ID NO:12; C-primer, <u>TCTAGA</u>TTAGAAGTCCCAGTCGGTG SEQ ID NO:13). Full length *M. tuberculosis* R2-2 was isolated from the 6 kb insert containing recombinant phagemid DNA containing by PCR using primers containing Nhe I cloning sites (underline) (N primer, 5'-<u>GCTAGC</u>GTGACTGGAAACGCAAAG SEQ ID NO:14; C primer, 5'-<u>GCTAGC</u>CTAGAAGTCCCAGTCATC SEQ ID NO:15). The PCR reaction mixture, in a total volume of 100 ml, contained 0.25 mg of genomic or phagemid DNA, 100 pmol of each primer, all four dNTPs (each at 0.2 mM), and 3.0 U of Taq polymerase. The reaction was carried out in 30 cycles of the following program: 20 s at 94° C., 20 s at 54° C., 3 min at 72° C. The PCR product was gel purified with GenElute Agarose Spin Column (Supelco) and cloned into the pCR vector (Invitrogen). The recombinant plasmid was then transformed into OneShot bacteria, purified and digested with XbaI (*M. tuberculosis* R2-1) or NheI (*M. tuberculosis* R2-2). The excised *M. tuberculosis* R2-1 or *M. tuberculosis* R2-2 gene was again gel purified and cloned into the NheI linearized pET-11a plasmid. BL21(DE3) competent cells were transformed, induced with 0.4 mM IPTG and grown at 37° C. for 2.5 hours.

Purification of the Recombinant *M. tuberculosis* R2-2

Recombinant *E. coli* cell paste (3 g) was suspended in 30 ml of 50 mM Tris-HCl, 0.1 mM DTT, pH 7.5 (buffer A) containing 2 mM PMSF and disintegrated with French press. The cell debris was removed by centrifugation at 23,000×g for 20 min. A solution of 10% streptomycin sulfate in buffer A was added to the supernatant to a final concentration of 0.5% with stirring to precipitate DNA and ribosomal RNA. The precipitate was removed by centrifugation (23,000×g, 20 min). Solid ammonium sulfate was slowly added to the supernatant to 60% saturation with stirring. After the addition was complete, the suspension was stirred for 10 min and the precipitate was collected by centrifugation (23,000×g, 20 min). The pellet was resuspended in 5 ml of buffer A and dialyzed against the same buffer for 5 hrs with one buffer change. After removal of insoluble protein by centrifugation (5,000×g, 10 min), the dialysate was loaded onto a DE52 column (1×6 cm) which was preequilibrated with buffer A. The column was washed with 20 ml of buffer A containing 100 mM KCl, and 15 ml of buffer A containing 200 mM KCl subsequently. R2 was then eluted with 20 ml of buffer A containing 300 mM KCl and concentrated in an Amicon concentrator. Concentrated R2 was diluted 3 fold with buffer A to reduce the concentration of salt, concentrated one more time and stored at −70° C. *M. tuberculosis* rR2-2 remained soluble throughout the purification process while, under the same conditions, *M. tuberculosis* rR2-1 was insoluble.

Activity assays of the recombinant *M. tuberculosis* ribonucleotide reductase

Activities were determined from the rate of reduction of [$^3$H]CDP as described previously in Yang et al. 1990 SUPRA. 5 mg of holoenzyme was generated from an equimolar ratio of recombinant R1 and R2-2 in order to determine the effects of ATP and dATP on CDP reduction and to measure inhibition of activity by peptides R2P7-1 and R2P7-2.

The effect of ATP and dATP on CDP reduction was examined. 5 mg recombinant ribonucleotide reductase (1 to 1 molar ratio of R1 to R2) was used in each assay in a final volume of 100 ml in the presence of 6 mM CDP. Reactions were carried out at 37° C. for 20 min.

Nucleotide sequence accession numbers

The GenBank accession number for *M. tuberculosis* R2-1 is U41099 and for *M. tuberculosis* R2-2 U41100, which are incorporated herein by reference.

RESULTS

Isolation of *M. tuberculosis* R2-1 and R2-2 genes

Using high molecular weight DNA extracted from the Erdman strain of *M. tuberculosis* as template, the N and C1 set of PCR primers (SEQ ID NO:9 and SEQ ID NO:10) generated 200 bp PCR product and the N and C2 set of PCR primers (SEQ ID NO:9 and SEQ ID NO:11) generated 300 bp PCR product were not identical in the region of overlap. Nevertheless, both fragments contained an open reading frame and both were homologous with *S. typhimurium* R2F. This result led to the postulate that there may be two R2 genes in *M. tuberculosis*. In fact, the Southern blot hybridization pattern of Sac I, Not I and EcoRI digested *M. tuberculosis* DNA was different when probed with the two PCR products.

Sequence analysis of the complete coding region of the two genes confirmed the hypothesis. There is 71% homology at the DNA level between the two genes and 71% identity in the derived amino acid sequence. *M. tuberculosis* R2-1 is 64%, and *M. tuberculosis* R2-2 is 71% identical to the *S. typhimurium* nrdF gene product. This is in contrast to 21–23% identity to the *E.coli* nrdB gene product and approximately 16% identity with the human R2 subunit.

Alignment of the two *M. tuberculosis* R2 polypeptides with *S. typhimurium*, human and *E. coli* R2 demonstrated that both *M. tuberculosis* R2s contain the conserved free radical tyrosine corresponding to Tyr122; the iron binding residues corresponding to Asp 84, Glu115, His118, Glu204, Glu238 and His241 in *E. coli* R2 and Trp34 and Asp44; and the hydrophobic pocket forming residues corresponding to Phe 208, Phe 212 and Ile 234 in *E. coli* R2 proposed to be essential to mediate electron transfer to the large subunit.

The C-terminal residues of the *M. tuberculosis* R2 genes differ significantly from any other R2 gene thus far identified. Differences between the human R2 C-terminus and *M. tuberculosis* R2 C-terminus include Phe383 replaced by threonine (in R2-1) or glutamic acid (in R2-2), Thr384 replaced by Asp, Lue385 replaced by Thr (in R2-1) or Asp (in R2-2), and Ala387 replaced by Trp. The existence of a phenylalanine in position 383 in the mammalian system has been shown to be essential for the binding of peptide inhibitors to the large subunit. Residues Leu385 and Ala387 are also critical residues in mammalian R2-R1 binding. Clearly, the C-termini of *M. tuberculosis* R2s are more hydrophilic and more negatively charged than that of human R2. There are 5 residues with their side chains negatively charged in R2-2. Plus the carboxyl group of Phe324, there are 6 negatively charged carboxyl groups among the seven C-terminal residues, indicating that the binding domain on R1 must be more positively charged. The observed divergence at the C-terminus between human and *M. tuberculosis* may have important impact on antituberculous drug development given the potential to develop species specific inhibitors of ribonucleotide reductase based on the differences between their C-terminal amino acids.

Gene organization of *M. tuberculosis* R2

A search of Genbank revealed an exact match starting 48 nucleotides following the stop codon of *M. tuberculosis* R2-1 which corresponded to the 5' non-coding region of the gene encoding MPT64, a secreted protein from *M. tuberculosis*, identified recently to be thioredoxin. This sequence includes the −35 and −10 promoter region of MPT64. Further sequence analysis showed that the entire 5' non-coding, the coding and 3'-non-coding region of MPT64 is found downstream from the *M. tuberculosis* R2-1 gene. The 3' non-coding sequences of the salmonella nrdF gene correspond to the upstream sequences of the proV gene in the proU operon. ProV is involved in the osmotic regulation in salmonella and does not appear to be related in sequence to the MPT64 gene in mycobacteria. Extensive sequence analysis of the 5' and 3' flanking regions of *M. tuberculosis* R2-2 did not reveal adjacent coding regions.

Unlike other bacterial ribonucleotide reductase systems, R1 was not found to form an operon with either *M. tuberculosis* R2-1, or *M. tuberculosis* R2-2.

Expression, purification and activity of recombinant *M. tuberculosis* R2

When *M. tuberculosis* R2-1 and *M. tuberculosis* R2-2 were cloned and expressed in *E. coli*, only recombinant *M. tuberculosis* R2-2 was soluble. Preliminary work on unfolding and refolding the insoluble *M. tuberculosis* R2-1 did not yield biologically active R2.

Recombinant *M. tuberculosis* R2-2 purified to greater than 90% as estimated by SDS-PAGE. Using this expression system, more than 20 mg of pure *M. tuberculosis* rR2-2 was obtained from 1 liter culture.

The activity of the recombinant *M. tuberculosis* ribonucleotide reductase was determined by the rate of dCDP production using DTT as reductant. In all activity assays an equi-molar ratio of R1 and R2 was used to reconstitute the enzyme. dATP stimulated CDP reduction at concentrations as high as 1 mM and showed more efficient than ATP at low concentration while ATP was a more potent positive effector for CDP reduction at higher concentration than dATP. ATP stimulated CDP reduction up to 45 pmoles dCDP in 20 min, while dATP can only to 13 pmoles under same assay condition.

Inhibition of CDP reduction activities of reconstituted *M. tuberculosis* ribonucleotide reductase by R2P7-1 and R2P7-2 was evaluated. 5 mg reconstituted ribonucleotide reductase (1 to 1 molar ratio of R1 to R2-2) was used in each assays in final volume of 100 ml in the presence of 6 mM CDP, 2 mM ATP and 0.0–0.5 mM amount of the inhibitors. The activity of recombinant *M. tuberculosis* was inhibited by R2P7-2 with an $IC_{50}$ of 15–20 mM and by R2P7-1 with an $IC_{50}$ of 100 mM. The $IC_{50}$ of R2P7-2 is consistent with that found in other ribonucleotide reductase systems. For example, for the mammalian enzyme, the $IC_{50}$ for a heptamer corresponding to the R2 C-terminal tail of the mammalian R2 is 20 mM and for the herpes simplex virus enzyme, the $IC_{50}$ is 20 mM for the nonapeptide corresponding to the herpes simplex virus R2 C-terminal tail. By contrast, $IC_{50}$'s in the range of 20 mM are not obtained for the nrdAB system until the length of the peptide reaches approximately 37 residues. The differential inhibition of *M. tuberculosis* ribonucleotide reductase activity by the two peptides, reflecting the relatively weak binding of the C-terminal tail corresponding *M. tuberculosis* R2-1 to *M. tuberculosis* R1 indicates that it is unlikely that *M. tuberculosis* R2-1 would form an active holoenzyme with *M. tuberculosis* R1 in vivo under normal growth conditions. This suggests that under conditions where *M. tuberculosis* R2 is expressed, another, as yet unidentified *M. tuberculosis* R1 is expressed. Comparison of partially purified ribonucleotide reductase holoenzyme from *M. tuberculosis* extracts with the two recombinant R2s clearly showed that one band of the holoenzyme corresponded R2-2 and no protein component could be identified that corresponded to R2-1.

Absorption spectra of recombinant *M. tuberculosis* R2-2 and hydroxyurea treated *M. tuberculosis* R2-2 was evaluated. 12 mM R2-2 in 50 mM tris-HCl, 0.1 mM DTT, pH 7.6 was tested as was 12 mM R2-2 in 50 mM tris-HCl, 0.1 mM DTT, pH 7.6 after 5 min incubation with 15 mM hydroxyurea, and 12 mM R2-2 in 50 mM tris-HCl, 0.1 mM DTT, pH 7.6 was test after 10 min incubation with 15 mM hydroxyurea. The spectra were taken from a Shimadzu UV-Visible spectrophotometer UV-160.

The UV spectrum of *M. tuberculosis* rR2-2 showed a typical tyrosyl radical absorbance band at 408 nm that could be abolished upon incubation with 15 mM of hydroxyurea for 10 min. In addition, hydroxyurea inhibited the activity of CDP reduction with an $IC_{50}$ of 2 mM which is slightly higher than that found for calf thymus (IC90 of 1 mM) and Salmonella ribonucleotide reductase ($IC_{50}$ approx. 0.5 mM) and may reflect structural differences in the enzyme from different species.

Example 2

In vitro assays are performed to identify inhibitors of *M. tuberculosis* ribonucleotide reductase activity using the recombinant *M. tuberculosis* ribonucleotide reductase (R1 and R2-1). The activity is measured by determining by the rate of deoxyribonucleotide production using DTT as reductant. An equimolar ratio of R1 and R2 is used to reconstitute the enzyme.

[5-$^3$H] CDP, [8,5-$^3$H] GDP, [8-$^3$H] ADP and [α-$^{32}$P]dATP were purchased from Amersham. All cold NDPs and NTPs were from Sigma. Sepharose 4B was purchased from Pharmacia. Phenylboronate sepharose (PBA-60) was purchased from Amicon.

dATP stimulates ribonucleotide diphosphate reduction at concentrations as high as 1 mM and is more efficient than ATP at low concentration while ATP was a more potent positive effector for ribonucleotide reduction at higher concentration than dATP. ATP stimulates ribonucleotide reduction up to 45 pmoles deoxyribonucleotide in 20 min, while dATP can only to 13 pmoles under same assay condition.

Inhibition of ribonucleotide reduction activities of reconstituted *M. tuberculosis* ribonucleotide reductase by using 5 mg reconstituted ribonucleotide reductase (1 to 1 molar ratio of R1 to R2-2) in each assays in final volume of 100 ml in the presence of 6 mM NDP, 2 mM ATP and 0.0 $\mu$M–1 nM amount of candidate inhibitors.

The ribonucleotide reductase assay used directly separates the deoxyribonucleotide product from the reaction mixture over a phenylboronate agarose gel (PBA-60). The reaction mixture, made up in a final volume of 100 ml of 60 mM Hepes, pH 7.6 buffer, contained 8 mM $Mg(OAc)_2$, 8.75 mM NaF, 0.05 mM $FeCl_3$, 25 mM DTT and varying amounts of effector and [$^3$H] NDP substrate. The reaction was started by the addition of the enzyme (either partially purified or highly purified), carried out at 37° C. and stopped by heating in a boiling water bath for 3 minutes. The denatured protein was removed by centrifugation. The supernatant was diluted with equal volume of 50 mM tris-HCl buffer, pH 8.5 containing 50 mM magnesium chloride and applied onto a 0.5×6.0 cm PBA-60 column which was pre-equilibrated with the same buffer. The column was then washed with 5 ml of the same buffer. The quantity of deoxyribonucleotide was determined by liquid scintillation. The column was regenerated by washing with 10 ml of 50 mM sodium citrate buffer, pH 6.5 and double deionized water. All assays were carried out in triplicate.

Example 3

Construction of the ts complementation system—the drug screening system

The genes encoding *M. tuberculosis* ribonucleotide reductase are not contained in an operon as they are in *E. coli* and Salmonella. Therefore, two systems were designed to express *M. tuberculosis* ribonucleotide reductase: 1) where the genes are arrayed in a mini-operon construct and 2) where each gene is arrayed on a separate expression plasmid.

The mini-operon was inserted into the commercially available IPTG inducible expression vector pTrc99A as follows. The *M. tuberculosis* R1 gene was inserted into the multiple cloning site of pTrc99A using a PCR primer generated NcoI site at the N-terminus and a SacI site at the C-terminus. The *M. tuberculosis* R2 gene was inserted using a PCR primer generated KpnI restriction site, a ribosome binding site and 7 nucleotide spacing before the first coding triplet (ATG), at the N-terminus. The ribosome binding site found in the Salmonella operon which has been shown to work in *E. coli* (Jordan, A., et al. 1994 *J. Bact.* 176(11):3420–3427 and Jordan, A., et al. 1994 *Proc. Natl. Acad. Sci. USA* 91:12892–12896 which are incorporated herein by reference) was utilized. While the *M. tuberculosis* R2 start codon is valine, a methionine start codon was chosen in order to maximize the likelihood of expression in *E. coli*. The TbR2 C-terminal primer was designed to add a HindIII site to the end of the gene for cloning purposes. pTrc99A containing this mini-operon construct was denoted pTrcMTbRRop. pTreMTbRRop was electroporated into nrdA *E. coli* using the BioRad Gene Pulser.

To generate the vectors for the second system, *M. tuberculosis* R1 was PCR amplified with an NcoI site at the N-terminus, and a SacI site at the C-terminus and ligated into pTrc99A. This expression vector was denoted pTrcMTbR1. In order to avoid the problem of plasmid exclusion in *E. coli*, a compatible second hybrid plasmid vector was constructed containing the transcriptional machinery and lacI repressor gene of pTrc99A, the origin of replication, p15A, from the plasmid pACYC177 and kanamycin resistance gene. This hybrid plasmid was denoted pSC. *M. tuberculosis* R2 was inserted into pSC using PCR generated cloning sites and the resultant expression plasmid denoted pSCMTbR2. pTrcMTbR1 and pSCMTbR2 were then electroporated into ts nrdA *E. coli.*

Electroporation and complementation were carried out as follows. Frozen nrdA cells were grown overnight at 30° C. in 5 ml of 2YT media with streptomycin, a marker contained in this strain of nrdA. One ml of overnight culture was added to 50 ml of 2YT/Strep media, and grown at 30° C. to $Ab_{600}$=1. The cells were washed twice with distilled water, once with 10% glycerol, and resuspended in 0.2 ml of 10% glycerol. The gene pulser apparatus was set at: 200 Ohms, 25 microfarrads, 2.5 kV. 2 ul of pTrcMTbRRop (20 ng/ul) or 2 ul of both pTrcMTbR1 (100 ng/ul) and pSCMTbR2 (100 ng/ul) wee mixed with 45 ul of nrdA *E. coli* ($Ab_{600}$=1) and subjected to electroporation. One ml of LB was then added and the cells were allowed to grow at 30° C. for 1 hour. After 1 hour, the cells were induced with IPTG and grown at 30° C. for 45 minutes then spread onto agar plates containing 50 microliters of 0.2M IPTG, and either ampicillin/streptomycin for pTrcMTbRRop selection or ampicillin/streptomycin/kanamycin for selection of the double plasmid system. Plates were incubated at 30° C. and 42° C. overnight. A protein extract was prepared from successful 42° transformants from both systems and the presence of recombinant R1 and R2 was confirmed by SDS gel electrophoresis. The same set of expression vectors were created containing the mammalian ribonucleotide reductase genes which, upon electroporation and selection as above, generated no complementation.

Example 4

(a) Isolation of the gene of *M. tuberculosis* topoisomerase I

In our attempt to isolate the gene encoding the small subunit of ribonucleotide reductase (RR) from *M. tuberculosis*, a 288 bp fragment was isolated using N and C primers derived from the amino acid sequence of *E. coli* RR small subunit. Unexpectedly, sequence analysis of this fragment revealed a high degree of homology with Topo I from synechococcus rather than with the small subunit of ribonucleotide reductase. This fragment was subsequently used as a probe to isolate the complete gene encoding *M. tuberculosis* topoisomerase I (SEQ ID NO:3).

The gene was isolated in two steps. The 5' 2249 nucleotides contained in the DNA fragment between NotI cutting sites was first isolated by screening with Probe 1. The 3' 451 nucleotides contained in the DNA fragment between the two SacI cutting sites was isolated by screening with Probe 2.

Probe 1, the first 288 bp fragment of *M. tuberculosis* Topo I gene, was isolated by PCR using *M. tuberculosis* genomic DNA as template and primers (N primer, 5'-ATCGAGAACATCCA SEQ ID NO:14; C primer, 5'-AAGAAGATGCCCTC SEQ ID NO:15) which were designed for isolation of ribonucleotide reductase from *M. tuberculosis*. The PCR reaction was carried out in a total volume of 100 ml which contained 0.25 mg of *M. tuberculosis* genomic DNA, all four dNTPs (each at 0.2 mM), 10 ml of 10×PCR buffer (Perkin-Elmer), 2.5 U Taq polymerase and 100 pmol of each primer. The reaction was conducted in 20 cycles of the following program: 20 s at 94° C., 30 s at 45° C., and 60 s at 72° C. The PCR product was purified from agarose gel with Qiaex silica gel particles (Qiagen) according to the manufacture's protocol.

Probe 2, a 300 bp oligonucleotide corresponding to the 3' end of the 3.7 kb fragment, was also prepared by PCR in the same way.

To isolate the whole gene, *M. tuberculosis* DNA was digested with restriction enzyme and then analyzed by Southern blot. Thus, *M. tuberculosis* DNA (1 mg) was digested with either 5 U of NotI or 10 U of SacI in a final volume of 10 ml at 37° C. overnight. The digested fragments were separated by electrophoresis through a 0.7% agarose gel (20 cm) at 70 V for 6 hrs in 1×TBE buffer. The DNA was transferred onto a nylon membrane (MSI), dried at 80° C. for 2 hrs and pre-hybridized with 25 ml of hybridization mixture (50% formamide, 5×SSPE, 0.1% SDS, and 0.25% dry milk) at 42° C. for 1 hr. $^{32}P$ labeled oligonucleotide probe was added directly to the hybridization bag and hybridization continued for 48 hrs at 42° C. The hybridized band was visualized by autoradiography. Based on the result of Southern analysis, 10 mg of *M. tuberculosis* DNA was digested with either NotI or SacI in the corresponding buffer in a final volume of 100 ml at 37° C. overnight. The digested DNA was then separated by agarose gel electrophoresis using the same conditions as used in the Southern analysis. The DNA fragment on the gel corresponding to the band shown on the Southern blot was purified with Qiaex and ligated to the correspondingly prepared Lambda ZAP II (Stratagene). The recombinant phage were used to infect XL1-Blue and screened with either Probe 1 or Probe 2. Positive plaques were picked and the recombinant phagemid excised by following the manufacture's protocol. The phagemid was then transformed XL1-Blue, purified, and sequenced.

After the complete gene sequence was determined, the explanation for selection of topoisomerase I using ribonucleotide reductase primers became clear. The DNA sequence used as the initial N-primer was identical to nucleotide positions 1662 to 1676 in *M. tuberculosis* topoisomerase I, except for two residues. Similarly, 9 of 14 C-primer residues were identical to nucleotide positions 1942 to 1950 in *M. tuberculosis* topoisomerase I.

The 3.7 kb fragment between the two Not I restriction sites was isolated from a size selected Not I library in Lambda Zap II screened with the original 288 bp PCR product. This fragment contained 2249 residues in the 5' region of the gene. The C-terminal region of the gene was isolated from a size selected Sac I digest library of genomic DNA screened with a 300 bp probe corresponding to the 3' end of the 3.7 kb fragment.

(b) Structure analysis of the gene and the enzyme

A 4.4 kb of *M. tuberculosis* genomic DNA was isolated and 3007 bp sequenced (SEQ ID NO:3). The GenBank accession number for the DNA sequence of *M. tuberculosis* topoisomerase I is U 40159. Within this region, an open reading frame of 2700 nucleotides was identified. The potential ATG start codon preceded by a plausible ribosome binding site, GGGATAA (underline) was identified. The gene encodes a polypeptide of 900 amino acids with a predicted molecular mass of 99353 Daltons. The coding region is 65.7% G+C, with third position of the codons 65.6% G or C rich.

The amino acid alignment of *M. tuberculosis* topoisomerase I with that of *E. coli* and synechococcus topoisomerase I shows that there is 20% and 30% overall identities respectively. Most of the identical residues are located in the N-terminal domain which include the active site tyrosine 347. Atomic resolution X-ray crystallographic analysis of the 67 kDa N-terminal fragment of *E. coli* topoisomerase I revealed a torus shaped structure with a 27.5 Angstrom average diameter hole. The structure indicates that the active site tyrosine 319 and its neighboring amino acids in the tertiary structure are involved in an extensive network of hydrogen bonds. This network consisting of Glu30, Lys34, Asp116, Asp118, Glu120, Gln337, Tyr340, Glu341, and Arg349 are all conserved in *M. tuberculosis* topoisomerase I. In contrast, there is no significant homology between *M. tuberculosis* topoisomerase I and *E. coli* topoisomerase III analyzed by computer.

The homology between *M. tuberculosis*, synechococcus and *E. coli* topoisomerase I breaks down in the C-terminal domain beyond amino acid residue 600. Activity studies of intact and C-terminal truncated *E. coli* topoisomerase I and topoisomerase III demonstrated that the C-terminal domain contains the DNA binding site. The DNA binding property largely comes from a zinc finger structure (*E. coli* topoisomerase I) or positively charged amino acid residues (*E. coli* topoisomerase III). *M. tuberculosis* topoisomerase I does not contain a zinc finger DNA binding motif in the C-terminal region of the protein. However, similar to *E. coli* topoisomerase III, there are short domains of residues that may contribute to the DNA binding property of this enzyme.

(c) Expression and activity of recombinant *M. tuberculosis* topoisomerase I

*M. tuberculosis* topoisomerase I was expressed in *E. coli* BL21(DE3) and purified nearly to homogeneity. To express *M. tuberculosis* topoisomerase I, the gene was isolated by PCR using *M. tuberculosis* genomic DNA as template and primers that contained NheI cloning sites (underline): N primer, 5'-<u>GCTAGC</u>ATGGAGCGTGGGGCGCAGTTGGCTG SEQ ID NO:16; C primer, 5'-<u>GCTAGC</u>TTATGGAAGCCACGTCGTCGCCCT SEQ ID NO:17. The PCR reaction mixture, in a total volume of 100 ml, contained 0.25 mg of *M. tuberculosis* genomic DNA, 100 pmol of each primer, all four dNTPs (each at 0.2 mM), 3.0 U of Taq polymerase and 10% DMSO. The reaction was carried out in 30 cycles of the following program: 20 s at 94° C., 20 s at 54° C., 4 min at 72° C. The PCR product was gel purified and cloned into pCR vector (Invitrogen). The recombinant plasmid was then transformed to OneShot cell, purified and digested with NheI. The excised topoisomerase I gene was again gel purified and cloned into the NheI linearized pET-11a plasmid. BL21(DE3) competent cells were transformed, induced with 0.1 mM IPTG and grown at 15° C. overnight. The crude extracts from un-induced recombinant *E. coli* (15 mg), from induced recombinant *E. coli* (10 mg), and purified recombinant *M. tuberculosis* topoisomerase I (1 mg) were analyzed by 8% SDS-PAGE.

About 10 mg of pure recombinant *M. tuberculosis* topoisomerase I was obtained from 2 g of *E. coli* cell paste. The purification procedure was largely adopted from that for *E. coli* topoisomerase I purification except the final step of single stranded DNA-Agarose chromatography. The advantage of using this procedure was that the contaminate host *E. coli* topoisomerase I (10 mg in 2 g cell paste, about 0.1% of the total amount of recombinant *M. tuberculosis* topoisomerase I contained there) was able to be removed from the recombinant *M. tuberculosis* topoisomerase I in the step of phosphocellulose column chromatography, where *E. coli* topoisomerase I was absorbed on the column and the recombinant *M. tuberculosis* topoisomerase I directly flew through the column.

The recombinant *M. tuberculosis* topoisomerase I was purified as follows. Recombinant *E. coli* cell paste (2 g) was suspended in 20 ml of 50 mM $Na/PO_4$, 100 mM KCl, 5% glycerol, 0.1 mM DTT, pH 7.5 (buffer A) containing 2 mM PMSF and disintegrated in a French press. The cell debris was removed by centrifugation at 23,000×g for 20 min. A solution of 10% streptomycin sulfate in buffer A was added to the supernatant to a final concentration of 0.5% with stirring to precipitate ribosomal RNA. The precipitate was removed by centrifugation (23,000×g, 20 min). Solid ammonium sulfate was slowly added to the supernatant to 60% saturation with stirring. After the addition was complete, the suspension was stirred for 10 min and the precipitate was collected by centrifugation (23,000×g, 20 min). The pellet was resuspended in 5 ml of buffer A and dialyzed against the same buffer for 4 hrs with one buffer change. After removal of insoluble protein by centrifugation (5,000×g, 10 min), the dialysate was loaded onto a phosphocellulose column (1×6 cm) which was pre-equilibrated with buffer A. The active *M. tuberculosis* topoisomerase I component in the breakthrough fraction was directly loaded onto a 2 ml ss-DNA agarose column. The column was washed with 10 ml of 50 mM Tris-HCL, 0.1 mM DTT, pH 7.6 (buffer B). *M. tuberculosis* topoisomerase I was eluted with 10 ml buffer B containing 1.0M KCl and then dialyzed against buffer B containing 0.1M KCl for 4 hrs with one buffer change. The dialysate was concentrated with a centriprep 10 (Amicon) and store at −70° C.

The activity assays with equal amounts of the 60% ammonium sulfate fraction of extract prepared from un-induced and induced *E. coli* showed that the expressed protein was enzymatically active in relaxing negatively supercoiled plasmid DNA, while the activity of the host *E. coli* topoisomerase I was not detectable. There is a good correlation between the activity and the amount of purified enzyme used in each assay.

Activities were measured in a final volume of 10 ml contained 0.25 mg of negatively supercoiled pUC19 plasmid DNA, 50 mM Tris-HCl (pH 8.0), 20 mM KCl, 0.5 mM DTT, 10.0 mM $MgCl_2$ and 30 mg/ml bovine serum albumin. The reaction was carried out at 37° C. for 10 min and stopped by the addition of 5 ml of stop solution which contained 5% SDS, 10 mM EDTA, 5% glycerol and 0.25% bromophenol blue, followed by heating at 65° C. for 10 min. The result was analyzed by electrophoresis on a 1.0% agarose gel (82 mm) in 1×TBE buffer at 100 V for about 1–2 hrs. The gel was then stained with ethidium bromide and photographed under UV light. Form I denotes supercoiled DNA and Form II completely relaxed or nicked circle DNA. Correlation between activity and amount of purified recombinant enzyme. Activities were measured at the same condition as that in panel A. The reaction was started by the addition of 0 ng, 30 ng, 150 ng, 300 ng, 600 ng, 1200 ng and 1800 ng of pure recombinant *M. tuberculosis* topoisomerase I.

The effect of magnesium ion on the activity was analyzed as follows. Activities were measured with 150 ng of purified recombinant *M. tuberculosis* topoisomerase I and in the presence of 0.0 mM, 0.1 mM, 0.5 mM, 1.0 mM, 5.0 mM, and 10.0 mM $MgCl_2$.

The effect of ATP on the activity was also analyzed. Activities were measured under the same conditions as above with 150 ng of purified recombinant *M. tuberculosis* Topo I and 1.0 mM $MgCl_2$ in the presence of 0.0 mM, 0.4 mM, 0.8mM, and 1.6 mM ATP.

Inhibition of enzymatic activity by spermidine was also evaluated. Inhibition of topoisomerase I activity was titrated with spermidine at 0.0 mM, 0.5 mM, 1.0 mM, 2.0 mM, and 4.0 mM in the presence of 150 ng of purified recombinant *M. tuberculosis* topoisomerase I. The assay condition were the same as that described above for testing the effect of ATP on activity.

The data indicated that DNA relaxing activity of the recombinant *M. tuberculosis* topoisomerase I required $Mg^{2+}$ with an optimal concentration of 1.0 mM. Higher $MgCl_2$ concentrations caused a more distributive than processive relaxation mechanism. In the presence of 4.0 mM spermidine, the enzymatic activity was almost completely inhibited. In all activity assay experiments, no ATP dependence was observed. On the contrary, ATP inhibited the reaction in agreement with the observation on type I DNA topoisomerase from *Fervidobacterium islandicum.*

(d) Conclusions

Our preliminary characterization of the expressed enzyme, together with the DNA alignment, strongly confirm that this enzyme is a type I DNA topoisomerase. Unlike the well characterized *E. coli* topoisomerase I, *M. tuberculosis* topoisomerase I does not contain a zinc finger DNA binding domain implying that there may be a difference in the enzyme-DNA binding mechanism. The availability of large amounts of recombinant *M. tuberculosis* topoisomerase I will facilitate a more complete characterization of the physical-chemical and biological properties of this enzyme.

Example 5

Ribonucleotide reductase, an allosterically regulated, cell cycle dependent enzyme catalyzing a unique step in the synthesis of DNA, the reduction of 2'-ribonucleotides to 2'-deoxyribonucleotides was purified 500 fold from *M. tuberculosis* Erdman strain through cell disruption, ammonium sulfate fractionation and dATP-sepharose affinity column chromatography. The enzyme consists of identical subunits R1 and R2, both of which are required for activity. R1 has a molecular weight of 84 Kd as identified by SDS-PAGE and photoaffinity labeling with dATP. The amino acid sequences of the N-terminal and two internal peptides were determined and a partial R1 gene was isolated by polymerase chain reaction (PCR) using primers designed from these amino acid sequences.

The coding sequences for a biologically active form of *M. tuberculosis* R1 were isolated by screening size selected libraries, regenerated by PCR amplification of high molecular weight *M. tuberculosis* DNA and expressed in *E. coli*. This coding sequence is 2169 nucleotides and contains no introns. The predicted molecular weight of R1 from the DNA sequence is 82244 Da. Recombinant *M. tuberculosis* R1, purified to homogeneity, was biologically active when assayed with extracts of *M. tuberculosis* enriched for R2.

MATERIALS AND METHODS

Materials

[5-$^3$H] CDP, [8,5-$^3$H] GDP, [8-$^3$] ADP and [$\alpha$-$^{32}$P]dATP were purchased from Amersham. All cold NDPs and NTPs were from Sigma. Sepharose 4B was purchased from Pharmacia. Phenylboronate sepharose (PBA-60) was purchased from Amicon. The molecular weight markers for SDS-PAGE were purchased from Bio-Rad.

Purification of *M. tuberculosis* Ribonucleotide Reductase

Twenty grams of *M. tuberculosis* cell paste was washed once with 100 ml of 50 mM Tris-HCl, 5 mM $MgCl_2$, 0.1 mM DTT, pH 7.6 (Buffer A), resuspended in 200 ml of buffer A containing 2 mM phenylmethyl sulfonyl fluoride and subjected to two rounds of disruption in a pre-chilled French Press. The cell debris was removed by centrifugation at 23,000×g for 30 minutes. The supernatant was precipitated by addition of 10% streptomycin sulfate in buffer A to a final concentration of 0.5%. The resulting suspension was stirred for an additional 10 minutes, and the precipitate was removed by centrifugation (23,000×g, 20 min.). Solid ammonium sulfate was slowly added to the supernatant to 60% saturation with stirring. After the addition was completed, the suspension was stirred for 10 minutes and the precipitate was collected by centrifugation (23,000×g, 20 min.) and resuspended in 15 ml buffer A. The suspension was dialyzed against the same buffer for 5 hours with one buffer change. The dialysate (referred to hereafter as partially purified enzyme) was centrifuged at 13,800×g for 5 minutes and then applied onto a 1.0×3.0 cm dATP-sepharose column at room temperature in small aliquots. dATP-substituted sepharose gel was prepared by well known methods. Briefly, dADP was condensed with p-nitrophenyl phosphate which was activated with diphenylphosphoro-chloridate. After hydrogenation of the nitro group of the p-nitrophenyl ester of dATP, the p-aminophenyl ester of dATP was coupled to cyanogen bromide activated sepharose 4B. The column was then washed with 10 column volumes of buffer A. Ribonucleotide reductase was eluted with 10 ml of buffer A containing 10 mM ATP, concentrated to 200 ml with centriprep-10 (Amicon), and stored at −70° C. (referred to hereafter as highly purified enzyme).

Ribonucleotide Reductase Activity Assay

The ribonucleotide reductase assay followed the method of Steeper, J. R. and C. D. Steuart, 1970. *Analytical Biochem* 34:123–130, which is incorporated herein by reference, modified to directly separate the deoxyribonucleotide product from the reaction mixture over a phenylboronate agarose gel (PBA-60). The reaction mixture, made up in a final volume of 100 ml of 60 mM Hepes, pH 7.6 buffer, contained 8 mM Mg(OAc)$_2$, 8.75 mM NaF, 0.05 mM FeCl$_3$, 25 mM DTT and varying amounts of effector and [$^3$H] NDP substrate. The reaction was started by the addition of the enzyme (either partially purified or highly purified), carried out at 37° C. and stopped by heating in a boiling water bath for 3 minutes. The denatured protein was removed by centrifugation. The supernatant was diluted with equal volume of 50 mM tris-HCl buffer, pH 8.5 containing 50 mM magnesium chloride and applied onto a 0.5×6.0 cm PBA-60 column which was pre-equilibrated with the same buffer. The column was then washed with 5 ml of the same buffer. The quantity of deoxyribonucleotide was determined by liquid scintillation. The column was regenerated by washing with 10 ml of 50 mM sodium citrate buffer, pH 6.5 and double deionized water. All assays were carried out in triplicate.

Photoaffinity Labeling of *M. tuberculosis* ribonucleotide reductase with [$\alpha$-$^{32}$P]dATP Partially purified ribonucleotide reductase (30 mg) or pure ribonucleotide reductase (3 mg) in 20 ml of buffer A was mixed with 16 pmoles [$\alpha$-$^{32}$P]dATP (300 Ci/mmol) in the presence or absence of 5 mM ATP or 2.5 mM CDP and incubated on ice for 5 minutes. The mixture was placed as a drop on parafilm on dry ice and irradiated for 30 minutes using a UVP uv minerallight lamp, model UVGL-58. After irradiation, the protein was precipitated with 5% trichloro-acetic acid and washed 2 times with buffer A containing 5% trichloroacetic acid. The protein was then dissolved in loading buffer and analyzed on 12% SDS slab gels. The stained and dried gel was autoradiographed at room temperature for 5 hours.

N-terminal and internal amino acid sequence analysis

Highly purified *M. tuberculosis* ribonucleotide reductase (30 mg) was subjected to preparative SDS-PAGE (12% gel) and blotted onto an Immoblon-P membrane (Millipore) in 12.5 mM tris, 95 mM glycine-10% MeOH, pH 8.6 at 4° C. (100V, 1 hr). The membrane was washed with double distilled water and stained for 5 min with 0.25% coomassie blue R250 in 40% MeOH and destained for 10 min with 50% MeOH. The membrane was vacuum dried and N-terminal and internal sequence analysis was performed on the protein band.

Isolation of a partial sequence of the *M. tuberculosis* R1 gene

PCR using primers designed based on internal amino acid sequences was carried out in a total volume of 100 ml which contained 0.25 mg of *M. tuberculosis* genomic DNA, 100 pmoles of primers, all four dNTP (each at 0.2 mM), 10 ml of 10×PCR buffer (Perkin Elmer) and 2.5 units of Taq polymerase. The reaction was carried out in 20 cycles of the following program: 20 s at 94° C., 30 s at 45° C., and 60 s at 72° C. The PCR product was purified from an agarose gel using Qiaex silicagel particles (Qiagen) according to the manufacturer's protocol.

Expression and activity of recombinant *M. tuberculosis* R1 produced in *E. coli*

The R1 gene was isolated from high molecular weight *M. tuberculosis* DNA by PCR using primers that contained Nhe1 cloning sites (underlined): N-primer, 5'-AAAAAA<u>GCTAGC</u>CCCACCGTGATCGCCGAGCCCGTAGCCTC SEQ ID NO:18; C-primer, 5'-AAAAAA<u>GCTAGC</u>CTACAGCATGCAGGA SEQ ID NO:19. The PCR reaction mixture in a total volume of 100 ml contained 0.25 mg of *M. tuberculosis* genomic DNA, 100 pmoles of each primer, all four dNTPs (each at 0.2 mM), and 2.5 units of Taq polymerase. The reaction was carried out in 30 cycles of the following program: 20 s at 94° C., 20 s at 55° C., and 90 s at 72° C. The PCR product was gel purified with Qiaex silicagel particles, digested with Nhe 1, phenol extracted and precipitated with ethanol. The cloning vector containing the heat inducible pL promoter was prepared by digestion with Nhe 1, treated with alkaline phosphatase, phenol extracted and precipitated with ethanol. 28 ng of *M. tuberculosis* R1 DNA prepared as above was ligated with Nhe 1 digested pZMs (15 ng) in a final volume of 10 ml containing 400 units of T4 DNA ligase and 1 ml of 10×ligation buffer at 16° C. overnight. The ligation mix was then used to transform N4830 (Pharmacia. New Jersey) competent cells and plated onto LB agar supplemented with ampicillin. *M. tuberculosis* R1 was expressed by heat induction at 42° C. The purification of the recombinant R1 was essentially the same as that of the wild type R1 from *M. tuberculosis*.

RESULTS AND DISCUSSION

Purification of *M. tuberculosis* ribonucleotide reductase

Twenty grams of cell paste yielded 80 mg of protein with a specific activity of 1000 units (nmoles of product per mg protein per hour). Ribonucleotide reductase activity was not detected in the crude extract, however, it was detectable in the 60% ammonium sulfate fraction and was stimulated by addition of ATP and inhibited by dATP. Based on this, and the observation that mammalian as well as *E. coli* ribonucleotide reductase were purified by dATP affinity chromatography, *M. tuberculosis* ribonucleotide reductase was purified 500 fold using ribonucleotide se affinity column.

ribonucleotide reductase activity found in the 60% ammonium sulfate fraction was resolved into two components using DE52 column chromatography in $Mg^{2+}$ free buffer A. The two fractions, one in the breakthrough (DE1) and a second in the 0.5M NaCl (DE2) fractions, lacked ribonucleotide reductase activity when assayed individually. The breakthrough fraction of dATP affinity chromatography (dA1) which contained no ribonucleotide reductase activity but is rich in R2 was able to restore ribonucleotide reductase activity to DE1, but not to the DE2 fraction, indicating that DE1 contains R1.

The enzyme was stable throughout the purification. However, activity decreased after one month storage at $-70°$ C. if the concentration of the protein was lower than 1 mg/ml. The partially purified enzyme was stable throughout the 4 hour incubation during the activity assay in the presence of substrate and effectors.

SDS-PAGE of the dATP-sepharose affinity purified material showed one major band with a molecular weight of 84,000 Da. This band was specifically labeled by $[\alpha-^{32}P]$ dATP in the presence of 2 mM CDP and was completely inhibited by 5 mM ATP which provided additional evidence that the protein was R1.

Activity of *M. tuberculosis* ribonucleotide reductase

*M. tuberculosis* ribonucleotide reductase utilized all four ribonucleoside diphosphates as substrate. The reduction of CDP and UDP could be detected in 60% ammonium sulfate precipitate, whereas reduction of ADP and GDP required the use of the dATP affinity purified material. Maximum activity (2 nmoles of dCDP/hr/mg protein) of partially purified enzyme for CDP reduction was obtained in the presence of 6 mM ATP. In the presence of dGTP (6 mM) and ATP (3 mM), 1.8 mg of the highly purified enzyme reduced 50 pmoles of dADP in 3 hours. The same amount of dGDP was produced by equal concentrations of highly purified enzyme in the presence of dTTP (1.5 mM) and ATP (3 mM) The reduction of all four NDPs was inhibited by dATP.

Identification of the gene encoding *M. tuberculosis* R1

Sufficient quantities of purified enzyme were generated to obtain N-terminal and internal amino acid sequence data in order to design PCR primers.

A fragment of 908 bp of R1 gene was isolated by polymerase chain reaction (PCR) using primers corresponding to peptide 2 (P2) (5'-GA(G/A)TTCTTCCA(G/A)AC SEQ ID NO:20) and peptide 3 (P3) (5'-GCGTAGGTGTCGATGAT SEQ ID NO:21). The 906 bp fragment was used to probe EcoR1 digested high molecular weight *M. tuberculosis* DNA. Two bands, 1.1 Kb and 2 Kb, were observed on the Southern blot. Two size selected libraries were generated in lambda ZAP II, one containing inserts of 1.1 Kb and one containing inserts of 2.0 Kb. Plaques were screened with the 908 bp fragment, positives were picked and the plasmid containing the insert was rescued. The 2 kb fragment contained 548 bp of coding region including a potential C-terminus, 358 bp of which overlapped with the 908 bp probe. The 1.1 kb fragment contained coding region 5' to that contained within the 2 Kb fragment but did not extend all the way to the N terminus. The N-terminal 522 bp fragment was isolated by PCR using primers corresponding to peptides 1 and 2: P1 (CCCACCGT (G/C)ATCGCCGAGCC(C/G)GT SEQ ID NO:22) and P2 (AGGGTCTGGAAGAACTC SEQ ID NO:23). Peptide 1 was the sequence determined from N-terminal analysis of highly purified *M. tuberculosis* R1 and therefore may represent a processed form of R1. In this regard, R1 with heterogeneous N-termini and identical activities have been isolated from *E. coli* suggesting that the N-terminus does not play a central role in either the catalytic or regulatory activity. The initial 908 bp fragment was generated by PCR from internal amino acid sequence data. Two EcoR1 fragments, 1.1 kB and 2 kB, provided all but the N-terminal region which was subsequently obtained as a PCR product using the results of amino acid analysis of the N-terminus and an internal site.

The nucleotide sequence of the 2169 base pair R1 gene (SEQ ID NO:24) encodes a protein of 723 amino acids with a calculated molecular weight of 82,244 Da. The coding region is 59% G+C with the third position of the codon 70% G/C rich. The 3' non-coding region is 63% G/C rich.

Expression and activity of recombinant *M. tuberculosis* R1

Recombinant *M. tuberculosis* R1 (*M. tuberculosis* rR1) was expressed in *E. coli* using a heat induced expression system. *M. tuberculosis* rR1 was soluble and had the same molecular weight as R1 purified from *M. tuberculosis* indicating little or no glycosylation. *M. tuberculosis* rR1 could also be photoaffinity labeled by $[\alpha-^{32}P]$dATP in the presence of CDP. The activity of purified *M. tuberculosis* rR1 assayed with dA1 was comparable to that of partially purified wild type *M. tuberculosis* ribonucleotide reductase indicating the authenticity of the recombinant gene product.

We claim:

1. A recombinant expression vector comprising a nucleic acid sequence that encodes the protein having the amino acid sequence of SEQ ID NO:2, SEQ ID NO:6 or SEQ ID NO:4.

2. A host cell comprising the recombinant expression vector of claim 1.

3. An isolated nucleic acid molecule selected from the group consisting of:
   a) SEQ ID No:1,
   b) a fragment of at least 10 contiguous nucleotides from SEQ ID No:1 or from the complement of SEQ ID No:1,
   c) SEQ ID No:5,
   d) a fragment of at least 10 contiguous nucleotides from SEQ ID No:5 or from the complement of SEQ ID No:5,
   e) SEQ ID No:3, and
   f) a fragment of at least 10 contiguous nucleotides from SEQ ID No:3 or from the complement of SEQ ID No:3.

4. The nucleic acid molecule of claim 3 consisting of SEQ ID NO:1.

5. A recombinant expression vector comprising the nucleic acid molecule of claim 4.

6. A host cell comprising the recombinant expression vector of claim 5.

7. The nucleic acid molecule of claim 3 which is a fragment of at least 10 contiguous nucleotides from SEQ ID No:1 or from the complement of SEQ ID No:1.

8. The nucleic acid molecule of claim 7 which is a fragment of 12 to 150 contiguous nucleotides from SEQ ID No:1 or from the complement of SEQ ID. No:1.

9. The nucleic acid molecule of claim 3 consisting of SEQ ID NO:3.

10. A recombinant expression vector comprising the nucleic acid molecule of claim 9.

11. A host cell comprising the recombinant expression vector of claim 10.

12. The nucleic acid molecule of claim 3 which is a fragment of at least 10 contiguous nucleotides from SEQ ID No:3 or from the complement of SEQ ID No:3.

13. The nucleic acid molecule of claim 12 which is a fragment of 12 to 150 contiguous nucleotides from SEQ ID No:3 or from the complement of SEQ ID No:3.

14. The nucleic acid molecule of claim 3 consisting of SEQ ID NO:5.

15. A recombinant expression vector comprising the nucleic acid molecule of claim 14.

16. A host cell comprising the recombinant expression vector of claim 15.

17. The nucleic acid molecule of claim 3 which is a fragment of at least 10 contiguous nucleotides from SEQ ID No:5 or from the complement of SEQ ID No:5.

18. The nucleic acid molecule of claim 17 which is a fragment of 12 to 150 contiguous nucleotides from SEQ ID No:5 or from the complement of SEQ ID No:5.

* * * * *

SEQUENCE LISTING ( 1 ) GENERAL INFORMATION:

( i i i ) NUMBER OF SEQUENCES: 25

( 2 ) INFORMATION FOR SEQ ID NO:1:

( i ) SEQUENCE CHARACTERISTICS:
        ( A ) LENGTH: 1613 base pairs
        ( B ) TYPE: nucleic acid
        ( C ) STRANDEDNESS: double
        ( D ) TOPOLOGY: both ( i i ) MOLECULE TYPE: cDNA ( i x ) FEATURE:
        ( A ) NAME/KEY: CDS
        ( B ) LOCATION: 362..1333

( x i ) SEQUENCE DESCRIPTION: SEQ ID NO:1:

-continued

```
GCGCAAGACC GGTTCAACCA GGAGCTGCAG CGCAGGCTGG CTGGGTCGGT GTGGAACAGT      60
GGCGGCTGCC GCAGCTGTAT CTCGACGAGC ACGCAAGAAC ACCGTGCTCT GGTGCGGCTA     120
CACCTGGCAA TACTGGCTGA CCACCCGCTC GGTCAACCCC GCCGAGTACC GGTTCTTCGG     180
GATCGGCAAC GGTTTGTCGA CGACCGCGCG ACGGTCGCTG CGGCGAACTA GCCGGCGAAA     240
CAGGCGAGCG GATTCGCGAC ACGCAAACAC AACTTCTTGT GTTGCAGTAC CTTGTCGGAC     300
CCCAGGGGTA GTGTTTGAGG CCTAGCAAGG CAGCTTGTTG TCCTGGTGAA GTGGGGTTCT     360
```

| | | | | | | | | | | | | | | | | |
|---|---|---|---|---|---|---|---|---|---|---|---|---|---|---|---|---|
| G | GTG | ACT | GGA | AAC | GCA | AAG | CTA | ATT | GAT | CGA | GTC | TCA | GCG | ATC | AAC | 406 |
| | Val | Thr | Gly | Asn | Ala | Lys | Leu | Ile | Asp | Arg | Val | Ser | Ala | Ile | Asn | |
| | 1 | | | | 5 | | | | | 10 | | | | | 15 | |

| TGG | AAC | CGA | CTG | CAA | GAT | GAG | AAG | GAC | GCC | GAG | GTC | TGG | GAT | CGG | CTG | 454 |
|---|---|---|---|---|---|---|---|---|---|---|---|---|---|---|---|---|
| Trp | Asn | Arg | Leu | Gln | Asp | Glu | Lys | Asp | Ala | Glu | Val | Trp | Asp | Arg | Leu | |
| | | | | 20 | | | | | 25 | | | | | 30 | | |

| ACC | GGA | AAC | TTC | TGG | CTG | CCC | GAG | AAG | GTG | CCG | GTG | TCC | AAT | GAC | ATC | 502 |
|---|---|---|---|---|---|---|---|---|---|---|---|---|---|---|---|---|
| Thr | Gly | Asn | Phe | Trp | Leu | Pro | Glu | Lys | Val | Pro | Val | Ser | Asn | Asp | Ile | |
| | | | 35 | | | | | 40 | | | | | 45 | | | |

| CCG | TCG | TGG | GGC | ACC | CTG | ACC | GCC | GGC | GAG | AAG | CAA | CTA | ACC | ATG | CGG | 550 |
|---|---|---|---|---|---|---|---|---|---|---|---|---|---|---|---|---|
| Pro | Ser | Trp | Gly | Thr | Leu | Thr | Ala | Gly | Glu | Lys | Gln | Leu | Thr | Met | Arg | |
| | | 50 | | | | | 55 | | | | | 60 | | | | |

| GTC | TTC | ACC | GGC | CTG | ACC | ATG | CTG | GAC | ACC | ATC | CAG | GGC | ACC | GTT | GGT | 598 |
|---|---|---|---|---|---|---|---|---|---|---|---|---|---|---|---|---|
| Val | Phe | Thr | Gly | Leu | Thr | Met | Leu | Asp | Thr | Ile | Gln | Gly | Thr | Val | Gly | |
| | 65 | | | | | 70 | | | | | 75 | | | | | |

| GCG | GTC | AGC | CTG | ATT | CCC | GAC | GCG | CTG | ACT | CCG | CAT | GAG | GAG | GCG | GTG | 646 |
|---|---|---|---|---|---|---|---|---|---|---|---|---|---|---|---|---|
| Ala | Val | Ser | Leu | Ile | Pro | Asp | Ala | Leu | Thr | Pro | His | Glu | Glu | Ala | Val | |
| 80 | | | | | 85 | | | | | 90 | | | | | 95 | |

| TTG | ACC | AAC | ATC | GCG | TTC | ATG | GAG | TCC | GTG | CAC | GCC | AAG | AGC | TAC | AGC | 694 |
|---|---|---|---|---|---|---|---|---|---|---|---|---|---|---|---|---|
| Leu | Thr | Asn | Ile | Ala | Phe | Met | Glu | Ser | Val | His | Ala | Lys | Ser | Tyr | Ser | |
| | | | | 100 | | | | | 105 | | | | | 110 | | |

| CAG | ATC | TTC | TCC | ACG | CTG | TGT | TCC | ACC | GCC | GAG | ATC | GAC | GAC | GCC | TTC | 742 |
|---|---|---|---|---|---|---|---|---|---|---|---|---|---|---|---|---|
| Gln | Ile | Phe | Ser | Thr | Leu | Cys | Ser | Thr | Ala | Glu | Ile | Asp | Asp | Ala | Phe | |
| | | | 115 | | | | | 120 | | | | | 125 | | | |

| CGC | TGG | TCG | GAG | GAA | AAT | CGC | AAT | CTG | CAG | CGC | AAG | GCC | GAG | ATC | GTG | 790 |
|---|---|---|---|---|---|---|---|---|---|---|---|---|---|---|---|---|
| Arg | Trp | Ser | Glu | Glu | Asn | Arg | Asn | Leu | Gln | Arg | Lys | Ala | Glu | Ile | Val | |
| | | 130 | | | | | 135 | | | | | 140 | | | | |

| CTG | CAG | TAC | TAC | CGC | GGC | GAC | GAG | CCG | CTC | AAG | CGC | AAG | GTG | GCC | TCC | 838 |
|---|---|---|---|---|---|---|---|---|---|---|---|---|---|---|---|---|
| Leu | Gln | Tyr | Tyr | Arg | Gly | Asp | Glu | Pro | Leu | Lys | Arg | Lys | Val | Ala | Ser | |
| | 145 | | | | | 150 | | | | | 155 | | | | | |

| ACC | CTG | CTG | GAG | AGC | TTC | CTG | TTC | TAC | TCT | GGG | TTC | TAC | CTG | CCG | ATG | 886 |
|---|---|---|---|---|---|---|---|---|---|---|---|---|---|---|---|---|
| Thr | Leu | Leu | Glu | Ser | Phe | Leu | Phe | Tyr | Ser | Gly | Phe | Tyr | Leu | Pro | Met | |
| 160 | | | | | 165 | | | | | 170 | | | | | 175 | |

| TAC | TGG | TCG | AGT | CGG | GCC | AAG | TTG | ACC | AAC | ACC | GCC | GAC | ATG | ATC | CGG | 934 |
|---|---|---|---|---|---|---|---|---|---|---|---|---|---|---|---|---|
| Tyr | Trp | Ser | Ser | Arg | Ala | Lys | Leu | Thr | Asn | Thr | Ala | Asp | Met | Ile | Arg | |
| | | | | 180 | | | | | 185 | | | | | 190 | | |

| CTG | ATC | ATC | CGC | GAC | GAG | GCC | GTG | CAC | GGT | TAC | TAC | ATC | GGC | TAT | AAG | 982 |
|---|---|---|---|---|---|---|---|---|---|---|---|---|---|---|---|---|
| Leu | Ile | Ile | Arg | Asp | Glu | Ala | Val | His | Gly | Tyr | Tyr | Ile | Gly | Tyr | Lys | |
| | | | 195 | | | | | 200 | | | | | 205 | | | |

| TTC | CAG | CGT | GGT | CTG | GCG | TTG | GTT | GAC | GAC | GTC | ACG | CGC | GCC | GAG | CTC | 1030 |
|---|---|---|---|---|---|---|---|---|---|---|---|---|---|---|---|---|
| Phe | Gln | Arg | Gly | Leu | Ala | Leu | Val | Asp | Asp | Val | Thr | Arg | Ala | Glu | Leu | |
| | | 210 | | | | | 215 | | | | | 220 | | | | |

| AAG | GAC | TAC | ACC | TAC | GAG | CTA | CTG | TTC | GAG | CTC | TAC | GAC | AAC | GAG | GTG | 1078 |
|---|---|---|---|---|---|---|---|---|---|---|---|---|---|---|---|---|
| Lys | Asp | Tyr | Thr | Tyr | Glu | Leu | Leu | Phe | Glu | Leu | Tyr | Asp | Asn | Glu | Val | |
| | 225 | | | | | 230 | | | | | 235 | | | | | |

| GAA | TAC | ACC | CAG | GAC | CTC | TAC | GAC | GAG | GTC | GGG | CTA | ACC | GAG | GAC | GTC | 1126 |
|---|---|---|---|---|---|---|---|---|---|---|---|---|---|---|---|---|
| Glu | Tyr | Thr | Gln | Asp | Leu | Tyr | Asp | Glu | Val | Gly | Leu | Thr | Glu | Asp | Val | |
| 240 | | | | | 245 | | | | | 250 | | | | | 255 | |

| AAG | AAG | TTC | TTG | CGC | TAC | AAC | GCC | AAC | AAG | GCG | CTG | ATG | AAC | CTC | GGC | 1174 |
|---|---|---|---|---|---|---|---|---|---|---|---|---|---|---|---|---|
| Lys | Lys | Phe | Leu | Arg | Tyr | Asn | Ala | Asn | Lys | Ala | Leu | Met | Asn | Leu | Gly | |
| | | | | 260 | | | | | 265 | | | | | 270 | | |

```
TAT  GAG  GCG  CTG  TTC  CCC  CGC  GAT  GAG  ACC  GAC  GTG  AAC  CCG  GCC  ATC            1222
Tyr  Glu  Ala  Leu  Phe  Pro  Arg  Asp  Glu  Thr  Asp  Val  Asn  Pro  Ala  Ile
               275                      280                      285

CTG  TCG  GCG  CTG  TCA  CCC  AAC  GCC  GAC  GAG  AAC  CAT  GAC  TTC  TTC  TCC            1270
Leu  Ser  Ala  Leu  Ser  Pro  Asn  Ala  Asp  Glu  Asn  His  Asp  Phe  Phe  Ser
               290                      295                      300

GGA  TCC  GGG  TCG  AGC  TAT  GTG  ATC  GGC  AAG  GCG  GTC  GTC  ACC  GAG  GAC            1318
Gly  Ser  Gly  Ser  Ser  Tyr  Val  Ile  Gly  Lys  Ala  Val  Val  Thr  Glu  Asp
          305                      310                      315

GAT  GAC  TGG  GAC  TTC  TAGAGTCGCG  GAAATCAGGC  CATTGTTCGG  CCGGACTCCG                    1373
Asp  Asp  Trp  Asp  Phe
320

AGGCCAGCAA  ACACTGACCT  GATGCGGTAA  CTAGCTACTA  CGTCGAGTTG  ATCTTTGACA                     1433

TGGGCGGACC  GTTCGATGCG  GACGCGGAGG  CCATTTCGAC  GAGGTTGCCG  AGGCATTCGC                     1493

CAAGCTCACC  AATGTGGACC  GCGACGTCGG  CGTAGACCTG  GAGAAGGAGC  TGTGCAGTGA                     1553

CGGTGGAGGC  CGATGACCGC  TCTCGGACGC  GCTCGTCACA  AGGCGTTTGT  TGCCGCGCGT                     1613
```

( 2 ) INFORMATION FOR SEQ ID NO:2:

( i ) SEQUENCE CHARACTERISTICS:
        ( A ) LENGTH: 324 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Val  Thr  Gly  Asn  Ala  Lys  Leu  Ile  Asp  Arg  Val  Ser  Ala  Ile  Asn  Trp
 1                  5                        10                       15

Asn  Arg  Leu  Gln  Asp  Glu  Lys  Asp  Ala  Glu  Val  Trp  Asp  Arg  Leu  Thr
               20                       25                       30

Gly  Asn  Phe  Trp  Leu  Pro  Glu  Lys  Val  Pro  Val  Ser  Asn  Asp  Ile  Pro
               35                       40                       45

Ser  Trp  Gly  Thr  Leu  Thr  Ala  Gly  Glu  Lys  Gln  Leu  Thr  Met  Arg  Val
          50                       55                       60

Phe  Thr  Gly  Leu  Thr  Met  Leu  Asp  Thr  Ile  Gln  Gly  Thr  Val  Gly  Ala
 65                      70                       75                       80

Val  Ser  Leu  Ile  Pro  Asp  Ala  Leu  Thr  Pro  His  Glu  Glu  Ala  Val  Leu
               85                       90                       95

Thr  Asn  Ile  Ala  Phe  Met  Glu  Ser  Val  His  Ala  Lys  Ser  Tyr  Ser  Gln
               100                      105                      110

Ile  Phe  Ser  Thr  Leu  Cys  Ser  Thr  Ala  Glu  Ile  Asp  Asp  Ala  Phe  Arg
               115                      120                      125

Trp  Ser  Glu  Glu  Asn  Arg  Asn  Leu  Gln  Arg  Lys  Ala  Glu  Ile  Val  Leu
          130                      135                      140

Gln  Tyr  Tyr  Arg  Gly  Asp  Glu  Pro  Leu  Lys  Arg  Lys  Val  Ala  Ser  Thr
145                      150                      155                      160

Leu  Leu  Glu  Ser  Phe  Leu  Phe  Tyr  Ser  Gly  Phe  Tyr  Leu  Pro  Met  Tyr
               165                      170                      175

Trp  Ser  Ser  Arg  Ala  Lys  Leu  Thr  Asn  Thr  Ala  Asp  Met  Ile  Arg  Leu
               180                      185                      190

Ile  Ile  Arg  Asp  Glu  Ala  Val  His  Gly  Tyr  Tyr  Ile  Gly  Tyr  Lys  Phe
          195                      200                      205

Gln  Arg  Gly  Leu  Ala  Leu  Val  Asp  Asp  Val  Thr  Arg  Ala  Glu  Leu  Lys
          210                      215                      220

Asp  Tyr  Thr  Tyr  Glu  Leu  Leu  Phe  Glu  Leu  Tyr  Asp  Asn  Glu  Val  Glu
225                      230                      235                      240
```

| Tyr | Thr | Gln | Asp | Leu | Tyr | Asp | Glu | Val | Gly | Leu | Thr | Glu | Asp | Val | Lys |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Lys | Phe | Leu | Arg | Tyr | Asn | Ala | Asn | Lys | Ala | Leu | Met | Asn | Leu | Gly | Tyr |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Glu | Ala | Leu | Phe | Pro | Arg | Asp | Glu | Thr | Asp | Val | Asn | Pro | Ala | Ile | Leu |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Ser | Ala | Leu | Ser | Pro | Asn | Ala | Asp | Glu | Asn | His | Asp | Phe | Phe | Ser | Gly |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Ser | Gly | Ser | Ser | Tyr | Val | Ile | Gly | Lys | Ala | Val | Val | Thr | Glu | Asp | Asp |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Asp | Trp | Asp | Phe |
|-----|-----|-----|-----|

(2) INFORMATION FOR SEQ ID NO:3:

(i) SEQUENCE CHARACTERISTICS:
        (A) LENGTH: 3107 base pairs
        (B) TYPE: nucleic acid
        (C) STRANDEDNESS: double
        (D) TOPOLOGY: both (ii) MOLECULE TYPE: cDNA (ix) FEATURE:
        (A) NAME/KEY: CDS
        (B) LOCATION: 207..2909

(xi) SEQUENCE DESCRIPTION: SEQ ID NO:3:

```
GATCTCCGAG  CGTCCTGAGC  GGCCCGTTTG  AGCCTTTGGT  GTGGTAATCT  GTTTGCAGCC      60

GGTTTGCGCA  GGCCCGCCCT  AGAGTGCGAG  ATTGTCAGTT  GCCGACAGGC  GAGGGAAACG     120

GCGGCGTACC  GGAATTCACC  TGGGATTCGG  CAGTCGGCCG  CGTCCTCTAC  CTACCGGGGC     180

GGTCTCGATA  GGGGCCGGGA  TAAGAG ATG GAG CGT GGG GCG CAG TTG GCT GAC         233
                              Met Glu Arg Gly Ala Gln Leu Ala Asp
                              325                 330
```

| CCG | AAA | ACG | AAG | GGC | CGT | GGC | AGC | GGC | GGC | AAT | GGC | AGC | GGC | CGG | CGA | 281 |
|-----|-----|-----|-----|-----|-----|-----|-----|-----|-----|-----|-----|-----|-----|-----|-----|-----|
| Pro | Lys | Thr | Lys | Gly | Arg | Gly | Ser | Gly | Gly | Asn | Gly | Ser | Gly | Arg | Arg |     |
|     | 335 |     |     |     | 340 |     |     |     |     | 345 |     |     |     |     |     |     |

| CTG | GTC | ATC | GTC | GAG | TCG | CCC | ACC | AAG | GCG | CGC | AAG | CTG | GCC | TCC | TAC | 329 |
|-----|-----|-----|-----|-----|-----|-----|-----|-----|-----|-----|-----|-----|-----|-----|-----|-----|
| Leu | Val | Ile | Val | Glu | Ser | Pro | Thr | Lys | Ala | Arg | Lys | Leu | Ala | Ser | Tyr |     |
| 350 |     |     |     |     | 355 |     |     |     |     | 360 |     |     |     |     | 365 |     |

| CTG | GGC | TCT | GGC | TAC | ATC | GTC | GAG | TCC | TCC | CGG | GGG | CAC | ATC | CGT | GAC | 377 |
|-----|-----|-----|-----|-----|-----|-----|-----|-----|-----|-----|-----|-----|-----|-----|-----|-----|
| Leu | Gly | Ser | Gly | Tyr | Ile | Val | Glu | Ser | Ser | Arg | Gly | His | Ile | Arg | Asp |     |
|     |     |     |     | 370 |     |     |     |     | 375 |     |     |     |     | 380 |     |     |

| TTG | CGC | GGG | CCG | CGT | CGA | TGT | ACC | CGC | AAG | TAC | AAG | TCG | CAG | CCG | TGG | 425 |
|-----|-----|-----|-----|-----|-----|-----|-----|-----|-----|-----|-----|-----|-----|-----|-----|-----|
| Leu | Arg | Gly | Pro | Arg | Arg | Cys | Thr | Arg | Lys | Tyr | Lys | Ser | Gln | Pro | Trp |     |
|     |     |     | 385 |     |     |     |     | 390 |     |     |     |     | 395 |     |     |     |

| GCG | CGG | CTC | GGG | GTC | AAC | GTC | GAC | GCC | GAC | TTC | GAA | CCG | CTC | TAC | ATC | 473 |
|-----|-----|-----|-----|-----|-----|-----|-----|-----|-----|-----|-----|-----|-----|-----|-----|-----|
| Ala | Arg | Leu | Gly | Val | Asn | Val | Asp | Ala | Asp | Phe | Glu | Pro | Leu | Tyr | Ile |     |
|     |     |     | 400 |     |     |     |     | 405 |     |     |     |     | 410 |     |     |     |

| ATC | AGC | CCG | GAG | AAA | CGG | AGC | ACC | GTC | AGC | GAG | CTC | AGG | GGC | CTG | CTC | 521 |
|-----|-----|-----|-----|-----|-----|-----|-----|-----|-----|-----|-----|-----|-----|-----|-----|-----|
| Ile | Ser | Pro | Glu | Lys | Arg | Ser | Thr | Val | Ser | Glu | Leu | Arg | Gly | Leu | Leu |     |
|     | 415 |     |     |     |     | 420 |     |     |     |     | 425 |     |     |     |     |     |

| AAA | GAC | GTG | GAC | GAG | CTG | TAT | CTG | GCC | ACG | GAT | GGG | GAC | CGT | GAG | GGC | 569 |
|-----|-----|-----|-----|-----|-----|-----|-----|-----|-----|-----|-----|-----|-----|-----|-----|-----|
| Lys | Asp | Val | Asp | Glu | Leu | Tyr | Leu | Ala | Thr | Asp | Gly | Asp | Arg | Glu | Gly |     |
| 430 |     |     |     |     | 435 |     |     |     |     | 440 |     |     |     |     | 445 |     |

| GAA | GCT | ATT | GCC | TGG | CAT | CTG | CTG | GAA | ACC | CTC | AAA | CCG | CGC | ATA | CCG | 617 |
|-----|-----|-----|-----|-----|-----|-----|-----|-----|-----|-----|-----|-----|-----|-----|-----|-----|
| Glu | Ala | Ile | Ala | Trp | His | Leu | Leu | Glu | Thr | Leu | Lys | Pro | Arg | Ile | Pro |     |
|     |     |     |     | 450 |     |     |     |     | 455 |     |     |     |     | 460 |     |     |

| GTA | AAG | CGG | ATG | GTC | TTC | CAC | GAG | ATC | ACC | GAA | CCG | GCG | ATC | CGC | GCC | 665 |
|-----|-----|-----|-----|-----|-----|-----|-----|-----|-----|-----|-----|-----|-----|-----|-----|-----|
| Val | Lys | Arg | Met | Val | Phe | His | Glu | Ile | Thr | Glu | Pro | Ala | Ile | Arg | Ala |     |
|     |     |     | 465 |     |     |     |     | 470 |     |     |     |     | 475 |     |     |     |

| | | | | | | | | | | | | | | | | |
|---|---|---|---|---|---|---|---|---|---|---|---|---|---|---|---|---|
| GCC | GCC | GAG | CAT | CCC | CGC | GAC | CTA | GAC | ATC | GAC | CTG | GTC | GAC | GCG | CAG | 713 |
| Ala | Ala | Glu 480 | His | Pro | Arg | Asp | Leu | Asp 485 | Ile | Asp | Leu | Val 490 | Asp | Ala | Gln | |
| GAG | ACC | CGG | CGC | ATC | CTG | GAC | CGG | CTG | TAC | GGC | TAC | GAA | GTC | AGC | CCA | 761 |
| Glu | Thr 495 | Arg | Arg | Ile | Leu | Asp | Arg 500 | Leu | Tyr | Gly | Tyr | Glu 505 | Val | Ser | Pro | |
| GTG | CTG | TGG | AAG | AAG | GTC | GCC | CCC | AAG | TTG | TCG | GCG | GGC | CGG | GTG | CAG | 809 |
| Val 510 | Leu | Trp | Lys | Lys | Val 515 | Ala | Pro | Lys | Leu | Ser 520 | Ala | Gly | Arg | Val | Gln 525 | |
| TCG | GTG | GCC | ACC | CGC | ATC | ATC | GTG | GCG | CGC | GAA | CGC | GAC | CGC | ATG | GCG | 857 |
| Ser | Val | Ala | Thr | Arg 530 | Ile | Ile | Val | Ala | Arg 535 | Glu | Arg | Asp | Arg | Met 540 | Ala | |
| TTC | CGC | AGC | GCG | GCC | TAC | TGG | GAC | ATC | CTT | GCC | AAG | CTG | GAT | GCC | AGC | 905 |
| Phe | Arg | Ser | Ala 545 | Ala | Tyr | Trp | Asp | Ile 550 | Leu | Ala | Lys | Leu 555 | Asp | Ala | Ser | |
| GTG | TCC | GAC | CCG | GAC | GCC | GCG | CCG | CCC | ACC | TTC | AGC | GCC | CGG | CTG | ACG | 953 |
| Val | Ser | Asp 560 | Pro | Asp | Ala | Ala | Pro 565 | Pro | Thr | Phe | Ser | Ala 570 | Arg | Leu | Thr | |
| GCC | GTG | GCT | GGC | CGG | CGG | GTG | GCC | ACT | GGC | GCG | ATT | TCG | ACT | CGC | TGG | 1001 |
| Ala | Val | Ala 575 | Gly | Arg | Arg | Val | Ala 580 | Thr | Gly | Ala | Ile | Ser 585 | Thr | Arg | Trp | |
| GCA | CGC | TGC | GCA | AAG | GCG | ACG | AAG | TCA | TTG | TGC | TCG | ACG | AGG | GGA | GCG | 1049 |
| Ala | Arg 590 | Cys | Ala | Lys | Ala 595 | Thr | Lys | Ser | Leu | Cys 600 | Ser | Thr | Arg | Gly | Ala 605 | |
| CGA | CCG | CGT | TGG | CCG | GCG | GGC | CTG | GAT | GGC | ACG | CAG | CTG | ACC | GTG | GCC | 1097 |
| Arg | Pro | Arg | Trp | Pro 610 | Ala | Gly | Leu | Asp | Gly 615 | Thr | Gln | Leu | Thr | Val 620 | Ala | |
| TCG | GCC | GAG | GAG | AAG | CCC | TAC | GCC | CGG | CGC | CCG | TAC | CCG | CCG | TTC | ATG | 1145 |
| Ser | Ala | Glu | Glu 625 | Lys | Pro | Tyr | Ala | Arg 630 | Arg | Pro | Tyr | Pro | Pro 635 | Phe | Met | |
| ACC | TCC | ACG | CTG | CAG | CAA | GAG | GCC | AGC | CGC | AAG | CTG | CGG | TTC | TCC | GCC | 1193 |
| Thr | Ser | Thr 640 | Leu | Gln | Gln | Glu | Ala 645 | Ser | Arg | Lys | Leu | Arg 650 | Phe | Ser | Ala | |
| GAG | CGG | ACG | ATG | AGC | ATC | GCC | CAG | CGG | CTG | TAC | GAA | AAC | GGC | TAC | ATC | 1241 |
| Glu | Arg | Thr 655 | Met | Ser | Ile | Ala | Gln 660 | Arg | Leu | Tyr | Glu | Asn 665 | Gly | Tyr | Ile | |
| ACC | TAT | ATG | CGT | ACC | GAC | TCC | ACC | ACG | CTG | TCG | GAG | TCG | GCG | ATC | AAC | 1289 |
| Thr 670 | Tyr | Met | Arg | Thr | Asp 675 | Ser | Thr | Thr | Leu | Ser 680 | Glu | Ser | Ala | Ile | Asn 685 | |
| GCC | GCA | CGT | ACC | CAG | GCG | CGC | CAG | CTC | TAC | GGC | GAC | GGA | GTA | CGT | CGG | 1337 |
| Ala | Ala | Arg | Thr | Gln 690 | Ala | Arg | Gln | Leu | Tyr 695 | Gly | Asp | Gly | Val | Arg 700 | Arg | |
| CCG | GCG | CCG | CGC | CAA | TAC | ACC | CGC | AAG | GTG | AAG | AAC | GCC | CAG | GAA | GCG | 1385 |
| Pro | Ala | Pro | Arg 705 | Gln | Tyr | Thr | Arg | Lys 710 | Val | Lys | Asn | Ala | Gln 715 | Glu | Ala | |
| CAC | GAG | GCT | ATC | CGG | CCC | GCC | GGT | GAA | ACG | TTT | GCC | ACC | CCG | GAC | GCG | 1433 |
| His | Glu | Ala | Ile 720 | Arg | Pro | Ala | Gly | Glu 725 | Thr | Phe | Ala | Thr | Pro 730 | Asp | Ala | |
| GTG | CGT | CGC | GAA | CTC | GAC | GGT | CCC | AAC | ATT | GAT | GAT | TTC | CGG | CTC | TAT | 1481 |
| Val | Arg 735 | Arg | Glu | Leu | Asp | Gly 740 | Pro | Asn | Ile | Asp | Asp 745 | Phe | Arg | Leu | Tyr | |
| GAG | CTG | ATT | TGG | CAA | CGC | ACC | GTA | GCC | TCG | CAG | ATG | GCC | GAT | GCG | CGG | 1529 |
| Glu | Leu | Ile | Trp | Gln 755 | Arg | Thr | Val | Ala | Ser 760 | Gln | Met | Ala | Asp | Ala 765 | Arg | |
| | | | | | | | | | | | | | | | | |
| Glu 750 | | | | | | | | | | | | | | | | |
| GGC | ATG | ACG | CTG | AGC | CTG | CGG | ATC | ACT | GGC | ATG | TCG | GGG | CAC | CAG | GAG | 1577 |
| Gly | Met | Thr | Leu | Ser 770 | Leu | Arg | Ile | Thr | Gly 775 | Met | Ser | Gly | His | Gln 780 | Glu | |
| GTG | GTG | TTC | TCC | GCG | ACC | GGA | CGC | ACC | TTG | ACG | TTC | CCG | GGC | TTC | CTC | 1625 |
| Val | Val | Phe | Ser 785 | Ala | Thr | Gly | Arg | Thr 790 | Leu | Thr | Phe | Pro | Gly 795 | Phe | Leu | |

```
AAG GCC TAC GTG GAG ACG GTG GAC GAG CTG GTC GGC GGC GAG GCT GAC    1673
Lys Ala Tyr Val Glu Thr Val Asp Glu Leu Val Gly Gly Glu Ala Asp
    800                 805                 810

GAT GCC GAG CGG CGA CTG CCC CAT CTG ACC CCG GGT CAA CGG TTG GAC    1721
Asp Ala Glu Arg Arg Leu Pro His Leu Thr Pro Gly Gln Arg Leu Asp
815                 820                 825

ATC GTC GAG TTG ACC CCA GAC GGC CAT GCC ACC AAC CCG CCG GCC CGC    1769
Ile Val Glu Leu Thr Pro Asp Gly His Ala Thr Asn Pro Pro Ala Arg
830                 835                 840                 845

TAC ACC GAG GCG TCG CTG GTC AAA GCG CTC GAG GAG CTG GGC ATC GGC    1817
Tyr Thr Glu Ala Ser Leu Val Lys Ala Leu Glu Glu Leu Gly Ile Gly
                850                 855                 860

CGC CCG TCG ACC TAC TCG TCG ATC ATC AAG ACC ATC CAG GAT CGC GGC    1865
Arg Pro Ser Thr Tyr Ser Ser Ile Ile Lys Thr Ile Gln Asp Arg Gly
            865                 870                 875

TAC GTG CAC AAG AAG GGC AGT GCA CTG GTG CCG TCA TGG GTG GCG TTC    1913
Tyr Val His Lys Lys Gly Ser Ala Leu Val Pro Ser Trp Val Ala Phe
        880                 885                 890

GCG GTA ACC GGT CTG CTC GAG CAG CAT TTC GGT CGG CTC GTC GAC TAC    1961
Ala Val Thr Gly Leu Leu Glu Gln His Phe Gly Arg Leu Val Asp Tyr
895                 900                 905

GAC TTC ACC GCG GCG ATG GAA GAC GAG CTC GAC GAG ATC GCC GCC GGC    2009
Asp Phe Thr Ala Ala Met Glu Asp Glu Leu Asp Glu Ile Ala Ala Gly
910                 915                 920                 925

AAC GAG CGC CGC ACC AAC TGG CTC AAC AAC TTC TAC TTT GGT GGC GAT    2057
Asn Glu Arg Arg Thr Asn Trp Leu Asn Asn Phe Tyr Phe Gly Gly Asp
                930                 935                 940

CAC GGT GTG CCC GAT TCG GTA GCC CGA TCG GGT GGC CTC AAG AAG CTT    2105
His Gly Val Pro Asp Ser Val Ala Arg Ser Gly Gly Leu Lys Lys Leu
            945                 950                 955

GTC GGG ATC AAT CTC GAG GGC ATC GAC GCA CGA GAA GTA AAC TCT ATC    2153
Val Gly Ile Asn Leu Glu Gly Ile Asp Ala Arg Glu Val Asn Ser Ile
        960                 965                 970

AAG CTT TTT GAC GAC ACC CAC GGA CGC CCC ATA TAT GTT CGG GTG GGC    2201
Lys Leu Phe Asp Asp Thr His Gly Arg Pro Ile Tyr Val Arg Val Gly
975                 980                 985

AAG AAC GGT CCC TAC CTG GAA CGT TTG GTG GCC GGC GAC ACC GGT GAG    2249
Lys Asn Gly Pro Tyr Leu Glu Arg Leu Val Ala Gly Asp Thr Gly Glu
990                 995                 1000                1005

CCC ACG CCG CAG CGG GCC AAC CTC AGC GAC TCG ATT ACC CCG GAC GAG    2297
Pro Thr Pro Gln Arg Ala Asn Leu Ser Asp Ser Ile Thr Pro Asp Glu
                1010                1015                1020

CTG ACT CTA CAG GTG GCC GAA GAG CTC TTT GCC ACA CCG CAA CAG GGA    2345
Leu Thr Leu Gln Val Ala Glu Glu Leu Phe Ala Thr Pro Gln Gln Gly
            1025                1030                1035

CGG ACT TTG GGC TTG GAC CCA GAA ACC GGC CAC GAG ATC GTG GCC AGG    2393
Arg Thr Leu Gly Leu Asp Pro Glu Thr Gly His Glu Ile Val Ala Arg
        1040                1045                1050

GAA GGC CGG TTT GGG CCG TAT GTG ACC GAG ATC CTG CCG GAG CCT GCG    2441
Glu Gly Arg Phe Gly Pro Tyr Val Thr Glu Ile Leu Pro Glu Pro Ala
    1055                1060                1065

GCT GAT GCG GCC GCG GCC GCT CAG GGA GTC AAG AAA CGC CAG AAG GCC    2489
Ala Asp Ala Ala Ala Ala Ala Gln Gly Val Lys Lys Arg Gln Lys Ala
1070                1075                1080                1085

GCC GGG CCC AAA CCG CGC ACC GGT TCG TTG CTG CGG AGC ATG GAC CTA    2537
Ala Gly Pro Lys Pro Arg Thr Gly Ser Leu Leu Arg Ser Met Asp Leu
                1090                1095                1100

CAG ACG GTC ACC CTC GAA GAC GCG CTG AGG CTG CTG TCA CTG CCG CGC    2585
Gln Thr Val Thr Leu Glu Asp Ala Leu Arg Leu Leu Ser Leu Pro Arg
            1105                1110                1115
```

```
GTG  GTC  GGA  GTG  GAC  CCC  GCC  TCG  GTC  GAG  GAG  ATC  ACC  GCG  CAG  AAC    2633
Val  Val  Gly  Val  Asp  Pro  Ala  Ser  Val  Glu  Glu  Ile  Thr  Ala  Gln  Asn
          1120                1125                          1130

GGG  CGC  TAC  GGA  CCG  TAT  CTA  AAG  CGC  GGC  AAC  GAT  TCT  CGA  TCA  CTG    2681
Gly  Arg  Tyr  Gly  Pro  Tyr  Leu  Lys  Arg  Gly  Asn  Asp  Ser  Arg  Ser  Leu
     1135                     1140                          1145

GTC  ACC  GAA  GAC  CAG  ATA  TTC  ACC  ATC  ACG  CTC  GAC  GAA  GCC  CTG  AAG    2729
Val  Thr  Glu  Asp  Gln  Ile  Phe  Thr  Ile  Thr  Leu  Asp  Glu  Ala  Leu  Lys
1150                     1155                     1160                     1165

ATC  TAC  GCA  GAG  CCG  AAA  CGT  CGT  GGC  CGG  CAA  AGC  GCT  TCG  GCT  CCG    2777
Ile  Tyr  Ala  Glu  Pro  Lys  Arg  Arg  Gly  Arg  Gln  Ser  Ala  Ser  Ala  Pro
                    1170                     1175                     1180

GCC  TGC  GCG  AGC  TGG  GAA  CAG  ATC  CGG  CGT  CGG  GCA  AGC  CAA  TGG  TCA    2825
Ala  Cys  Ala  Ser  Trp  Glu  Gln  Ile  Arg  Arg  Arg  Ala  Ser  Gln  Trp  Ser
               1185                          1190                     1195

TCA  AGG  ACG  GCC  GAT  TCG  GGC  CGT  ACG  TCA  CCG  ACG  GTG  AGA  CCA  ATG    2873
Ser  Arg  Thr  Ala  Asp  Ser  Gly  Arg  Thr  Ser  Pro  Thr  Val  Arg  Pro  Met
          1200                          1205                     1210

CCA  GCC  TGC  GTA  AGG  GCG  ACG  ACG  TGG  CTT  CCA  TAA  CCGACGAGCG              2919
Pro  Ala  Cys  Val  Arg  Ala  Thr  Thr  Trp  Leu  Pro   *
          1215                     1220                  1225

CGCCGCCGAG  CTGTTGGCCG  ATCGCCGAGC  CGGGGTCCGG  CAAAACGGCC  AGCCAGGAAA             2979

GCTGCCCGGA  AGGTGCCGGC  GAAGAAGGCA  GCCAAGGCGA  CTAGCCGCGT  ACTTCGCTGG             3039

AAACCTCTTC  GGGTGCAGCC  AGATTCATTG  GCCTGGCTAG  TTGGGTGGTG  CAGCACGTCG             3099

CGGAGCTC                                                                            3107
```

( 2 ) INFORMATION FOR SEQ ID NO:4:

( i ) SEQUENCE CHARACTERISTICS:
        ( A ) LENGTH: 900 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met  Glu  Arg  Gly  Ala  Gln  Leu  Ala  Asp  Pro  Lys  Thr  Lys  Gly  Arg  Gly
 1                  5                    10                       15

Ser  Gly  Gly  Asn  Gly  Ser  Gly  Arg  Arg  Leu  Val  Ile  Val  Glu  Ser  Pro
               20                    25                       30

Thr  Lys  Ala  Arg  Lys  Leu  Ala  Ser  Tyr  Leu  Gly  Ser  Gly  Tyr  Ile  Val
          35                    40                       45

Glu  Ser  Ser  Arg  Gly  His  Ile  Arg  Asp  Leu  Arg  Gly  Pro  Arg  Arg  Cys
     50                    55                       60

Thr  Arg  Lys  Tyr  Lys  Ser  Gln  Pro  Trp  Ala  Arg  Leu  Gly  Val  Asn  Val
65             70                    75                            80

Asp  Ala  Asp  Phe  Glu  Pro  Leu  Tyr  Ile  Ile  Ser  Pro  Glu  Lys  Arg  Ser
               85                    90                       95

Thr  Val  Ser  Glu  Leu  Arg  Gly  Leu  Leu  Lys  Asp  Val  Asp  Glu  Leu  Tyr
               100                   105                      110

Leu  Ala  Thr  Asp  Gly  Asp  Arg  Glu  Gly  Glu  Ala  Ile  Ala  Trp  His  Leu
          115                   120                      125

Leu  Glu  Thr  Leu  Lys  Pro  Arg  Ile  Pro  Val  Lys  Arg  Met  Val  Phe  His
     130                      135                   140

Glu  Ile  Thr  Glu  Pro  Ala  Ile  Arg  Ala  Ala  Ala  Glu  His  Pro  Arg  Asp
145                 150                      155                           160

Leu  Asp  Ile  Asp  Leu  Val  Asp  Ala  Gln  Glu  Thr  Arg  Arg  Ile  Leu  Asp
```

-continued

|  |  |  | 165 |  |  |  |  | 170 |  |  |  |  | 175 |  |
|---|---|---|---|---|---|---|---|---|---|---|---|---|---|---|
| Arg | Leu | Tyr | Gly | Tyr | Glu | Val | Ser | Pro | Val | Leu | Trp | Lys | Lys | Val | Ala |
|  |  |  | 180 |  |  |  |  | 185 |  |  |  |  | 190 |  |
| Pro | Lys | Leu | Ser | Ala | Gly | Arg | Val | Gln | Ser | Val | Ala | Thr | Arg | Ile | Ile |
|  |  |  | 195 |  |  |  |  | 200 |  |  |  |  | 205 |  |
| Val | Ala | Arg | Glu | Arg | Asp | Arg | Met | Ala | Phe | Arg | Ser | Ala | Ala | Tyr | Trp |
|  |  |  | 210 |  |  |  |  | 215 |  |  |  |  | 220 |  |
| Asp | Ile | Leu | Ala | Lys | Leu | Asp | Ala | Ser | Val | Ser | Asp | Pro | Asp | Ala | Ala |
| 225 |  |  |  |  | 230 |  |  |  |  | 235 |  |  |  |  | 240 |
| Pro | Pro | Thr | Phe | Ser | Ala | Arg | Leu | Thr | Ala | Val | Ala | Gly | Arg | Arg | Val |
|  |  |  |  | 245 |  |  |  |  | 250 |  |  |  |  | 255 |  |
| Ala | Thr | Gly | Ala | Ile | Ser | Thr | Arg | Trp | Ala | Arg | Cys | Ala | Lys | Ala | Thr |
|  |  |  | 260 |  |  |  |  | 265 |  |  |  |  | 270 |  |
| Lys | Ser | Leu | Cys | Ser | Thr | Arg | Gly | Ala | Arg | Pro | Arg | Trp | Pro | Ala | Gly |
|  |  |  | 275 |  |  |  |  | 280 |  |  |  |  | 285 |  |
| Leu | Asp | Gly | Thr | Gln | Leu | Thr | Val | Ala | Ser | Ala | Glu | Lys | Pro | Tyr |
|  |  |  | 290 |  |  |  |  | 295 |  |  |  |  | 300 |  |
| Ala | Arg | Arg | Pro | Tyr | Pro | Pro | Phe | Met | Thr | Ser | Thr | Leu | Gln | Gln | Glu |
| 305 |  |  |  |  | 310 |  |  |  |  | 315 |  |  |  |  | 320 |
| Ala | Ser | Arg | Lys | Leu | Arg | Phe | Ser | Ala | Glu | Arg | Thr | Met | Ser | Ile | Ala |
|  |  |  |  | 325 |  |  |  |  | 330 |  |  |  |  | 335 |  |
| Gln | Arg | Leu | Tyr | Glu | Asn | Gly | Tyr | Ile | Thr | Tyr | Met | Arg | Thr | Asp | Ser |
|  |  |  | 340 |  |  |  |  | 345 |  |  |  |  | 350 |  |
| Thr | Thr | Leu | Ser | Glu | Ser | Ala | Ile | Asn | Ala | Ala | Arg | Thr | Gln | Ala | Arg |
|  |  |  | 355 |  |  |  |  | 360 |  |  |  |  | 365 |  |
| Gln | Leu | Tyr | Gly | Asp | Gly | Val | Arg | Arg | Pro | Ala | Pro | Arg | Gln | Tyr | Thr |
|  |  |  | 370 |  |  |  |  | 375 |  |  |  |  | 380 |  |
| Arg | Lys | Val | Lys | Asn | Ala | Gln | Glu | Ala | His | Glu | Ala | Ile | Arg | Pro | Ala |
| 385 |  |  |  |  | 390 |  |  |  |  | 395 |  |  |  |  | 400 |
| Gly | Glu | Thr | Phe | Ala | Thr | Pro | Asp | Ala | Val | Arg | Arg | Glu | Leu | Asp | Gly |
|  |  |  |  | 405 |  |  |  |  | 410 |  |  |  |  | 415 |  |
| Pro | Asn | Ile | Asp | Asp | Phe | Arg | Leu | Tyr | Glu | Leu | Ile | Trp | Gln | Arg | Thr |
|  |  |  | 420 |  |  |  |  | 425 |  |  |  |  | 430 |  |
| Val | Ala | Ser | Gln | Met | Ala | Asp | Ala | Arg | Gly | Met | Thr | Leu | Ser | Leu | Arg |
|  |  |  | 435 |  |  |  |  | 440 |  |  |  |  | 445 |  |
| Ile | Thr | Gly | Met | Ser | Gly | His | Gln | Glu | Val | Val | Phe | Ser | Ala | Thr | Gly |
| 450 |  |  |  |  | 455 |  |  |  |  | 460 |  |  |  |  |  |
| Arg | Thr | Leu | Thr | Phe | Pro | Gly | Phe | Leu | Lys | Ala | Tyr | Val | Glu | Thr | Val |
| 465 |  |  |  |  | 470 |  |  |  |  | 475 |  |  |  |  | 480 |
| Asp | Glu | Leu | Val | Gly | Gly | Glu | Ala | Asp | Ala | Glu | Arg | Arg | Leu | Pro |
|  |  |  |  | 485 |  |  |  |  | 490 |  |  |  |  | 495 |  |
| His | Leu | Thr | Pro | Gly | Gln | Arg | Leu | Asp | Ile | Val | Glu | Leu | Thr | Pro | Asp |
|  |  |  | 500 |  |  |  |  | 505 |  |  |  |  | 510 |  |
| Gly | His | Ala | Thr | Asn | Pro | Pro | Ala | Arg | Tyr | Thr | Glu | Ala | Ser | Leu | Val |
|  |  |  | 515 |  |  |  |  | 520 |  |  |  |  | 525 |  |
| Lys | Ala | Leu | Glu | Glu | Leu | Gly | Ile | Gly | Arg | Pro | Ser | Thr | Tyr | Ser | Ser |
| 530 |  |  |  |  | 535 |  |  |  |  | 540 |  |  |  |  |  |
| Ile | Ile | Lys | Thr | Ile | Gln | Asp | Arg | Gly | Tyr | Val | His | Lys | Lys | Gly | Ser |
| 545 |  |  |  |  | 550 |  |  |  |  | 555 |  |  |  |  | 560 |
| Ala | Leu | Val | Pro | Ser | Trp | Val | Ala | Phe | Ala | Val | Thr | Gly | Leu | Leu | Glu |
|  |  |  |  | 565 |  |  |  |  | 570 |  |  |  |  | 575 |  |
| Gln | His | Phe | Gly | Arg | Leu | Val | Asp | Tyr | Asp | Phe | Thr | Ala | Ala | Met | Glu |
|  |  |  | 580 |  |  |  |  | 585 |  |  |  |  | 590 |  |

```
Asp Glu Leu Asp Glu Ile Ala Ala Gly Asn Glu Arg Arg Thr Asn Trp
        595                 600                 605

Leu Asn Asn Phe Tyr Phe Gly Gly Asp His Gly Val Pro Asp Ser Val
610                 615                 620

Ala Arg Ser Gly Gly Leu Lys Lys Leu Val Gly Ile Asn Leu Glu Gly
625                 630                 635                 640

Ile Asp Ala Arg Glu Val Asn Ser Ile Lys Leu Phe Asp Asp Thr His
                645                 650                 655

Gly Arg Pro Ile Tyr Val Arg Val Gly Lys Asn Gly Pro Tyr Leu Glu
                660                 665                 670

Arg Leu Val Ala Gly Asp Thr Gly Glu Pro Thr Pro Gln Arg Ala Asn
            675                 680                 685

Leu Ser Asp Ser Ile Thr Pro Asp Glu Leu Thr Leu Gln Val Ala Glu
        690                 695                 700

Glu Leu Phe Ala Thr Pro Gln Gln Gly Arg Thr Leu Gly Leu Asp Pro
705                 710                 715                 720

Glu Thr Gly His Glu Ile Val Ala Arg Glu Gly Arg Phe Gly Pro Tyr
                725                 730                 735

Val Thr Glu Ile Leu Pro Glu Pro Ala Asp Ala Ala Ala Ala
            740                 745                 750

Gln Gly Val Lys Lys Arg Gln Lys Ala Ala Gly Pro Lys Pro Arg Thr
            755                 760                 765

Gly Ser Leu Leu Arg Ser Met Asp Leu Gln Thr Val Thr Leu Glu Asp
770                 775                 780

Ala Leu Arg Leu Leu Ser Leu Pro Arg Val Val Gly Val Asp Pro Ala
785                 790                 795                 800

Ser Val Glu Glu Ile Thr Ala Gln Asn Gly Arg Tyr Gly Pro Tyr Leu
                805                 810                 815

Lys Arg Gly Asn Asp Ser Arg Ser Leu Val Thr Glu Asp Gln Ile Phe
                820                 825                 830

Thr Ile Thr Leu Asp Glu Ala Leu Lys Ile Tyr Ala Glu Pro Lys Arg
        835                 840                 845

Arg Gly Arg Gln Ser Ala Ser Ala Pro Ala Cys Ala Ser Trp Glu Gln
    850                 855                 860

Ile Arg Arg Arg Ala Ser Gln Trp Ser Ser Arg Thr Ala Asp Ser Gly
865                 870                 875                 880

Arg Thr Ser Pro Thr Val Arg Pro Met Pro Ala Cys Val Arg Ala Thr
                885                 890                 895

Thr Trp Leu Pro
            900
```

(2) INFORMATION FOR SEQ ID NO:5:

(i) SEQUENCE CHARACTERISTICS:
  (A) LENGTH: 1391 base pairs
  (B) TYPE: nucleic acid
  (C) STRANDEDNESS: double
  (D) TOPOLOGY: both (ii) MOLECULE TYPE: cDNA (ix) FEATURE:
  (A) NAME/KEY: CDS
  (B) LOCATION: 289..1254

(xi) SEQUENCE DESCRIPTION: SEQ ID NO:5:

```
AAGACTTCCC GCAAACCGAC CATGAGTTCC GCGGCGTCGT CGGCTACTGG CCAGGCGTCG    60

CGTAACTGTA TGCGCGGTGA TCGCTGTTTG TAATGAGTTC AGCGACACGA AGAATAAAAT   120
```

-continued

```
ATGGTAGCCG AAATCACTAA GCTACAGTGC TGGTGCACGC CATGAAAGAC CGTCAATGAC      180

AAGGAGGACG GCCGAAATGC CCAAGGACCG ACTGCCGGAC TTGACGCCCA CAGGAGCGTA      240

CGCACCGGCC AACAGCGGCA TGACCATGGC AAGGCAGGAC GGCCCTCG ATG ACC GGC       297
                                                    Met Thr Gly
                                                     1

AAG CTC GTT GAG CGG GTG CAC GCA ATC AAT TGG AAC CGG TTG CTC GAT        345
Lys Leu Val Glu Arg Val His Ala Ile Asn Trp Asn Arg Leu Leu Asp
      5               10                  15

GCT AAA GAT TTG CAG GTC TGG GAA CGT TTG ACC GGT AAC TTT TGG TTG        393
Ala Lys Asp Leu Gln Val Trp Glu Arg Leu Thr Gly Asn Phe Trp Leu
 20              25                  30                      35

CCG GAA AAG ATT CCG CTC TCC AAC GAC CTG GCA TCT TGG CAA ACG TTG        441
Pro Glu Lys Ile Pro Leu Ser Asn Asp Leu Ala Ser Trp Gln Thr Leu
                 40                  45                  50

AGT TCC ACC GAG CAG CAG ACG ACG ATC CGG GTG TTC ACC GGC TTG ACC        489
Ser Ser Thr Glu Gln Gln Thr Thr Ile Arg Val Phe Thr Gly Leu Thr
             55                  60                  65

CTG CTC GAC ACC GCG CAG GCG ACG GTG GGA GCA GTG GCC ATG ATC GAC        537
Leu Leu Asp Thr Ala Gln Ala Thr Val Gly Ala Val Ala Met Ile Asp
         70                  75                  80

GAC GCG GTC ACC CCC CAC GAA GAG GCG GTC CTG ACC AAC ATG GCG TTC        585
Asp Ala Val Thr Pro His Glu Glu Ala Val Leu Thr Asn Met Ala Phe
     85                  90                  95

ATG GAG TCA GTG CAC GCC AAG AGC TAC AGC TCG ATC TTC TCG ACC CTG        633
Met Glu Ser Val His Ala Lys Ser Tyr Ser Ser Ile Phe Ser Thr Leu
100             105                 110                     115

TGC TCG ACC AAG CAG ATC GAC GAT GCC TTC GAC TGG TCG GAA CAG AAC        681
Cys Ser Thr Lys Gln Ile Asp Asp Ala Phe Asp Trp Ser Glu Gln Asn
                 120                 125                 130

CCT TAC CTG CAG CGA AAA GCG CAG ATC ATC GTC GAC TAC TAC CGC GGT        729
Pro Tyr Leu Gln Arg Lys Ala Gln Ile Ile Val Asp Tyr Tyr Arg Gly
             135                 140                 145

GAC GAC GCT CAA GCG CAA AGA TCG TCG GTA ATG CTG GAG TCC TTC CTG        777
Asp Asp Ala Gln Ala Gln Arg Ser Ser Val Met Leu Glu Ser Phe Leu
         150                 155                 160

TTC TAC TCC GGC TTC TAC CTG CCC ATG TAC TGG TCG TCG CGG GGT AAG        825
Phe Tyr Ser Gly Phe Tyr Leu Pro Met Tyr Trp Ser Ser Arg Gly Lys
     165                 170                 175

CTC ACC AAC ACC GCC GAT CTG ATC CGG CTG ATC ATC CGA GAT GAA GCC        873
Leu Thr Asn Thr Ala Asp Leu Ile Arg Leu Ile Ile Arg Asp Glu Ala
180                 185                 190                 195

GTC CAC GGC TAC TAC ATC GGC TAC AAA TGT CAA CGA GGT TTG GCC GAC        921
Val His Gly Tyr Tyr Ile Gly Tyr Lys Cys Gln Arg Gly Leu Ala Asp
                 200                 205                 210

CTG ACC GAC GCC GAG CGG GCC GAC CAC CGC GAA TAC ACC TGC GAG CTG        969
Leu Thr Asp Ala Glu Arg Ala Asp His Arg Glu Tyr Thr Cys Glu Leu
             215                 220                 225

CTG CAC ACG CTC TAC GCG AAC GAG ATC GAC TAT GCG CAC GAC TTG TAC       1017
Leu His Thr Leu Tyr Ala Asn Glu Ile Asp Tyr Ala His Asp Leu Tyr
         230                 235                 240

GAC GAG TTG GGC TGG ACC GAC GAC GTT TTG CCC TAC ATG CGT TAC AAC       1065
Asp Glu Leu Gly Trp Thr Asp Asp Val Leu Pro Tyr Met Arg Tyr Asn
     245                 250                 255

GCC AAC AAG GCG CTA GCC AAC CTG GGA TAC CAG CCT GCA TTC GAT CGT       1113
Ala Asn Lys Ala Leu Ala Asn Leu Gly Tyr Gln Pro Ala Phe Asp Arg
260                 265                 270                 275

GAC ACC TGC CAG GTG AAC CCG GCC GTG CGC GCA GCT CTC GAC CCC GGT       1161
Asp Thr Cys Gln Val Asn Pro Ala Val Arg Ala Ala Leu Asp Pro Gly
                 280                 285                 290
```

```
GCA  GGG  GAG  AAC  CAC  GAC  TTT  TTC  TCC  GGC  TCC  GGA  AGC  TCA  TAC  GTA    1209
Ala  Gly  Glu  Asn  His  Asp  Phe  Phe  Ser  Gly  Ser  Gly  Ser  Ser  Tyr  Val
               295                          300                 305

ATG  GGC  ACC  CAC  CAA  CCC  ACC  ACC  GAC  ACC  GAC  TGG  GAC  TTC  TAA         1254
Met  Gly  Thr  His  Gln  Pro  Thr  Thr  Asp  Thr  Asp  Trp  Asp  Phe  *
               310                          315                 320

CCGCCCAGCG  CGTCGGGGGC  GTCGAGCACC  ACGCGACACC  GGGCCCGATC  GATCTGCTAG           1314

CTTGAGTCTG  GTCAGGCATC  GTCGTCAGCA  GCCATGCCCT  ATGTTTGTCG  TCGACTCAGA           1374

TATGCGGCAA  TCCAATC                                                              1391
```

( 2 ) INFORMATION FOR SEQ ID NO:6:

( i ) SEQUENCE CHARACTERISTICS:
        ( A ) LENGTH: 321 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Thr  Gly  Lys  Leu  Val  Glu  Arg  Val  His  Ala  Ile  Asn  Trp  Asn  Arg
 1              5                        10                       15

Leu  Leu  Asp  Ala  Lys  Asp  Leu  Gln  Val  Trp  Glu  Arg  Leu  Thr  Gly  Asn
               20                        25                       30

Phe  Trp  Leu  Pro  Glu  Lys  Ile  Pro  Leu  Ser  Asn  Asp  Leu  Ala  Ser  Trp
               35                        40                       45

Gln  Thr  Leu  Ser  Ser  Thr  Glu  Gln  Thr  Thr  Ile  Arg  Val  Phe  Thr
          50                        55                       60

Gly  Leu  Thr  Leu  Leu  Asp  Thr  Ala  Gln  Ala  Thr  Val  Gly  Ala  Val  Ala
 65                      70                       75                        80

Met  Ile  Asp  Asp  Ala  Val  Thr  Pro  His  Glu  Glu  Ala  Val  Leu  Thr  Asn
                    85                       90                       95

Met  Ala  Phe  Met  Glu  Ser  Val  His  Ala  Lys  Ser  Tyr  Ser  Ser  Ile  Phe
               100                      105                      110

Ser  Thr  Leu  Cys  Ser  Thr  Lys  Gln  Ile  Asp  Asp  Ala  Phe  Asp  Trp  Ser
          115                      120                      125

Glu  Gln  Asn  Pro  Tyr  Leu  Gln  Arg  Lys  Ala  Gln  Ile  Ile  Val  Asp  Tyr
     130                      135                      140

Tyr  Arg  Gly  Asp  Asp  Ala  Gln  Ala  Gln  Arg  Ser  Ser  Val  Met  Leu  Glu
145                      150                      155                      160

Ser  Phe  Leu  Phe  Tyr  Ser  Gly  Phe  Tyr  Leu  Pro  Met  Tyr  Trp  Ser  Ser
                    165                      170                      175

Arg  Gly  Lys  Leu  Thr  Asn  Thr  Ala  Asp  Leu  Ile  Arg  Leu  Ile  Ile  Arg
               180                      185                      190

Asp  Glu  Ala  Val  His  Gly  Tyr  Tyr  Ile  Gly  Tyr  Lys  Cys  Gln  Arg  Gly
          195                      200                      205

Leu  Ala  Asp  Leu  Thr  Asp  Ala  Glu  Arg  Ala  Asp  His  Arg  Glu  Tyr  Thr
     210                      215                      220

Cys  Glu  Leu  Leu  His  Thr  Leu  Tyr  Ala  Asn  Glu  Ile  Asp  Tyr  Ala  His
225                      230                      235                      240

Asp  Leu  Tyr  Asp  Glu  Leu  Gly  Trp  Thr  Asp  Asp  Val  Leu  Pro  Tyr  Met
                    245                      250                      255

Arg  Tyr  Asn  Ala  Asn  Lys  Ala  Leu  Ala  Asn  Leu  Gly  Tyr  Gln  Pro  Ala
               260                      265                      270

Phe  Asp  Arg  Asp  Thr  Cys  Gln  Val  Asn  Pro  Ala  Val  Arg  Ala  Ala  Leu
          275                      280                      285
```

```
Asp  Pro  Gly  Ala  Gly  Glu  Asn  His  Asp  Phe  Phe  Ser  Gly  Ser  Gly  Ser
     290                      295                     300

Ser  Tyr  Val  Met  Gly  Thr  His  Gln  Pro  Thr  Thr  Asp  Thr  Asp  Trp  Asp
305                      310                     315                         320

Phe
```

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: linear ( i i ) MOLECULE TYPE: peptide ( i x ) FEATURE:
        ( A ) NAME/KEY: Modified-site
        ( B ) LOCATION: Thr(1)
        ( D ) OTHER INFORMATION: /product="OTHER"
                / note= "TERMINAL IS ACETYLATED"

( x i ) SEQUENCE DESCRIPTION: SEQ ID NO:7:

```
Thr  Asp  Thr  Asp  Trp  Asp  Phe
1                    5
```

( 2 ) INFORMATION FOR SEQ ID NO:8:

( i ) SEQUENCE CHARACTERISTICS:
        ( A ) LENGTH: 7 amino acids
        ( B ) TYPE: amino acid
        ( C ) STRANDEDNESS: Not Relevant
        ( D ) TOPOLOGY: linear ( i i ) MOLECULE TYPE: peptide ( i x ) FEATURE:
        ( A ) NAME/KEY: Modified-site
        ( B ) LOCATION: Thr(1)
        ( D ) OTHER INFORMATION: /product="OTHER"
                / note= "TERMINAL IS ACETYLATED"

( x i ) SEQUENCE DESCRIPTION: SEQ ID NO:8:

```
Glu  Asp  Asp  Asp  Trp  Asp  Phe
1                    5
```

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:9:

TTCATGGAGG CSGTSCA                                                17

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:10:

TAGAACAGGA ASGACTC                                                                                        17

( 2 ) INFORMATION FOR SEQ ID NO:11:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:11:

TGSACSGCCT CGTC                                                                                           14

( 2 ) INFORMATION FOR SEQ ID NO:12:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:12:

TCTAGAATGA CCGGCAAGCT CGTTG                                                                               25

( 2 ) INFORMATION FOR SEQ ID NO:13:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

TCTAGATTAG AAGTCCCAGT CGGTG                                                                               25

( 2 ) INFORMATION FOR SEQ ID NO:14:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

ATCGAGAACA TCCA                                                                                           14

( 2 ) INFORMATION FOR SEQ ID NO:15:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

AAGAAGATGC CCTC                                                                                           14

( 2 ) INFORMATION FOR SEQ ID NO:16:

( i ) SEQUENCE CHARACTERISTICS:
  ( A ) LENGTH: 31 base pairs
  ( B ) TYPE: nucleic acid
  ( C ) STRANDEDNESS: single
  ( D ) TOPOLOGY: linear ( i i ) MOLECULE TYPE: DNA ( x i ) SEQUENCE DESCRIPTION: SEQ ID NO:16:

GCTAGCATGG AGCGTGGGGC GCAGTTGGCT G        31

( 2 ) INFORMATION FOR SEQ ID NO:17:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:17:

GCTAGCTTAT GGAAGCCACG TCGTCGCCCT        30

( 2 ) INFORMATION FOR SEQ ID NO:18:

( i ) SEQUENCE CHARACTERISTICS:
    ( A ) LENGTH: 41 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:18:

AAAAAGCTA GCCCCACCGT GATCGCCGAG CCCGTAGCCT C        41

( 2 ) INFORMATION FOR SEQ ID NO:19:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:19:

AAAAAGCTA GCCTACAGCA TGCAGGA        27

( 2 ) INFORMATION FOR SEQ ID NO:20:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:20:

GARTTCTTCC ARAC        14

( 2 ) INFORMATION FOR SEQ ID NO:21:

( i ) SEQUENCE CHARACTERISTICS:
    ( A ) LENGTH: 17 base pairs
    ( B ) TYPE: nucleic acid
    ( C ) STRANDEDNESS: single (D) TOPOLOGY: linear (ii) MOLECULE TYPE: DNA (xi) SEQUENCE DESCRIPTION: SEQ ID NO:21:

GCGTAGGTGT CGATGAT 17

(2) INFORMATION FOR SEQ ID NO:22:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:22:

CCCACCGTSA TCGCCGAGCC SGT 23

(2) INFORMATION FOR SEQ ID NO:23:

(i) SEQUENCE CHARACTERISTICS:
(A) LENGTH: 17 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:23:

AGGGTCTGGA AGAACTC 17

(2) INFORMATION FOR SEQ ID NO:24:

(i) SEQUENCE CHARACTERISTICS:
(A) LENGTH: 4107 base pairs
(B) TYPE: nucleic acid
(C) STRANDEDNESS: double
(D) TOPOLOGY: both (ii) MOLECULE TYPE: cDNA (ix) FEATURE:
(A) NAME/KEY: CDS
(B) LOCATION: 446..2620

(xi) SEQUENCE DESCRIPTION: SEQ ID NO:24:

```
TAGATAAGGA  AGATTGCGGT  GCCATGGATT  ACTCGCGGGC  GCAGCCTGGT  CTATTTCTCC        60
AGCGTGTCGG  AGAACACCCA  CCGCTTTGTG  CAGAAACTGG  GTATTCCCGC  CACGCGGATA       120
CCGCTGCATG  GCCGGATCGA  GGTCGACGAG  CCGTACGTGC  TGATACTGCC  CACCTACGGT       180
GGCGGCCGGG  CCAACCCGGG  TCTCGATGCC  GGCGGATACG  TCCCCAAACA  GGTCATTGCC       240
TTCTTGAACA  ACGACCACAA  TCGACGCACG  TGCGCGGGGT  CATCGCTGCC  GGCAATACCA       300
ACTTCGGTGC  CGAGTTCTCG  TACGCCGGCG  ACGTCGTCTC  CCGAAAATGT  AGCGTTCCCT       360
ACCTATACCG  CTTCGAACTG  ATGGGCACCG  AGGACGACGT  CGCCGCCGTC  CGCACCGGTC       420
TCGCTGAATT  CTGGAAGGAA  CAGAC GTG CCA CCA ACC GTC ATT GCA GAG CCC            472
                             Val Pro Pro Thr Val Ile Ala Glu Pro
                              1               5

GTA GCC TCC GGC GCG CAC GCC TCT TAC TCT GGG GGG CCG GGC GAA ACG             520
Val Ala Ser Gly Ala His Ala Ser Tyr Ser Gly Gly Pro Gly Glu Thr
 10              15                  20                  25

GAC TAT CAC GCG CTG AAC GCG ATG CTG AAC CTG TAC GAC GCG GAC GGC             568
Asp Tyr His Ala Leu Asn Ala Met Leu Asn Leu Tyr Asp Ala Asp Gly
            30                  35                  40
```

| | | | | | | | | | | | | | | | | |
|---|---|---|---|---|---|---|---|---|---|---|---|---|---|---|---|---|
| AAG | ATC | CAG | TTC | GAC | AAG | GAT | CGG | GAA | GCA | GCC | CAC | CAG | TAC | TTT | TTG | 616 |
| Lys | Ile | Gln | Phe | Asp | Lys | Asp | Arg | Glu | Ala | Ala | His | Gln | Tyr | Phe | Leu | |
| | | | 45 | | | | | 50 | | | | | 55 | | | |
| CAG | CAT | GTC | AAT | CAG | AAC | ACG | GTC | TTC | TTC | CAT | AAT | CAG | GAC | GAG | AAG | 664 |
| Gln | His | Val | Asn | Gln | Asn | Thr | Val | Phe | Phe | His | Asn | Gln | Asp | Glu | Lys | |
| | | 60 | | | | 65 | | | | | 70 | | | | | |
| CTC | GAC | TAC | CTG | ATC | CGC | GAG | AAT | TAC | TAC | GAG | CGT | GAG | GTT | CTC | GAC | 712 |
| Leu | Asp | Tyr | Leu | Ile | Arg | Glu | Asn | Tyr | Tyr | Glu | Arg | Glu | Val | Leu | Asp | |
| | 75 | | | | | 80 | | | | 85 | | | | | | |
| CAG | TAC | TCG | CGC | AAC | TTC | GTC | AAG | ACG | CTG | CTA | GAC | CGC | GCC | TAC | GCC | 760 |
| Gln | Tyr | Ser | Arg | Asn | Phe | Val | Lys | Thr | Leu | Leu | Asp | Arg | Ala | Tyr | Ala | |
| 90 | | | | | 95 | | | | 100 | | | | | 105 | | |
| AAA | AAG | TTC | CGG | TTT | CCG | ACG | TTT | TTG | GGT | GCG | TTC | AAG | TAC | TAC | ACC | 808 |
| Lys | Lys | Phe | Arg | Phe | Pro | Thr | Phe | Leu | Gly | Ala | Phe | Lys | Tyr | Tyr | Thr | |
| | | | | 110 | | | | | 115 | | | | | 120 | | |
| TCC | TAC | ACG | CTG | AAA | ACC | TTT | GAC | GGG | AAG | CGC | TAT | CTG | GAG | CGC | TTC | 856 |
| Ser | Tyr | Thr | Leu | Lys | Thr | Phe | Asp | Gly | Lys | Arg | Tyr | Leu | Glu | Arg | Phe | |
| | | | | 125 | | | | | 130 | | | | | 135 | | |
| GAG | GAC | CGC | GTG | GTC | ATG | GTG | GCG | CTA | ACG | TTG | GCC | GCC | GGC | GAT | ACC | 904 |
| Glu | Asp | Arg | Val | Val | Met | Val | Ala | Leu | Thr | Leu | Ala | Ala | Gly | Asp | Thr | |
| | | 140 | | | | 145 | | | | | 150 | | | | | |
| GCA | CTT | GCC | GAG | CTG | CTG | GTC | GAC | GAG | ATC | ATC | GAC | GGC | CGC | TTC | CAG | 952 |
| Ala | Leu | Ala | Glu | Leu | Leu | Val | Asp | Glu | Ile | Ile | Asp | Gly | Arg | Phe | Gln | |
| | 155 | | | | | 160 | | | | 165 | | | | | | |
| CCC | GCC | ACA | CCG | ACG | TTT | TTG | AAT | TCT | GGC | AAG | AAG | CAG | CGC | GGG | GAG | 1000 |
| Pro | Ala | Thr | Pro | Thr | Phe | Leu | Asn | Ser | Gly | Lys | Lys | Gln | Arg | Gly | Glu | |
| 170 | | | | | 175 | | | | 180 | | | | | 185 | | |
| CCC | GTG | AGC | TGT | TTT | TTG | CTT | CGC | GTC | GAA | GAT | AAC | ATG | GAG | TCG | ATC | 1048 |
| Pro | Val | Ser | Cys | Phe | Leu | Leu | Arg | Val | Glu | Asp | Asn | Met | Glu | Ser | Ile | |
| | | | | 190 | | | | | 195 | | | | | 200 | | |
| GGA | CGG | TCG | ATC | AAC | TCC | GCG | CTG | CAG | CTA | TCC | AAG | CGT | GGC | GGG | GGA | 1096 |
| Gly | Arg | Ser | Ile | Asn | Ser | Ala | Leu | Gln | Leu | Ser | Lys | Arg | Gly | Gly | Gly | |
| | | | | 205 | | | | | 210 | | | | | 215 | | |
| GTG | GCG | TTG | CTG | CTG | ACC | AAC | ATT | CGC | GAG | CAC | GGC | GGC | GCC | ATC | AAG | 1144 |
| Val | Ala | Leu | Leu | Leu | Thr | Asn | Ile | Arg | Glu | His | Gly | Gly | Ala | Ile | Lys | |
| | | | 220 | | | | | 225 | | | | | 230 | | | |
| AAC | ATC | GAG | AAC | CAG | TCC | TCG | GGC | GTC | ATC | CCC | ATC | ATG | AAG | TTG | CTG | 1192 |
| Asn | Ile | Glu | Asn | Gln | Ser | Ser | Gly | Val | Ile | Pro | Ile | Met | Lys | Leu | Leu | |
| | 235 | | | | | 240 | | | | 245 | | | | | | |
| GAG | GAT | GCG | TTC | TCC | TAC | GCC | AAC | CAG | CTG | GGC | GCT | CGT | CAA | GGT | GCC | 1240 |
| Glu | Asp | Ala | Phe | Ser | Tyr | Ala | Asn | Gln | Leu | Gly | Ala | Arg | Gln | Gly | Ala | |
| 250 | | | | | 255 | | | | | 260 | | | | | 265 | |
| GGC | GCG | GTG | TAC | CTG | CAC | GCC | CAT | CAC | CCC | GAC | ATC | TAC | CGA | TTC | CTG | 1288 |
| Gly | Ala | Val | Tyr | Leu | His | Ala | His | His | Pro | Asp | Ile | Tyr | Arg | Phe | Leu | |
| | | | | 270 | | | | | 275 | | | | | 280 | | |
| GAC | ACC | AAG | CGT | GAG | AAC | GCC | GAC | GAG | AAG | ATC | CGG | ATC | AAG | ACG | CTG | 1336 |
| Asp | Thr | Lys | Arg | Glu | Asn | Ala | Asp | Glu | Lys | Ile | Arg | Ile | Lys | Thr | Leu | |
| | | | 285 | | | | | 290 | | | | | 295 | | | |
| AGT | CTG | GGG | GTG | GTG | ATC | CCC | GAC | ATC | ACC | TTC | GAG | TTG | GCC | AAG | CGC | 1384 |
| Ser | Leu | Gly | Val | Val | Ile | Pro | Asp | Ile | Thr | Phe | Glu | Leu | Ala | Lys | Arg | |
| | | 300 | | | | 305 | | | | | 310 | | | | | |
| AAC | GAT | GAC | ATG | TAC | CTG | TTC | TCG | CCC | TAC | GAT | GTC | GAG | CGG | GTC | TAC | 1432 |
| Asn | Asp | Asp | Met | Tyr | Leu | Phe | Ser | Pro | Tyr | Asp | Val | Glu | Arg | Val | Tyr | |
| | 315 | | | | | 320 | | | | 325 | | | | | | |
| GGT | GTG | CCG | TTC | GCT | GAC | ATC | TCG | GTC | ACC | GAG | AAG | TAC | TAC | GAA | ATG | 1480 |
| Gly | Val | Pro | Phe | Ala | Asp | Ile | Ser | Val | Thr | Glu | Lys | Tyr | Tyr | Glu | Met | |
| 330 | | | | 335 | | | | | 340 | | | | | | 345 | |
| GTC | GAT | GAC | GCG | CGC | ATC | CGC | AAG | ACC | AAG | ATC | AAG | GCA | CGG | GAG | TTC | 1528 |
| Val | Asp | Asp | Ala | Arg | Ile | Arg | Lys | Thr | Lys | Ile | Lys | Ala | Arg | Glu | Phe | |
| | | | | 350 | | | | | 355 | | | | | 360 | | |

```
TTC CAG ACG CTG GCC GAG CTG CAG TTC GAG TCC GGC TAC CCC TAT ATC    1576
Phe Gln Thr Leu Ala Glu Leu Gln Phe Glu Ser Gly Tyr Pro Tyr Ile
        365                     370                 375

ATG TTC GAA GAC ACC GTC AAT CGC GCT AAT CCA ATT GAT GGC AAG ATC    1624
Met Phe Glu Asp Thr Val Asn Arg Ala Asn Pro Ile Asp Gly Lys Ile
        380                     385                 390

ACG CAC AGC AAC CTG TGC TCG GAG ATC CTG CAA GTG TCT ACG CCG TCA    1672
Thr His Ser Asn Leu Cys Ser Glu Ile Leu Gln Val Ser Thr Pro Ser
        395                     400                 405

TTG TTC AAC GAG GAC TTG TCG TAT GCC AAA GTG GGC AAA GAC ATT TCG    1720
Leu Phe Asn Glu Asp Leu Ser Tyr Ala Lys Val Gly Lys Asp Ile Ser
410                     415                     420          425

TGC AAC CTG GGG TCG CTG AAC ATC GCC AAG ACG ATG GAC TCG CCG GAC    1768
Cys Asn Leu Gly Ser Leu Asn Ile Ala Lys Thr Met Asp Ser Pro Asp
                430                     435                 440

TTC GCG CAG ACG ATC GAG GTG GCG ATC CGC GCG TTG ACC GCG GTG AGG    1816
Phe Ala Gln Thr Ile Glu Val Ala Ile Arg Ala Leu Thr Ala Val Arg
            445                     450                 455

CAC CAA ACC CAT ATC AAG TCG GTG CCC TCA ATC GAG CAG GGC AAC AAC    1864
His Gln Thr His Ile Lys Ser Val Pro Ser Ile Glu Gln Gly Asn Asn
        460                     465                 470

GAC TCC CAC GCG ATC GGG CTA GGA CAG ATG AAC CTG CAC GGC TAC CTG    1912
Asp Ser His Ala Ile Gly Leu Gly Gln Met Asn Leu His Gly Tyr Leu
        475                     480                 485

GCC CGG GAA CGC ATC TTC TAC GGA TCC GAC GAA GGC ATC GAC TTC ACC    1960
Ala Arg Glu Arg Ile Phe Tyr Gly Ser Asp Glu Gly Ile Asp Phe Thr
490                     495                     500          505

AAC ATC TAC TTC TAT ACG GTG CTG TAT CAC GCG TTG CGG GCA TCC AAC    2008
Asn Ile Tyr Phe Tyr Thr Val Leu Tyr His Ala Leu Arg Ala Ser Asn
                510                     515                 520

CGC ATC GCG ATC GAA CGC GGC ACG CAC TTC AAG GGT TTC GAG CGG TCC    2056
Arg Ile Ala Ile Glu Arg Gly Thr His Phe Lys Gly Phe Glu Arg Ser
            525                     530                 535

AAG TAC GCG TCC GGG GAA TTC TTC GAC AAG TAC ACC GAC CAG ATT TGG    2104
Lys Tyr Ala Ser Gly Glu Phe Phe Asp Lys Tyr Thr Asp Gln Ile Trp
        540                     545                 550

GAG CCG AAG ACC CAG AAG GTA CGC CAG CTG TTC GCC GAC GCC GGC ATC    2152
Glu Pro Lys Thr Gln Lys Val Arg Gln Leu Phe Ala Asp Ala Gly Ile
        555                     560                 565

CGC ATC CCA ACG CAG GAC GAC TGG CGT CGG CTC AAG GAG TCG GTG CAA    2200
Arg Ile Pro Thr Gln Asp Asp Trp Arg Arg Leu Lys Glu Ser Val Gln
570                     575                     580          585

GCG CAC GGC ATC TAC AAC CAG AAC CTG CAG GCG GTG CCG CCG ACC GGG    2248
Ala His Gly Ile Tyr Asn Gln Asn Leu Gln Ala Val Pro Pro Thr Gly
                590                     595                 600

TCG ATT TCC TAC ATC AAC CAT TCG ACG TCG TCG ATT CAC CCG ATC GTG    2296
Ser Ile Ser Tyr Ile Asn His Ser Thr Ser Ser Ile His Pro Ile Val
            605                     610                 615

TCG AAG GTC GAG GTC CGC AAG GAA GGC AAG ATC GGG CGG GTC TAC TAC    2344
Ser Lys Val Glu Val Arg Lys Glu Gly Lys Ile Gly Arg Val Tyr Tyr
        620                     625                 630

CCG GCG CCG TAT ATG ACC AAC GAC AAC CTG GAG TAC TAC GAA GAC GCC    2392
Pro Ala Pro Tyr Met Thr Asn Asp Asn Leu Glu Tyr Tyr Glu Asp Ala
        635                     640                 645

TAC GAG ATC GGT TAC GAG AAG ATC ATC GAC ACC TAC GCG GCG GCC ACC    2440
Tyr Glu Ile Gly Tyr Glu Lys Ile Ile Asp Thr Tyr Ala Ala Ala Thr
650                     655                     660          665

CAG CAT GTG GAT CAA GGG CTT TCG CTG ACG TTG TTC TTC AAA GAC ACC    2488
Gln His Val Asp Gln Gly Leu Ser Leu Thr Leu Phe Phe Lys Asp Thr
                670                     675                 680
```

```
GCC ACC ACC CGC GAC GTG AAC AAG GCG CAG ATT TAC GCC TGG CGC AAG        2536
Ala Thr Thr Arg Asp Val Asn Lys Ala Gln Ile Tyr Ala Trp Arg Lys
            685                 690                 695

GGG ATC AAG ACG CTG TAC TAC ATC CGG CTG CGG CAG ATG GCG TTG GAG        2584
Gly Ile Lys Thr Leu Tyr Tyr Ile Arg Leu Arg Gln Met Ala Leu Glu
            700                 705                 710

GGC ACC GAG GTC GAG GGT TGC GTG TCC TGC ATG CTG TAGCACCGGC             2630
Gly Thr Glu Val Glu Gly Cys Val Ser Cys Met Leu
            715                 720                 725

GCGCCAGAGT GAAAGTGGCG ACGGCTTCGC GGCGTGGTCG CGTCGTGAAC CTCACATTCA      2690
ACCAAGCCTG GCGTGGCCAG TCTGCCCAGG TCAGCGCTTG CAACGCGGTA AGGTGCTTGA      2750
TGTGGTCAGA ATCCCCCGAC CCCACCCCAG TGCAAAGCCG GGGGTGAAAG TCGACGCCGC      2810
AGTGAACGGT GGCGTGACCG ACCGCAAGAA GGTGCGCAAC GAAATCGTCG ACGCGGCGTT      2870
CCGCTATCGA CCGGCTGGGC CCCGAGCTGA GTGTGCGCCA AATCGCCGAA GAGGCCGGCA      2930
CCGCCAAGCC CAAGATCTAT CGGCATTTCA CCGACAAGTC CGATTTGCTC GAGGCTATCG      2990
GGATGCGACT GCGTGACATG CTGTGGGCGG CGATCTTCCC GTCGCTCGAC TTAGCCACCG      3050
ACTCTGCCCG CGAAGTTATC CGGCGCACGT CGAGGAGTAC GTCAACCTCG TCGACCAGCA      3110
CCCCAACGTG CTGCGGGTGT TCATTCAGGG CCGCTCGCGA AAGCAGTCCG AGGCGACGGT      3170
ACGCACCCTC AACGAAGGCC GGGAGATCAC GCTGGCCATG GCGAGATGTT CAACAACGAG      3230
CTGCGCAGAT GGAGCTGAAT CGAGCCGCGC TCGAACCATT CGGATCGGCC GCATCGGCAA      3290
CCGAGTGGTG GTTGGGCCCC GAACCCGACA GCCCGCGCGC ATGCCGCGTG AGCAGTTCGT      3350
GGCGCATCTG ACCACCATCA TGATGGGCGT GATCGGTGCG CACCGCCGAA GCGCTGGGCA      3410
TCGCGGTCGA CCCTGACCAA CCGATCCACG ACGCGGTACC CAACAAGTGC GCCGACACGT      3470
GCGTTGAGCG CGGCGGCCGT TGACATCGCT GCGGCAATCA ACAACACTCG TCATATCCGA      3530
TACCCTGGGT ACTGGGTATT TGCGCCGGCG AGGGTGACTG AAGCGCCAAA CTCGCCGCTG      3590
AACAGGAACC GATCCATTGT GAGCATTGCC GATACGGCTG CCAAGCCGTC CACGCCAAGC      3650
CCGGCCAACC AGCCGCCGGT ACGTACCCGC GCCGTCATCA TCGGAACCGG ATTCTCCGGT      3710
TTGGGCATGG CCATCGCACT GCAAAAGCAA GGAGTGACTT CGTCATATTG GAGAACGACG      3770
ACGTCGGCGG CACCTGGCGC GACAACAGGT ACCCCGCTGC GCGCGACATC CCGTCGCACC      3830
TGTACTCCTT CTCGTTCGAG CCCAAGGCGG ACTGGAAACA CCTGTTTTCC TACTGGGACG      3890
AAATCTTGGG CTACCTCAAA GGGGTCACCG ACAAGTAGCC CTGCGCCGCT ACATCGAGTT      3950
CAATTCGCTC GTCGATCGCG GCTACTGGGA CGACGACGAA TGCCGCTGGC ACGTGTTCAC      4010
CGCCGACGGG ACGTGAATAC GTCGCGCAGT TCCTGATCTC CGGGGCCGGT GCGTTGCACA      4070
TCCCGTCCTT CCCCGAGATC GCAGGTCGCG ACGAATT                               4107
```

( 2 ) INFORMATION FOR SEQ ID NO:25:

( i ) SEQUENCE CHARACTERISTICS:
        ( A ) LENGTH: 725 amino acids
        ( B ) TYPE: amino acid
        ( D ) TOPOLOGY: linear ( i i ) MOLECULE TYPE: protein ( x i ) SEQUENCE DESCRIPTION: SEQ ID NO:25:

```
Val Pro Pro Thr Val Ile Ala Glu Pro Val Ala Ser Gly Ala His Ala
 1               5                  10                  15

Ser Tyr Ser Gly Gly Pro Gly Glu Thr Asp Tyr His Ala Leu Asn Ala
            20                  25                  30
```

-continued

```
Met  Leu  Asn  Leu  Tyr  Asp  Ala  Asp  Gly  Lys  Ile  Gln  Phe  Asp  Lys  Asp
               35                  40                       45
Arg  Glu  Ala  Ala  His  Gln  Tyr  Phe  Leu  Gln  His  Val  Asn  Gln  Asn  Thr
          50                       55                       60
Val  Phe  Phe  His  Asn  Gln  Asp  Glu  Lys  Leu  Asp  Tyr  Leu  Ile  Arg  Glu
 65                           70                  75                           80
Asn  Tyr  Tyr  Glu  Arg  Glu  Val  Leu  Asp  Gln  Tyr  Ser  Arg  Asn  Phe  Val
                    85                       90                            95
Lys  Thr  Leu  Leu  Asp  Arg  Ala  Tyr  Ala  Lys  Lys  Phe  Arg  Phe  Pro  Thr
               100                      105                      110
Phe  Leu  Gly  Ala  Phe  Lys  Tyr  Tyr  Thr  Ser  Tyr  Thr  Leu  Lys  Thr  Phe
               115                      120                      125
Asp  Gly  Lys  Arg  Tyr  Leu  Glu  Arg  Phe  Glu  Asp  Arg  Val  Val  Met  Val
     130                      135                      140
Ala  Leu  Thr  Leu  Ala  Ala  Gly  Asp  Thr  Ala  Leu  Ala  Glu  Leu  Leu  Val
145                           150                      155                      160
Asp  Glu  Ile  Ile  Asp  Gly  Arg  Phe  Gln  Pro  Ala  Thr  Pro  Thr  Phe  Leu
                    165                      170                      175
Asn  Ser  Gly  Lys  Lys  Gln  Arg  Gly  Glu  Pro  Val  Ser  Cys  Phe  Leu  Leu
               180                      185                      190
Arg  Val  Glu  Asp  Asn  Met  Glu  Ser  Ile  Gly  Arg  Ser  Ile  Asn  Ser  Ala
          195                      200                      205
Leu  Gln  Leu  Ser  Lys  Arg  Gly  Gly  Val  Ala  Leu  Leu  Leu  Thr  Asn
     210                      215                      220
Ile  Arg  Glu  His  Gly  Gly  Ala  Ile  Lys  Asn  Ile  Glu  Asn  Gln  Ser  Ser
225                           230                      235                      240
Gly  Val  Ile  Pro  Ile  Met  Lys  Leu  Leu  Glu  Asp  Ala  Phe  Ser  Tyr  Ala
                    245                      250                      255
Asn  Gln  Leu  Gly  Ala  Arg  Gln  Gly  Ala  Gly  Ala  Val  Tyr  Leu  His  Ala
               260                      265                      270
His  His  Pro  Asp  Ile  Tyr  Arg  Phe  Leu  Asp  Thr  Lys  Arg  Glu  Asn  Ala
          275                      280                      285
Asp  Glu  Lys  Ile  Arg  Ile  Lys  Thr  Leu  Ser  Leu  Gly  Val  Val  Ile  Pro
     290                      295                      300
Asp  Ile  Thr  Phe  Glu  Leu  Ala  Lys  Arg  Asn  Asp  Met  Tyr  Leu  Phe
305                           310                      315                      320
Ser  Pro  Tyr  Asp  Val  Glu  Arg  Val  Tyr  Gly  Val  Pro  Phe  Ala  Asp  Ile
                    325                      330                      335
Ser  Val  Thr  Glu  Lys  Tyr  Tyr  Glu  Met  Val  Asp  Asp  Ala  Arg  Ile  Arg
               340                      345                      350
Lys  Thr  Lys  Ile  Lys  Ala  Arg  Glu  Phe  Phe  Gln  Thr  Leu  Ala  Glu  Leu
          355                      360                      365
Gln  Phe  Glu  Ser  Gly  Tyr  Pro  Tyr  Ile  Met  Phe  Glu  Asp  Thr  Val  Asn
     370                      375                      380
Arg  Ala  Asn  Pro  Ile  Asp  Gly  Lys  Ile  Thr  His  Ser  Asn  Leu  Cys  Ser
385                           390                      395                      400
Glu  Ile  Leu  Gln  Val  Ser  Thr  Pro  Ser  Leu  Phe  Asn  Glu  Asp  Leu  Ser
                    405                      410                      415
Tyr  Ala  Lys  Val  Gly  Lys  Asp  Ile  Ser  Cys  Asn  Leu  Gly  Ser  Leu  Asn
               420                      425                      430
Ile  Ala  Lys  Thr  Met  Asp  Ser  Pro  Asp  Phe  Ala  Gln  Thr  Ile  Glu  Val
          435                      440                      445
Ala  Ile  Arg  Ala  Leu  Thr  Ala  Val  Arg  His  Gln  Thr  His  Ile  Lys  Ser
```

-continued

```
                450                              455                              460
Val  Pro  Ser  Ile  Glu  Gln  Gly  Asn  Asn  Asp  Ser  His  Ala  Ile  Gly  Leu
465                      470                     475                          480
Gly  Gln  Met  Asn  Leu  His  Gly  Tyr  Leu  Ala  Arg  Glu  Arg  Ile  Phe  Tyr
                    485                     490                          495
Gly  Ser  Asp  Glu  Gly  Ile  Asp  Phe  Thr  Asn  Ile  Tyr  Phe  Tyr  Thr  Val
               500                      505                         510
Leu  Tyr  His  Ala  Leu  Arg  Ala  Ser  Asn  Arg  Ile  Ala  Ile  Glu  Arg  Gly
          515                          520                    525
Thr  His  Phe  Lys  Gly  Phe  Glu  Arg  Ser  Lys  Tyr  Ala  Ser  Gly  Glu  Phe
     530                          535                    540
Phe  Asp  Lys  Tyr  Thr  Asp  Gln  Ile  Trp  Glu  Pro  Lys  Thr  Gln  Lys  Val
545                      550                     555                          560
Arg  Gln  Leu  Phe  Ala  Asp  Ala  Gly  Ile  Arg  Ile  Pro  Thr  Gln  Asp  Asp
               565                          570                         575
Trp  Arg  Arg  Leu  Lys  Glu  Ser  Val  Gln  Ala  His  Gly  Ile  Tyr  Asn  Gln
               580                     585                          590
Asn  Leu  Gln  Ala  Val  Pro  Pro  Thr  Gly  Ser  Ile  Ser  Tyr  Ile  Asn  His
          595                          600                    605
Ser  Thr  Ser  Ser  Ile  His  Pro  Ile  Val  Ser  Lys  Val  Glu  Val  Arg  Lys
     610                          615                    620
Glu  Gly  Lys  Ile  Gly  Arg  Val  Tyr  Tyr  Pro  Ala  Pro  Tyr  Met  Thr  Asn
625                      630                     635                          640
Asp  Asn  Leu  Glu  Tyr  Tyr  Glu  Asp  Ala  Tyr  Glu  Ile  Gly  Tyr  Glu  Lys
                    645                     650                          655
Ile  Ile  Asp  Thr  Tyr  Ala  Ala  Ala  Thr  Gln  His  Val  Asp  Gln  Gly  Leu
               660                          665                    670
Ser  Leu  Thr  Leu  Phe  Phe  Lys  Asp  Thr  Ala  Thr  Arg  Asp  Val  Asn
          675                     680                     685
Lys  Ala  Gln  Ile  Tyr  Ala  Trp  Arg  Lys  Gly  Ile  Lys  Thr  Leu  Tyr  Tyr
     690                     695                          700
Ile  Arg  Leu  Arg  Gln  Met  Ala  Leu  Glu  Gly  Thr  Glu  Val  Glu  Gly  Cys
705                     710                     715                          720
Val  Ser  Cys  Met  Leu
               725
```